United States Patent [19]

Ueno et al.

[11] Patent Number: 5,770,759

[45] Date of Patent: Jun. 23, 1998

[54] PROSTAGLANDINS OF THE F SERIES

[75] Inventors: Ryuzo Ueno; Ryuji Ueno, both of Nishinomiya; Tomio Oda, Itami, all of Japan

[73] Assignee: R-Tech Ueno, Ltd., Osaka-Fu, Japan

[21] Appl. No.: 701,865

[22] Filed: Aug. 23, 1996

Related U.S. Application Data

[62] Division of Ser. No. 361,712, Dec. 22, 1994, Pat. No. 5,591,887, which is a continuation of Ser. No. 43,177, Apr. 2, 1993, abandoned, which is a division of Ser. No. 945,594, Sep. 16, 1992, Pat. No. 5,221,763, which is a continuation of Ser. No. 607,791, Oct. 31, 1990, abandoned, which is a continuation of Ser. No. 189,100, May 2, 1988, abandoned.

[30] Foreign Application Priority Data

Apr. 30, 1987 [JP] Japan .................................. 62-107529
Sep. 18, 1987 [JP] Japan .................................. 62-235890

[51] Int. Cl.$^6$ ................................................ C07C 405/00
[52] U.S. Cl. ............................ 560/53; 560/121; 562/463; 562/503
[58] Field of Search ...................... 560/53, 121; 502/503, 502/463

[56] References Cited

U.S. PATENT DOCUMENTS

| | | | |
|---|---|---|---|
| 3,896,156 | 7/1975 | Beal, III et al. ........................ | 560/121 |
| 4,128,713 | 12/1978 | Schneider et al. ...................... | 560/121 |
| 4,131,738 | 12/1978 | Smith ...................................... | 560/121 |
| 4,158,667 | 6/1979 | Axen ...................................... | 560/121 |

FOREIGN PATENT DOCUMENTS

| | | |
|---|---|---|
| 52-95644 | 8/1977 | Japan . |
| 60-208917 | 11/1985 | Japan . |

OTHER PUBLICATIONS

C.R. Pace–Asiak et al., "Application of Prostaglandin–Profiling Techniques to Study the Release of Prostaglandins from the Fetal Lamb Ductus Arteriosus," *Biochimica et Biophysica Acta* 750(1983)330–333.

M. Rigaud et al., "In Vitro Inhibition of Human Lymphocyte Transformation by Natural or Synthetic Prostaglandins," *Prostaglandins and Medicine* 3:167–172, 1979.

*Acta Pharmaceutica Sinica*, vol. 16, No. 5 (May 1981).

Jones, Advances in Prostor Thromb. Res. 1 221–230 (1976).

*Primary Examiner*—Robert Gerstl
*Attorney, Agent, or Firm*—Sughrue, Mion, Zinn, Macpeak & Seas, PLLC

[57] ABSTRACT

The present invention provides new compounds, 13,14-dihydro-15-keto-PGFs, and vassopressors containing them, which raise blood pressure without substantial ephemeral depression of blood pressure, trachea or enteron contraction effect inherent in usual PGFs.

13 Claims, 27 Drawing Sheets

PROSTAGLANDINS OF THE F SERIES

This is a divisional of application No. 08/361,712 filed Dec. 22, 1994, now U.S. Pat. No. 5,591,887, which is a Divisional of prior application No. 07/945,594 filed Sep. 16, 1992 (now U.S. Pat. No. 5,221,763), which is a Continuation of prior application No. 07/607,791 filed Oct. 31, 1990 (abandoned), which is a Continuation of prior application No. 07/189,100 filed May 2, 1988 (abandoned).

BACKGROUND OF THE INVENTION

The present invention relates to novel prostaglandins of the F series and vasopressors containing the same.

Prostaglandins of the F series (hereinafter referred to as PGFs) which contain a partial structure as a five-membered ring shown in the following formula:

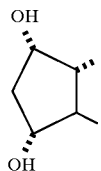

may be roughly divided into PGF$_1\alpha$:

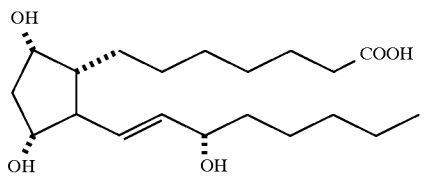

in which the carbon atom at 5-position (referred to as C-5 hereinafter, such nominating is applied to other carbon) and C-6 are singly bonded, and PGF$_2\alpha$:

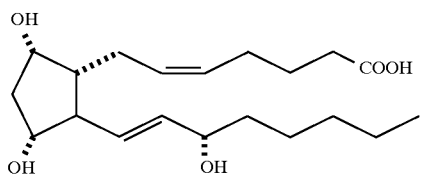

in which C-5 and C-6 are doubly bounded, and PGF$_3\alpha$:

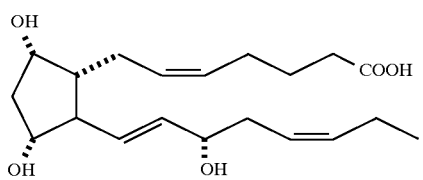

in which C-5 and C-6 are, and C-17 and C-18 are are double bonded. For example, PGF$_2\alpha$ which exhibits marked oxytocil effect is clinically used to induce or promote pain at the last stage of pregnancy. Moreover, it is known to have vasopressor effect, however, the effect of PGF$_2\alpha$ is accompanied with preceding ephemeral vasorelaxation. Further, the typical PG effects on trachea, bronchus and intestine such as increase of airway resistance due to tracheal contraction and abdominal pain due to intestinal contraction, are simultaneously accompanied with vasopressor effect, therefore, there are problems to use the PGFs as vasopressors.

On the other hand, prostaglandin F metaboletes in which the bond between C-13 and C-14 is saturated, and C is a carbonyl group, are found to exist in human and animal metabolites. These 13,14-dihydro-15-keto-prostaglandin are shown in the formulae following:

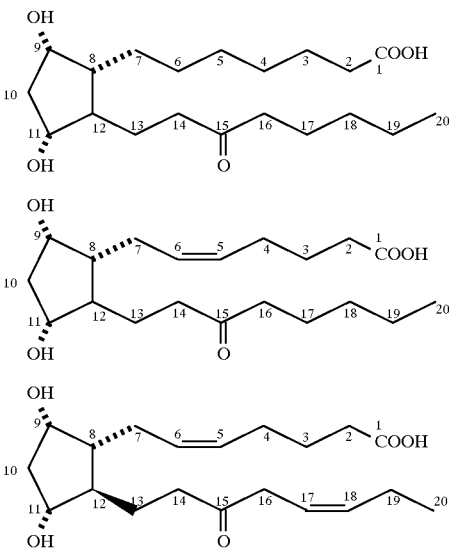

and are known as the metabolites of the corresponding PGF$_1\alpha$, PGF$_2\alpha$, and PGF$_3\alpha$ in vivo. These 13,14-dihydro-15-keto-PGFs scarcely exhibit any physiological activities that PGFs inherently possess, and have been reported as the physiologically-, and the pharmacologically- inactive metabolites (see, Acta Physiologica Scandinabia, 66, P 506- (1988)).

SUMMARY OF THE INVENTION

While evaluating pharmacological activities of the derivatives of the above metabolites, however, the present inventors have found that carboxylic-acid esters of the above metabolites themselves, 13,14-dihydro-15-keto-PGF analogues, which are carboxylic acids, corresponding salts, and corresponding esters, bearing substituents on C-3, -16, -17, -19, and/or -20 and 13,14-dihydro-15-keto-PGF analogues which bear a methyl group or a hydroxymethyl group instead of a hydroxy group on C-9 or C-11, show vasopressor activity, which is one of the phermaceutical activities of the PGFs. The vasopressor effect of these 13,14-dihydro-15-keto-PGFs may raise blood pressure without ephemeral vasorelexation which is inherent to the PGFs. Further, 13,14-dihydro-15-keto-PGFs, which show no or extremely reduced tracheal and intestineal contraction effects those the PGFs inherently possess are found to have no typical PG effects on trachea, bronchus and intestine.

DETAILED DESCRIPTION OF THE INVENTION

Figure 1:
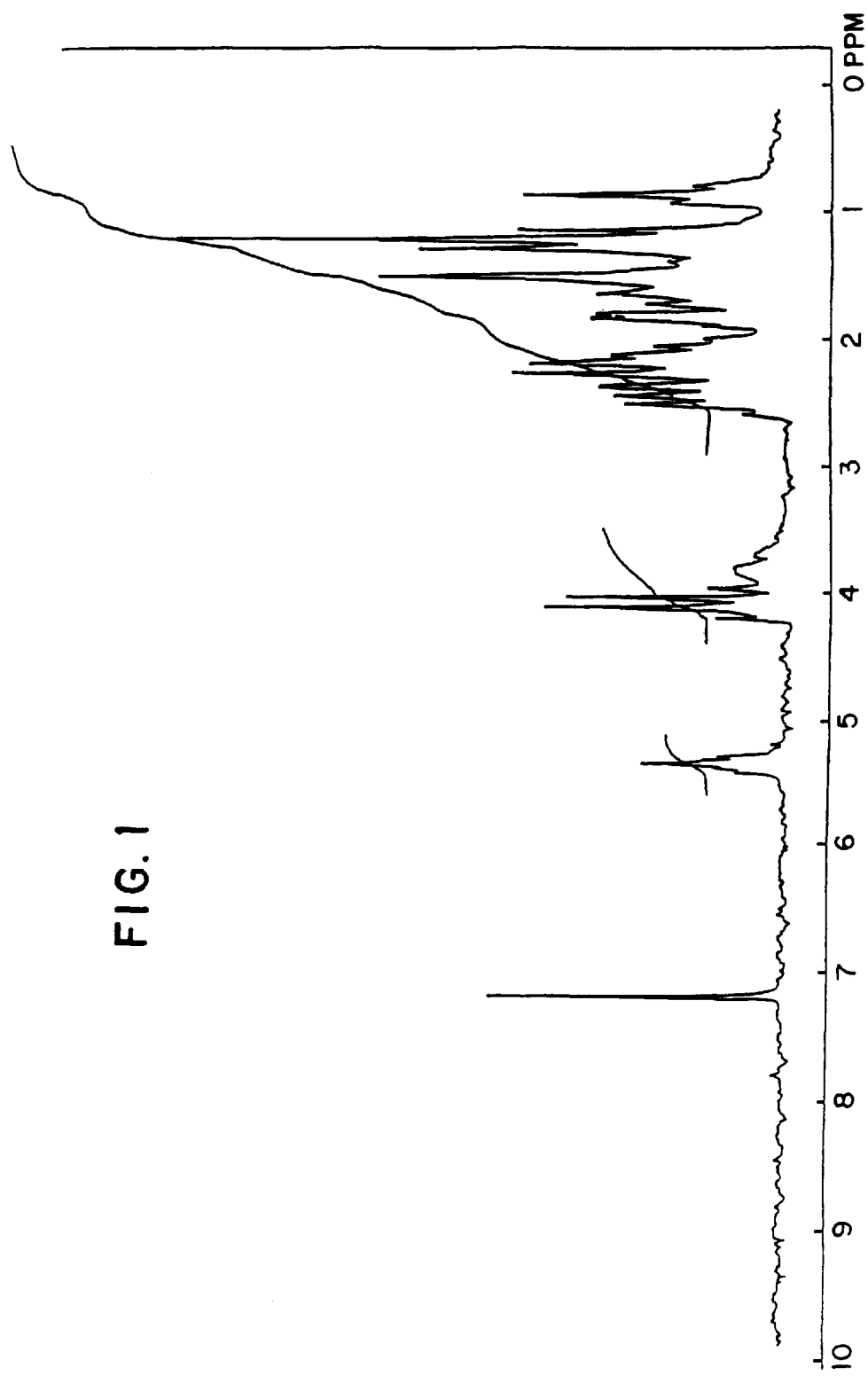
FIGS. 1–27 are n.m.r. charts of 13,14-dihydro-15-keto-PGFs of the present invention.

The present invention provides 13,14-dihydro-15-keto-PGFs and the corresponding salts shown in the general formula and vasopressors containing the compounds;

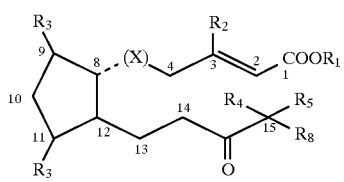

in the formula C-2, -3 double bond may or may not be located; X is

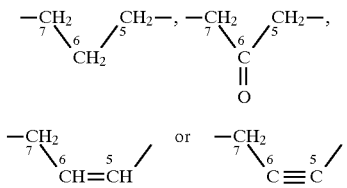

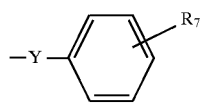

one of four possibilities shown above $R_1$ is a hydrogen atom, an alkyl, phenyl, benzoyl, hydroxyalkyl, alkoxyalkyl, trialkylsilyl and tetrapyranyl group;

$R_2$ is a hydrogen atom or a lower alkyl group;

$R_3$ and $R_3'$ are a hydroxyl, methyl or hydroxymethyl;

$R_4$ and $R_5$ are the same or different, and signify a hydrogen atom, a lower alkyl or a halogen atom; and $R_6$ is either an alkyl group consisted of 4 to 9 carbons which may or may not be branched one, contain double bonds or may bear alkoky substituents or the group shown in the formula following:

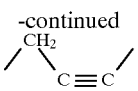

(wherein Y indicates a single bond with C-16, or an oxygen atom; $R_7$ indicates a hydrogen or halogen atom or a halgenated alkyl); excepting the compound wherein $R_1$, $R_2$, $R_4$ and $R_5$ are simultaneously hydrogen atoms, $R_6$ is a n-Bu, $R_3$ and $R_3'$ are both hydroxyls and C-2 and C-3 are singlly bonded.

X in the general fromula represents the four types of the partial structure illustrated above.

A compound in which —(X)— signifies

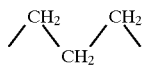

is 13,14-dihydro-15-keto-PGF$_1$s and a compound wherein —(X)—signifies

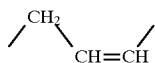

is 13,14-dihydro-15-keto-PGF$_2$s. Accordingly, the compounds wherein —(X)-signifies

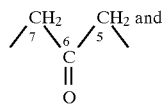

are 13,14-dihydro-6,15-diketo-PGF$_1$s, and 13,14-dihydro-15-keto-5,6-dehydro-PGF$_2$s, respectively.

In the present invention, $R_1$ indicates a hydrogen atom, alkyl, phenyl, benzyl, hydroxyalkyl, alkoxyalkyl, trialkylsilyl, and tetrahydropyranyl. A preferable $R_1$ in the present invention is an alkyl group, more preferably, a saturated or an unsaturated alkyl group which may or may not have a side chain and particularly an alkyl group which may contain 1 to 4 carbon atoms, for example, methyl, ethyl, n-propyl, isopropyl, n-butyl, isobutyl, t-butyl and the like.

13,14-Dihydro-15-keto PGFs in this invention may be in a salt form. The salts are physiologically acceptable ones, for example, salts with alkali metals such as sodium, potassium and salts with alkaline earth metals such as calcium, magnesium or physiologically acceptable ammonium salts, for example, ammonium salts derived from ammonia, methylamine, dimetylamine, cyclopentylamine, benzylamine, piperidine, monoethanolamine, diethanolamine, monomethylmonoethanolamine, tromethamin, lysine, and tetraalkylammonium salt and the like.

$R_2$ is a hydrogen or a lower alkyl group, especially methyl.

$R_3$ and $R_3'$ are a hydroxyl, methyl or hydroxymethyl. When they are both hydroxyls, the compound belongs to the general 13,14-dihydro-15-keto-PGFs. In the present invention, the compounds wherein $R_3$ and/or $R_3'$ are/is methyl or hydroxymethyl are also considered as PGFs.

$R_3$ may be α-oriented or β-oriented and $R'_3$ may be α-oriented or β-oriented with respect to C-9 or C-11 respectively.

$R_4$ and/or $R_5$ independently indicate a hydrogen atom, a lower alkyl group or a halogen atom. In case of a lower alkyl group, methyl group is especially preferred, and in case of halogen a fluorine atom is especially preferred. The compound in which at least one of $R_4$ and $R_5$ is a metyl or a fluorine atom is important. Both $R_4$ and $R_5$ may indicate the same substituents.

$R_6$ is an alkyl consisted of 4 to 9 carbons, which may contain side chains, a double bonds or alkoxy substituents. The alkoxy substituents include such as methoxy, ethoxy and the like. Especially, n-alkyl groups consisted of 5 to 8 carbons preferred, and a n-alkyl group of 6 carbons is particularly important. Alternatively, $R_6$ is the group shown in the formula following:

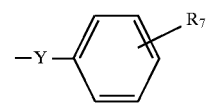

wherein Y indicates a bond with C-16 or an oxygen atom, $R_7$ is a hydrogen atom, halogen atom or halogenated alkyl group. Preferably, Y, and $R_7$ are an oxygen atom, and a halogenated alkyl group, respectively.

The typical compounds of the present invention are, for example;
carbonylic acid esters of 13,14-dihydro-15-keto-PGF;
13,14-dihydro-15-keto-16R,S-fluoro-PGFs;
13,14-dihydro-5-keto-16,16-difluoro-PGFs;
13,14-dihydro-15-keto-16R,S-methyl-PGFs;
13,14-dihydro-15-keto-16,16-dimethyl-PGFs;
13,14-dihydro-15-keto-17S-methyl-PGFs;

13,14-dihydro-15-keto-9β-PGFs;
13,14-dihydro-15-keto-11β-PGFs;
13,14-dihydro-15keto-11-dehydroxy-11R-methyl-PGFs;
13,14-dihydro-15-keto-16R,S-fluoro-11R-dehydroxy-11R-methyl-PGFs,
13,14-dihydro-15-keto-20-methoxy-PGFs;
13,14-dihydro-15-keto-20-methyl-PGFs;
13,14-dihydro-15-keto-20-ethyl-PGFs;
13,14-dihydro-15-keto-20-n-propyl-PGFs;
13,14-dihydro-15-keto-20-n-butyl-PGFs;
13,14-dihydro-15-keto-20-ethyl-16R,S-fluoro-PGFs;
13,14-dihydro-15-keto-20-ethyl-11-dehydroxy-11R-methyl-PGFs;
13,14-dihydro-15-keto-20-ethyl-16R,S-fluoro-11-dehydroxy-11R-methyl-PGFs;
13,14-dihydro-15-keto-16-desbutyl-16-trifluoromethylphenoxy-PGFs.

Though PGFs are usually named according to the skeleton of prostanoic acid as named hereinbefore, these may be named based on IUPAC nomenclature. According to it, for example, PGF$_1$α is nominated as 7-[(1R,2R,3R,5S)-3,5-dihydroxy-2{(E)-(3S)-3-hydroxy-1-octenyl}-cyclopentyl]-heptanoic acid; PGF$_2$α is (Z)-7-[(1R,2R,3R,5S)-3,5-dihydroxy-2-{(E)-(3S)-3-hydroxy-1-octenyl}-cyclopentyl]-5-heptenoic acid; 13,14-dihydro-15-keto-20-ethyl-PGF$_2$α isopropyl ester is isopropyl(Z)-7-[(1R,2R,3R,5S)-3,5-dihydroxy-2-{3-oxo-1-decyl}cyclopentyl]-hept-5-enoate; and 13,14-diydro-15-keto-20-methyl-PGF$_2$α methyl ester is methyl (Z)-7-{(1R,2R,3R,5S)-3,5-dihydroxy-2-(3-oxo-1-nonyl)-cyclopentyl}-kept-5-enoate.

13,14-Dihydro-15-keto-PGFs of the present invention rapidly shows great vasopressor activity without ephemeral vasorelaxation which is inherent to PGFs. Further, they are found to show no effect on trachea, bronchus and intestine such as increase of airway resistance due to contraction of trachea, and abdominal pain or diarrhea due to contraction of intestine, which are inherent to PGs, and found to have low toxicity. Therefore, they are extremely useful as a vasopressor. In addition, according to such vasopressor activity, they can be used as a remedy for essential hypotension, symptomatic hypotension, orthostatic hypotension, acute hypotension accompanied with various diseases and conditions, and can be used as a adjunctive remedy for shock and the like.

In order to prepare 13,14-dihydro-15-keto-PGFs of the present invention, as shown in the attached sythetic charts, the commercially available (−)-Corey lactone (1) is used as the starting material and subjected to Collines oxidation to give aldehyde (2), which is allowed to react with dimethyl (2-oxoalkyl)phosphonate to give α,β-unsaturated ketone (3). After reduction, a carbonyl group of the resulting saturated ketone (4) is protected. An alcohol obtained after the removal of p-phenyl benzoyl from ketone (4) is reprotected by THP, and lactone (7) is redeuced to lactol, and then an α-chain is introduced by Wittig reaction.

13,14-Dihydro-15-keto-PGF$_2$s in wchich —(X)— is

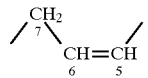

can be obtained after reduction of lactone (7) to lactol (8), which is subsequently reacted with (4-carboxybutyl) triphenylphosphorane, and 13,14-dihydro-15-keto-PGF$_1$s, in which —(X)— is

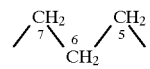

can be obtained after hydrogenation of 13,14-dihydro-15-keto-PGF$_2$s.

13,14-Dihydro-6,15-diketo-PGF$_1$s in which —(X)— is

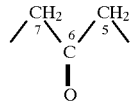

can be obtained by treating bromo- or iodo- ether obtained after cyclization between C-5, -6-double bond shown below

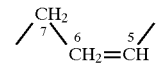

and the hydroxyl group on C-9 using N-bromosuccinimide or iodine, that is to say, addition of a bromine atom or an iodine atom on C-5 and simultaneous cyclization between C-6 and the hydroxyl group on C-9, with DBU, and hydrolysis of the resulting enol ether with acid to produce 6-keto group.

The synthesis of 13,14-dihydro-15-keto-5,6-dehydro-PGF$_2$s in which (X) is

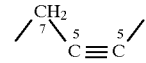

involves 1,4-addition of monoalkylcopper complex or dialkylcopper complex of the following formulae;

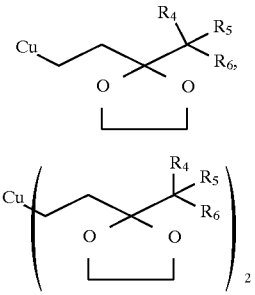

to 4R-t-butyldimethylsilyloxy-2-cyclopenten-1-one, alkylation of the resulting copper enolate after 1,4-addition with 6-alkoxycarbonyl-1-iodo-2-hexyne or its derivatives, and reduction of the resulting 13,14-dihydro-15-keto-PGE$_2$ types, for example, with sodium borohydride.

13,14-Dihydro-15-keto-PGF in which R$_3$ is a methyl group can be obtained after reacting PGA types, which can be prepared by Jones oxidation of the hydroxyl: group or C-9 of 11-tosylate derivatives of PGF types, with dimethylcopper complex, and by reducing the resulting 11α-methyl-PGE$_2$ with sodium borohydride. Alternatively, it can be obtained by protecting the carbonyl group of the saturated ketone (4) prepared after reduction of the unsaturated ketone (3), converting the alcohol obtained after removal of p-phenylbenzoyl group from the saturated ketone (4) to the corresponding tosylate, treating the tosylate with DBU, converting the resulting unsaturated lactone to the corresponding lactol, introducing an α-chain by Wittig reaction, oxidizing the resulting alcohol (9-position) to the corresponding PGA, reaction of the product (PGA) with dimethylcopper complex to introduce a methyl group at the 11-position, and reducing the resulting 11-methyl PGE with, for example, sodium borohydride.

13,14-Dihydro-15-keto-PGFs in which $R_3'$ is a hydroxymethyl group can be synthesized by adding methanol to thus obtained corresponding PGA types using benzophenone as a photosensitizer and reducing the resulting 11-hydroxymethyl PGE type, for example, with sodium borohydride.

13,14-Dihydro-15-keto-PGFs in which either $R_4$ or $R_5$ is other than a hydrogen atom and $R_6$ is other than n-butyl may be obtained by using the corresponding dimethyl (2-oxoalkyl)phospnonate to obtain $\alpha,\beta$-unsaturated ketone (3). For example, 13,14-dihydro-15-keto-PGFs in which $R_4$ is a fluorine atom, $R_6$ is n-butyl, and $R_5$ is a hydrogen atom, can be obtained by using dimethyl (3-fluoro-2-oxoheptyl) phosphonate, and those wherein $R_4$ and $R_5$ are both hydorogen atoms and $R_6$ is hexyl, may be obtained by using dimethyl (2-oxononyl)phosphonate.

The synthetic methods of the compounds in the present invention may not be limited to ones described above, and the suitable means for protection of the respective functional groups, oxidation, reduction and the like may be optionally employed.

Prostaglandins F of the present invention can be used as medicaments for animal and human, and, in general, used for systemic or local application by oral administration, intravenous injection, subcutaneous injection and the like. The dosage varies depending on animal, human, age, weight, conditions, therapeutic effect, administration route, treatment time and the like.

The solid composition for oral administration of the present invention includes tablets, powder, granules and the like. In such solid composition, one or more active ingredient may be mixed with at least one inactive diluent, for example, lactose, mannitol, glucose, hydroxypropyl cellulose, microcrystalline cellulose, starch, polyvinyl pyrrolidone, magnesium aluminate metasilicate and the like. According to the conventional manner, the composition may contain additives other than inactive diluent, for example, lubricant such as magnesiun stearate, disintegrant such as fibrous calcium gluconate, stabilizer such as etherfied cyclodextrin such as a, $\alpha$, $\beta$- or $\gamma$-cyclodextrin, dimethyl-$\alpha$-, dimethyl-$\beta$-, trimethyl-$\beta$- or hydroxypropyl-$\beta$-cyclodextrin, branched cyclodextrin such as glucosyl-, maltosyl-cyclodextrin, formulated cyclodextrin, cyclodextrin containing sulfur, mitthoprotol, phospholipid and the like. When the above cyclodextrins are used, clathrate compound with cyclodextrin may be often formed to enhance stability. Alternatively, phospholipid may be used to form liposome, often resulting in enhanced stability.

Tablets or pills may be coated with film soluble in the stomach or intestine such as suger, gelatin, hydroxypropyl cellulose, hydroxypropylmethyl cellulose phthalate and the like, or with more than two layers. Further, they may be formed as capsules with absorbable substances such as gelatin.

Liquid composition for oral administration may contain pharmaceutically acceptable emulsion, solution, suspension, syrup, elixyr as well as generally used inactive diluent, for example, purified water, ethanol, vegetable oil such as coconut oil. Such composition may contain adjuvants such as wetting agent and suspension, sweetening agent, flavoring agent, preservatives and the like other than inactive diluent. Such liquid composition may be used by directly enclosing in soft capsules.

Other compositions or oral administration, which may contain one or more active ingredient, include spray formulated by known method.

Injection for parenteral administration according to the present invention includes steril, aqueous or non-aqueous solution, suspension, emulsion and detergent.

Such aqueous solution and suspension include, for example, injectable distilled water, physiological saline and Ringer. Non-aqueous solution and suspension include, for example, propylene glycol, polyethylene glycol, vegetabel oil such as olive oil, alcohols such as ethanol, polysorbate and the like. Such composition may contain adjuvants such as preservatives, wetting agent, emulsifier, dispersant and the like. These are sterlized, for example, by filtration through bacteria-holding filter, compounding with germicides or irradiation of UV rays. These may be used by producing sterile solid composition and dissolving in sterile water or sterile solvent for injection before use.

The present invention will be illustrated in the following example.

EXAMPLE 1

(1) synthesis of dimethyl(7-methoxy-2-oxoheptyl)-phosphonate

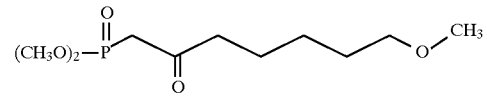

(1-1) Methyl 6-methoxy-caproate:

Sodium hydride (NaH) (50%, 6.12 g) suspended in tetrahydrofuran (TEF) (60 ml) was added to a solution of 1,6-hexanediol (15.0 g) in THP (200 ml), and kept at 60° C. until gas evolution stopped. After cooling, a solution of methyl iodide (12 ml) in THF (35 ml) was added and kept overnight at room temperature. The crude product obtaind after the usual work-up was chromatographed to give 6-methoxy-1-hexanol. Yield; 8.16 g 6-Methoxy-hexanol (8.16 g) was oxidized with Jones reagent (2.67-M, 53 ml) in acetone (100 ml) at −10° C. to give 6.17 g of 6-methoxy-caproic acid.

6-Methoxy-caproic acid (6.17 g) was dissolved in dry methanol (90 ml) containing hydrogen chloride (catalytic amount) and held overnight at room temperature. The solvent was distilled off from the reaction solution under reduced pressure to give methyl 6-methoxy-caproate. Yield; 5.68 g (1-2) Dimethyl (7-methoxy-2-oxoheptyl)phsophonate:

A solution of dimethyl methylphosphonate (8.88 g)in THF (60 ml) was cooled to −60° C., to which n-butyllithium (1.55-M, 46.2 ml) was added dropwise. After addition, the solution was stirred at −60° C. for 30 minutes. A solution of methyl 6-methoxy-caproate (5.65 g) in THF (50 ml) was added dropwise to the resulting solution and held at −60° C. overnight, and at room temperature for 2 hours. After the reaction solution was cooled to 0° C., the reaction was neutralized by addition of acetic acid (4 ml). The crude product obtained after the usual work-up was chromatographed (dichloromethane/methanol (5%)).

(2) Synthesis of dimethyl (2-oxononyl)phosphonate

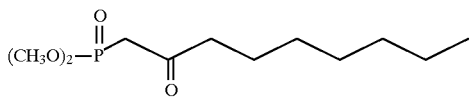

A solution of dimethyl methylphosphoanate (24.3 ml) in THF (500 ml) was cooled to −78° C., to which n-butyllithium (1.6 - M, 136 ml) was added dropwise. After addition, the solution was stirred for one hour, and then ethyl octanoate (28.5 ml) was added dropwise. The reaction was stirred at −78° C. for 10 hours. Acetic acid (12.5 ml) was added to the reaction cooled at 0° C., and the solution was brought to room temperature and concentrated under reduced pressure. The residue was diluted with ethyl acetate, and the solution was washed with brine and dried. The crude product obtained after concentration under reduced pressure was chromatographed (hexane/ethyl acetate=1/1) to give dimethyl (2-oxononyl)phosphonate. Yield; 30.2 g (83%)

(3) Synthesis of dimethyl (3,3-dimethyl-2-oxoheptyl)phosphonate

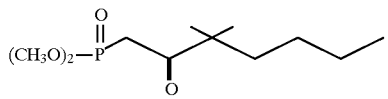

(3-1) Ethyl 2,2-dimethyl-caproate:

A solution of isobutyric acid (45 g) in THF was added to LDA prepared at −78° C. according to the conventional manner and stirred for one hour. A solution of butyl iodine (107 g) in dry HMPA was added, and stirred at −78° C. for one hour, and at room temperature for additional one hour. The crude product obtained after the conventional work-up was distilled.

Yield; 50 g (75%), b.p.; 68°/25 mmHg (3-2) Dimethyl (3,3-dimethyl-2-oxoheptyl)phosphonate:

A solution of dimethyl methylphosphonate (35.0 ml) in THF (300 ml) was cooled to −78° C., to which n-butyllithium (1.6 - M, 196 ml) was added dropwise. After stirring at −78° C. for one hour, a solution of ethyl 2,2-dimethylcaproate (27 g) in dry TEF was added. The reaction solution was stirred at −78° C. for one hour, and then at room temperature for additional 2 hours. The reaction solution was cooled to 0° C. and acetic acid (18 ml) was added thereto. The crude product obtained after the conventional work-up was distilled under reduced pressure and the resulting fraction (>130° C.) was chromatographed to give dimethyl (3,3-dimethyl-2-oxoheptyl)phosphonate. Yield, 9.72g (26%)

(4) Synthesis of dimethyl (3-fluoro-2-oxoheptyl) phosphnate (4-1) Methyl 2-fluorocaproate:

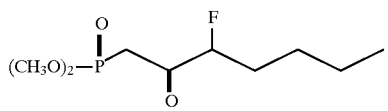

Methyl 2-bromocaproate (40 g) was added to anhydrous potassium fluoride (23 g) in acetamide (23 g) kept at 105° C. The mixture was vigorously stirred at 105° C. for 6 hours. The crude product obtained after the conventional work-up was distilled. Yeiled; 20 g (71%), b.p.; 66° C./20 mmHg (4-2) Dimethyl (3-fluoro-2-oxoheptyl)phosphonate:

Dimethyl methylphosphonate (8.38 g) was dissolved in dry THF (250 ml) and cooled to −78° C. n-Butyllithium (1.6-M, 42 ml) was added dropwise, and the reaction was stirred for 10 minutes. The above methyl fluorocaproate (200 g) in THF (10 ml) was added dropwise. After addition, the mixture was stirred at −78° C., for 45 minutes, and then at room temperature for additional 45 minutes. The crude product obtained after the conventional work-up was chromatographed (hexane/ethyl acetate-1/1). Yield; 5.04 g (62 g)

(5) Synthesis of dimethyl (4S)-methyl-2-oxoheptyl-phosphonate

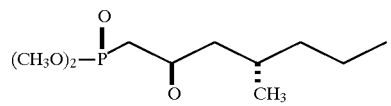

(5-1) Ethyl 3S-methyl-caproate:

Sodium ethoxide was prepared from sodium metal (7.61 g) in absolute methanol (200 ml). Diethyl malonate (50.3 ml) was added dropwise, and the solution was heated to 80° C. 2-Bromopentane (50 g) was added and the resultant was refluxed for 24 hours. According to the conventional work-up, diethyl (2-pentyl)-malonate (62.7 g) was obtained. Diethyl (2-pentyl)malonate was added to 50% aqueous solution of potassium hydroxide, and heated for 3 hours while water/ethanol was distilled off. After cooling, the resultant was acidified with concentrated hydrochloric acid, and subsequently extracted with ethyl acetate. The product obtained after concentration under reduced pressure was heated at 180° C. until gas evolution stopped. After distillation, colorless 3R,S-methyl-caproic acid was obtained. Yield; 27.7 g (35%), b.p. >200° C./760 mmHg 3R,S-Methyl-caproic acid (27.7 g) was dissolved in ethanol (160 ml), and cinchonidine (64 g) was dissolved thereto with heating. The salt obtained after concentration under reduced pressure was recrystallized six times from 60% methanol to give colorless needlelike crystals. Yield; 14.4 g, $[\alpha]_D^{31°}=-3.3°$ (c=13.6 in benzene, lit. −3.1°)

The above 3S-methyl-caproic acid (3.94 g) was converted into ethyl ester using ethanol and catalytic amount of sulfuric acid. Yield; 4.04 g (84%)

(5-2) Dimethyl (4S-methyl-2-oxpheptyl)phosphonate:

The title compound was synthesized according to the conventional method with using ethyl 3S-methyl-caproate and dimethyl methylphosphonate.

EXAMPLE 2 (cf. Synthetic scheme I)

Synthesis of 13,14-dihydro-15-keto-PGF$_2\alpha$ ehtyl ester (11); R=Et:

(2-1) Synthesis of 1S-2-oxa-3-oxo-6R-(3-oxo-1-trans-octenyl)-7R-(4-phenylbenzoyl)oxy-cis-bicyclo(3,3,0)-octane (3):

Dimethyl (2-oxoheptyl)phosphonate (8.9 ml) was added dropwise to a suspension of NaH (60%, 1.76 g) in THF (200 ml) and stirred for 30 minutes. To the generated phosphonate anion was added aldehyde (2) in THF (400 ml), which was obtained by Collins oxidation of (−)-Corey lactone (1) (15 g). The reaction solution was kept overnight at room temperature and acetic acid was added thereto. After the usual work-up, α,β-unsaturated ketone (3) was obtained. Yield; 11.8 g (62%)

(2-2) Synthesis of 1S-2-oxa-3-oxo-6R-(3,3-ethylenedioxyoctyl)-7R-(4-phenylbenzoyl)oxy-cis-bicyclo-(3,3,0)octane (5):

The unsaturated ketone (3) (11.8 g) was hydrogenated with using 5% palladium/carbon (0.300 g) in ethyl acetate (100 ml) to give ketone (4). The ketone (4) (11.8 g) was dissolved in toluene (200 ml), to which were added ethylene glycol and p-toluenesulfonic acid (catalytic amount). The solution was refluxed overnight while water produced was azeotropically distilled off. After the usual work-up, ketal (5) was obtained. Yield; 11.8 9 (91%)

(2-3) Synthesis of 1S-2-oxa-3-oxo-6R-(3,3-ethylenedioxy-1-octyl)-7R-hydroxy-cis-bicyclo-(3,3,0)octane (6):

The compound (5) (11.8 g) was dissolved in methanol (100 ml) and THF (20 ml), and potassium carbonate (3.32 g) was added thereto. The reaction mixture was stirred at room temperature for 7 hours. The crude product obtained after the usual work-up was chromatographed (ethyl acetate/hexane-1/3-1/1) to give alcohol (6). Yield; 6.78 g (90%)

(2-4) Synthesis of tetrahydropyranyl ether (7):

To the dichloromethane solution (100 ml) of the compound (6) (6.78 g) was added dihydropyran (4 ml) and p-toluenesulfonic acid (catalytic amount). The reaction was stirred for 20 minutes. After the usual work-up, the resulting crude product was chromatographed (ethyl acetate/hexane =2/1) to yield the tetrahydropyranyl ether (7). Yield; 8.60 g (100%)

This operation was repeated and 14.67 g of the product in total was obtained.

(2-5) Synthesis of lactol (8):

Diisobutylaluminium hydride (DIBAL-H) (1.5-M, 50 ml) was added dropwise to the tetrahydropyranyl ether (7) (14.67 g) in dry toluene (100 ml) at –78° C. and stirred for 60 minutes. After the usual work-up, lactol (8) was obtained.

(2-6) Synthesis of 13,14-dihydro-11-(2-tetrahydropylanyl)oxy-15,15-ethylenedioxy-PGF$_2\alpha$(9):

Sodium hydride (60%, 11.1 g) washed with pentane was suspended in DMSO (150 ml), and stirred at 60°–70° C. for 3 hours. The generated sodium methylsulfinyl carbanion was cooled, and (4-carboxybutyl)tripheylphosphonium bromide (65.6 g) in DMSO was added to the carbanion solution. The reaction mixture was stirred for 30 minutes. The lactol (8) in DMSO (80 ml) was added to the generated ylide. After stirring overnight, the reaction solution was poured onto ice/water, and the pH value was adjusted to 12 with 5% sodium hydroxide solution and extracted with ether. The aqueous layer was adjusted to pH 4–5 with 4N hydrochloric acid and extracted with ethyl acetate. The commbined ethyl acetate layers were washed with brine, and dried over magnesium sulfate. The solvent from the ethyl acetate extracts was distilled off under reduced pressure to leave a crude product. The crude product was dissolved into ether, and the insoluble matters were filtered off, and the filtrate was concentrated under reduced pressure to give the compound (9). Yield; 15.17 g (85%)

(2-7) Synthesis of 13,14-dihydro-11-(2-tetrahydropylanyl)oxy- 15,15-ethylenedioxy-PGF$_2$a ethyl ester (10):

Carboxylic acid (9) (12.1 g) was treated by DBU (4.9 ml) and ethyl iodide (2.4 ml) in anhydrous acetonitrile (100 ml) at 60° C. for 2 hours. The crude product obtained after the usual work-up was chromatographed (ethyl acetate/hexane= 1/3 ) to give ethyl ester (10). Yield, 8.52 g (63%)

(2-8) Synthesis of 13,14-dihydro-15-keto-PGF$_2\alpha$ ethyl ester (11):

The compound (10) (0.200 g) in a mixed solvent (acetic acid/TRF/water=3/1/1) (5 ml) was kept at 50° C. for 4 hours. The solvent was distilled off under reduced pressure, and the resulting crude product was chromatographed (ethyl acetate/hexane=2/1) to give 13,14-dihydro-15-keto-PGF$_2\alpha$ ethyl ester (11). Yield, 0.054 g (41%)

NMR spectrum of 13,14-dihydro-15-keto-PGF$_2\alpha$ ethyl ester (11) is shown in FIG. 1. Mass (SIMS) m/z 383 (M+1), 365 (M+1–18)

EXAMPLE 3 (cf. Synthetic scheme I)

Synthesis of 13,14-dihydro-15-keto-PGF$_2\alpha$ methyl ester (11); R=Me:

In the same manner as described in Example 2, except that carboxylic acid (9) was converted into the corresponding methyl ester (10) with diazomethane, 13,14-dihydro-15-keto-PGF$_2\alpha$ methyl ester (11) was synthesized.

Figure 2:
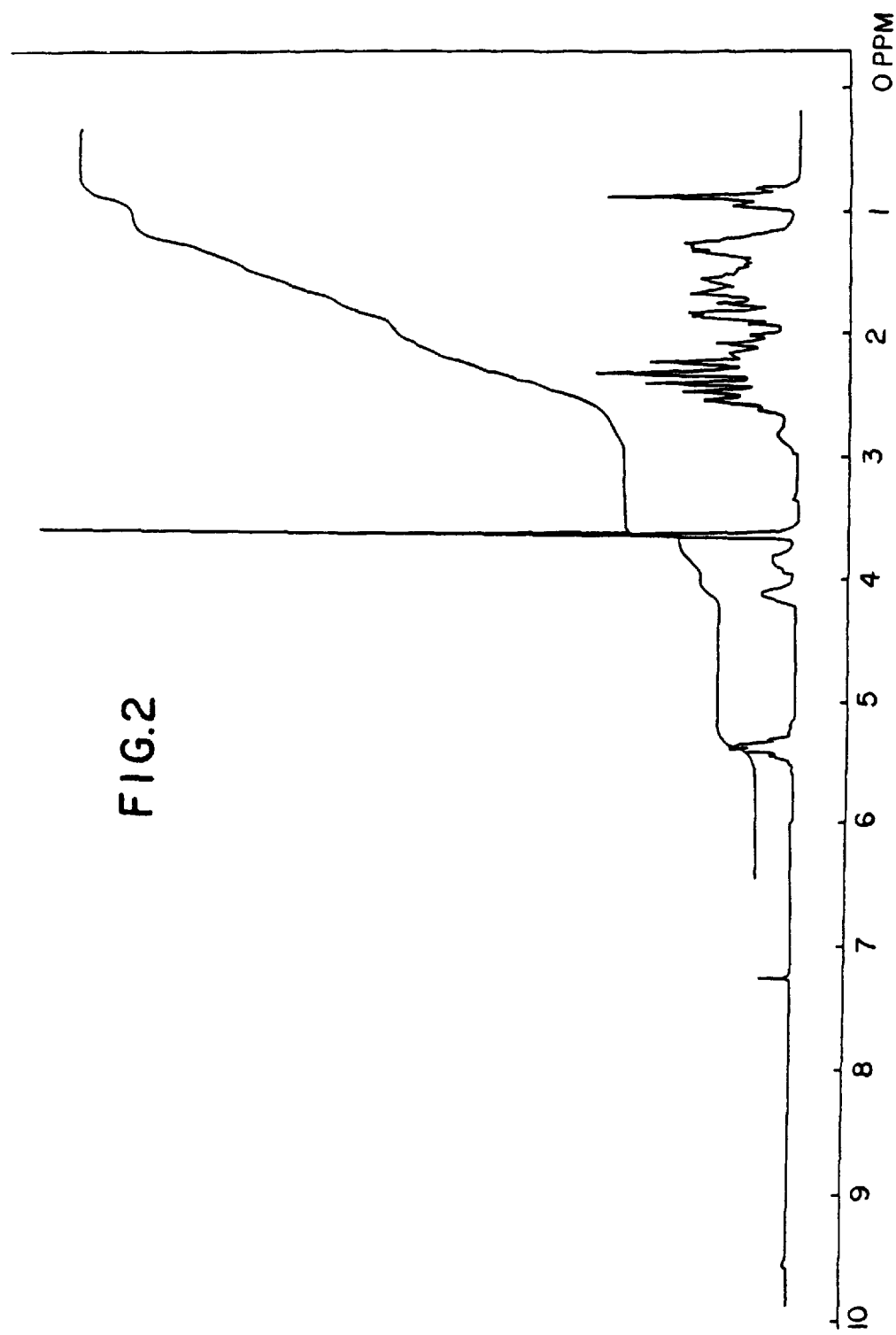

NMR spectrum of 13,14-dihydro-15-keto-PGF$_2\alpha$ methyl ester (11) is shown in FIG. 2. Mass (SIMS) NaCl added, m/z 391 (m$^+$+Na), 351 (m+1–18)

EXAMPLE 4 (cf. Synthetic scheme I)

Synthesis of 13,14-dihydro-15-keto-PGF$_1\alpha$ ethyl ester (13); R=Et:

(4-1) Synthesis of 13,14-dihydro-15,15-ethylenedioxy-11-(2-tetrahydropylanyl)oxy-PGF$_1\alpha$ ethyl ester (12):

13,14-dihydro-15,15-ethylenedioxy-11-(2-tetrahydropylanyl)oxy-PGF$_2\alpha$ ethyl ester (10) (3.50 g) was hydrogenated with using platinum oxide in ethanol (150 ml) and hydrogen. After the usual work-up, 13,14-dihydro-15,15-ethylenedioxy-11-(2-tetrahydropyranyl)oxy-PGF$_1\alpha$ ethyl ester (12) (3.50 g) was obtained.

(4-2) Synthesis of 13,14-dihydro-15-keto-PGF$_1\alpha$ ethyl ester (13):

Dihydro-PGF$_1\alpha$ derivative (12) (0.10 g) in a mixed solvent (acetic acid/water/THF=3/1/1) (10 ml) was kept at 50° C. for 6 hours. The solvent was distilled off under reduced pressure, and the resulting crude product was chromatographed (ethyl acetate/hexane=2/1) to give 13,14-dihydro-15-keto-PGF$_1\alpha$ ethyl ester (13). Yield; 0.0455 g (61%)

Figure 3:
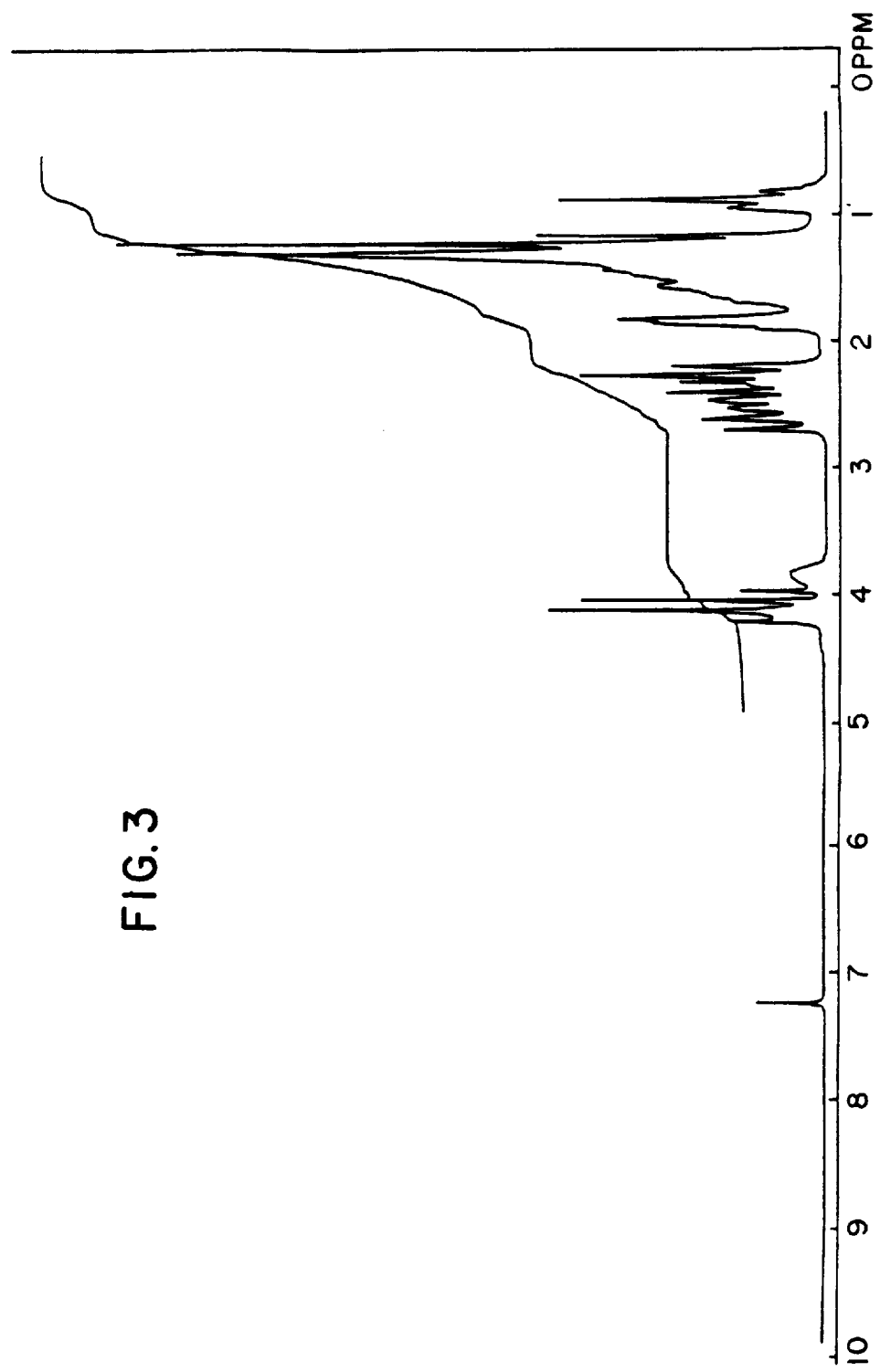

NMR spectrum of 13,14-dihydro-15-keto-PGF$_1\alpha$ ethyl ester (13) is shown in FIG. 3.

EXAMPLE 5 (cf. Synthetic scheme II)

Synthesis of 13,14-dihydro-15-keto-16R,S-fluoro-PGF$_2\alpha$ methyl ester (26):

(5-1) Synthesis of 1S-2-oxa-3-oxo-6R-(4R,S-fluoro-3-oxo-1-trans-octenyl)-7R-(4-phenylbenzoyl)oxy-cis-bicyclo-(3,3,0)octane (14):

Dimethyl (3R,S-fluoro-2-oxoheptyl)phosphonate(10.23 q) in THF was added to sodium hydride suspension in THF, and the mixture was stirred for 20 minutes at room temperature. To the above mixture was added the THF solution of aldehyde (2) obtained after Collins oxidation of (–)-Corey lactone (1) (15.00 g). After stirring at room temperature for 2 hours, the reaction solution was neutralized with acetic acid (15 ml). Subsequently, the residue obtained after the usual work-up was chromatographed (ethyl acetate/hexane= 1/2) to give enone (14). Yield; 10.45 g (53%)

(5-2) Synthesis of 1S-2-oxa-3-oxo-6R-(4R,S-fluoro-3R,S-hydroxy-1-octyl)-7R-(4-phenylbenzoyl)oxy-cis-bicyclo-(3,3,0)octane (16):

Enone (14) (10.45 g) was hydrogenated in ehtyl acetate (50 ml) using 5% palladium/carbon (1.0 g) and hydrogen to give ketone (15). Yield; 9.35 g (89%)

Ketone (15) (9.35 g) was reduced in absolute methanol (200 ml) with using sodium borohydride (1.15 g) to give colorless oil (16). Yield, 6.50 g (69%)

(5-3) 1S-2-oxa-3-oxo-6R-(4R,S-fluoro-3R,S-t-butyl-dimethylsilyloxy-1-octyl)-7R-hydroxy-cis-bicyclo-(3,3,0) octane (18).

Alcohol (16) (6.50 9) was converted to the corresponding t-butyldimethylsilyl ether (17) in anhydrous DMF (30 ml) with t-butyldimethylsilyl chloride (6.27 g) and imidazole (5.67 g). Yield; 8.80 g (100%)

t-Buthyldimethylsilyl ether (17) (8.80 g) was dissolved in methanol (80 ml). Anhydrous potassium carbonate (2.09 g) was added to the solution. After the reaction solution was stirred at room temperature for 4 hours, alcohol (18) as colorless oil was obtained after the conventional treatment. Yield; 4.11 g (67%)

(5-4) Synthesis of 13,14-dihydro-16R,S-fluoro-15R,S-t-butyldimethylsilyloxy-11R-(2-tetrahydropyranyl)oxy-$PGF_2\alpha$ methyl ester (22).

Alcohol (18) (4.11 g) was treated with dihydropyran (4.10 ml) and p-toluenesulfonic acid (catalitic amount) in dichloromethane (50 ml) at room temperature for 10 minutes. After the usual work-up, the obtained residue was chromatographed (ethyl acetate/hexane=1/4–1/3) to give tetrahydropyranyl ether (19) as a colorless oil. Yield; 5.08 g (100%)

Tetrahydropyranyl ether (19) (5.08 g) was reduced with DIBAL-H (1.5-M, 20 ml) in anhydrous toluene (60 ml) at −78° C. to give lactol (20) as a colorless oil.

According to the conventional method, ylide was prepared from (4-carboxybutyl)triphenylphosphonium bromide (18.51 g), and previously prepared lactol (20) in DMSO was added thereto. The resultant was stirred at room temperature for 2.5 hours. After the usual work-up, the obtained crude product was dissolved in ether, the insoluble matters were filtered off, and the filtrate was concentrated under reduced pressure to give a crude carboxylic acid (21). Yield; 8.0 g The crude carboxylic acid (21) (2.00 g) was converted to the corresponding methyl ester (22) in ether with diazomethane. The crude product obtained after the usual work-up was chromatographed (ethyl acetate/hexane=1/4–1/3) to give 13,14-dihydro-16R,S-fluoro-15R,S-t-butyldimethylsilyloxy-11R-(2-tetrahydropyranyl)oxy-$PGF_2\alpha$ methyl ester (22) (0.550 g).

(5-5) Tetrahydropyranyl ether formation of the compound (22):

Synthesis of bis-tetrahydropyranyl ether (23):

Alcohol (22) (0.550 g) was treated in anhydrous dichloromethane (30 ml) with dihydropyran (0.5 ml) and several pieces of p-toluenesulfonic acid at room temperature for 30 minutes. The crude product obtained after the usual work-up was chromatographed (ethyl acetate/hexane=1/6–1/3). to give bis-tetrahydropyranyl ether (23) as a colorless oil. Yield; 0.580 g (92%)

(5–6) Synthesis of 13,14-dihydro-16R,S-fluoro-$PGF_2\alpha$ methyl ester (26):

Bis-tetrahydropyranyl ether (23) (0.580 g) was treated overnight in anhydrous THF (20 ml) with tetrabutylammonuin fluoride (1.0-M, 10 ml) at room temperature. The crude product obtained after the usual work-up was chromatographed (ethyl acetate/hexane=1/3–1/2) to give alcohol (24) as a colorless oil. Yield; 0.300 g (62%)

Alcohol (24) (0.300 g) was oxidized with Jones reagent (2.67-M, 1.04 ml) in acetone (20 ml) at −10° C. The crude product obtained after the usual work-up was chromatographed (ethyl acetate/hexane=2/7) to give ketone (25) as a colorless oil. Yield; 0.280 g (94%)

Ketone (25) (0.280g) in a mixed solvent (acetic acid/water/THF=10/3.3/1) (25 ml) was kept at 55° C. for 2 hours. The solvent was distilled off under reduced pressure and the resulting crude product was chromatographed (ethyl acetate/hexane=2/3-1/1) to give 13,14-dihydro-15-keto-16R,S-fluoro-$PGF_2\alpha$ methyl ester (26). Yield; 0.123 g (63%)

Figure 4:
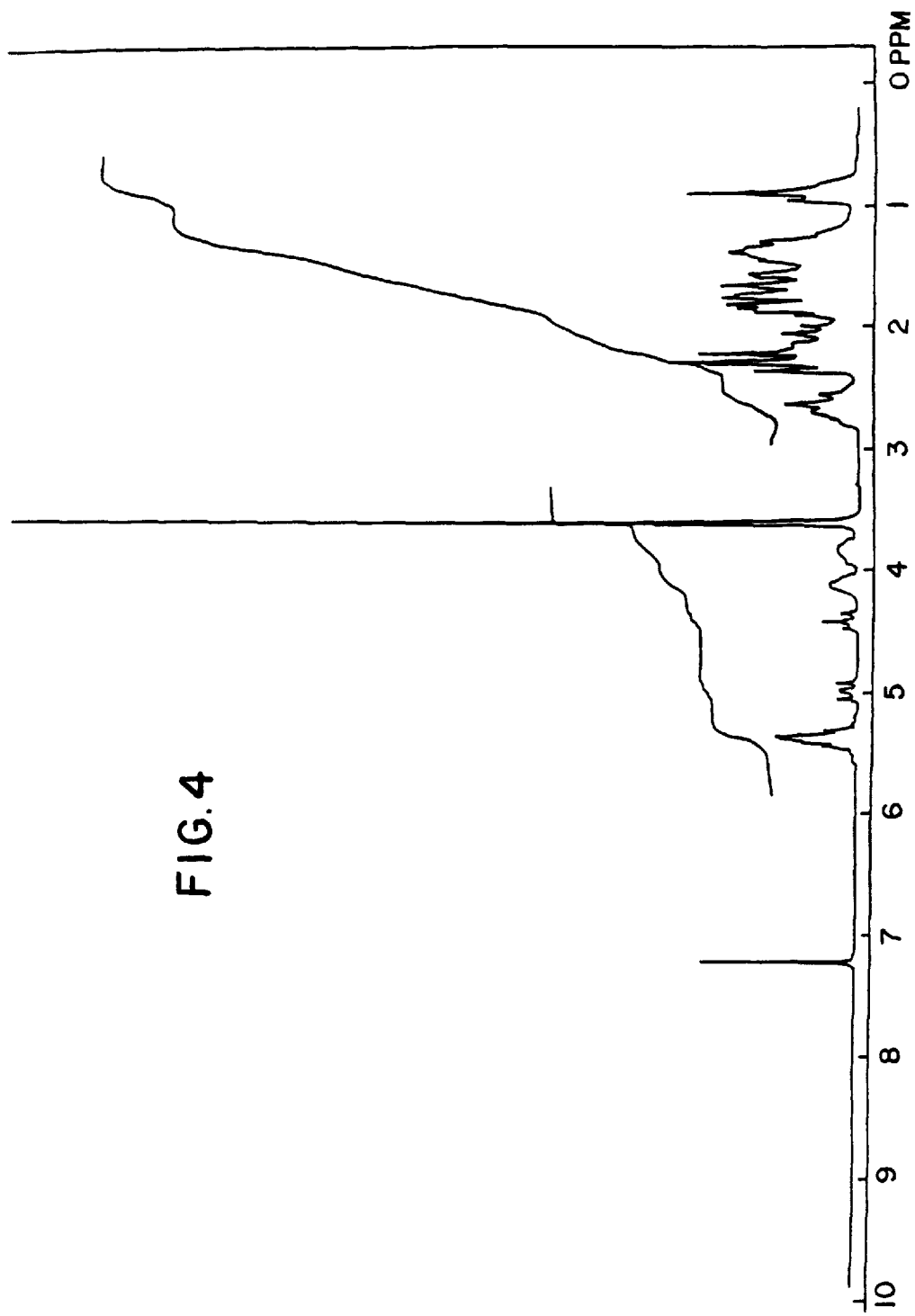

NMR spectrum of 13,1$^4$-dihydro-15-keto-16R,S-fluoro-$PGF_2\alpha$ methyl ester (26) is shown in FIG. 4. Mass (SIMS) m/z 387 (M$^+$+1), 349 (M$^+$+1−18)

EXAMPLE 6 (cf. Synthetic scheme III)

Synthesis of 13,14-dihydro-15-keto-16R,S-fluoro-11R-dehydroxy-11R-methyl-$PGF_2\alpha$ methyl ester (37):

(6-1) 15R,S-t-Butyldimethylsilyloxy-13,14-dihydro-16R,S-fluoro-$PGF_2\alpha$ methyl ester (29):

Lactone (18) (2.313 g) obtained according to Example 5 was reduced in toluene (25 ml) with using DIBAL-H (1.5-M, 15 ml) at −78° C. to give lactol (27) as a colorless oil.

Sodium hydride (60%, 1.84 g) washed with dry ether was suspended in anhydrous DMSO (20 ml), and kept at 70° C. for one hour to generate sodium methylsufinyl carbanion. A solution of (4-carboxybutyl)triphenylphosphonium bromide (10.19 g) in DMSO (30 ml) was added to the generated carbanion cooled at room temperature and stirred at room temperature for 10 minutes to yield ylide. To the ylide was added above lactol (27) in DNSO (50 ml) and stirred for 2.5 hours. The crude product obtained after the usual work-up was converted to the corresponding methyl ester with diazomethane, subsequently chromatographed (ethyl acetate/hexane=2/3–3/2) to give ester (29) as a colorless oil. Yield; 1.00 g (34%)

(6-2) Synthesis of 15R,S-t-butyldimethylsilyloxy-13,14-dihydro-16R,S-fluoro-11R-p-toluenesulfonyloxy-$PGF_2\alpha$ methyl ester (30):

15R,S-t-Butyldimethylsilyloxy-13,14-dihydro-16R,S-fluoro-$PG_2\alpha$ methyl ester (29) (0.430 g) was treated in anyhydrous pyridine (20 ml) with p-tlouenesulfonyl chloride (3.01 g) at room temperature for 2.5 hours. The crude product obtained after the usual work-up was chromatographed (ethyl acetate/hexane=1/3) to give the tosylate (30) as a colorless oil. Yield; 0.417 g (74%)

(6-3) 15R,S-t-Butyldimethylsilyloxy-13,14-dihydro-16R,S-fluoro-PGA methyl ester (31):

The tosylate (30) (0.417 g) was oxidized with Jones reagent (2.67-M, 0.9 ml) in acetone (25 ml) at −20° C. The crude product obtained after the usual work-up was chromatographed (ethyl acetate/hexane=1/5) to give a PGA derivative (31) as a colorless oil. Yield; 0.234 g (75%)

(6-4) Synthesis of 15R,S-t-butyldimethylsilyloxy-13,14-dihydro-16R,S-fluoro-11R-dehydroxy-11R-methyl-$PGE_2$ methyl ester (32):

Copper iodide (0.233 g) was suspended in anhydrous ether (30 ml), to which was added dropwise methyllithium (1.5-M, 1.56 ml) at −10° C. A solution of the enone (31) (0.281 g) in anyhydrous ether (20 ml) was added to the above mixture. After stirring at −10° C. for 40 minutes, acetic acid (0.6 ml) was added to stop the reaction. The crude product obtained after the usual work-up was chromatographed (ethyl acetate/hexane=1/7) to give a 11R-methyl compound (32) as a colorless oil. Yield; 0.192 g (66%)

(6-5) Synthesis of 15R,S-t-butyldimethylsilyloxy-13,14-dihydro-16R,S-fluoro-11R-dehydroxy-11R-methyl-PGF$_2\alpha$ methyl ester (33):

11R-Methyl-PGE$_2$ derivative (32) (0.234 g) was reduced in dry methanol (15 ml) with using sodium borohydride (0.178 g) at 0° C. The crude product obtained after the usual work-up was chromatographed (ethyl acetate/hexane=1/4) to give 9α-hydroxy derivative (33) as a colorless oil. Yield; 0.133 g (57%)

(6-6) 13,14-Dihydro-16R,S-fluoro-15-keto-11R-dehydroxy-11R-methyl-PGF$_2\alpha$ methyl ester (37):

9α-Hydroxy derivative (33) (0.302 g) was converted to the corresponding tetrahydropyranyl ether (34) according to the conventional manner. Yield; 0.352 g (100%)

11R-Methyl-PGF$_2\alpha$ derivative (34) (0.353 g) was converted to alcohol (35) with using tetrabutylammonium fluoride (1-M, 4 ml) in anhydrous THF (15 ml). Yield; 0.261 g (92%)

Alcohol (35) (0.261 g) was oxidized with Jones reagent (2.67-M, 0.5 ml) in acetone (15 ml) at −15° C. The crude product obtained after the usual work-up was chromatographed (ethyl acetate/hexane=1/7) to give ketone (36). Yield; 0.262 g (87%)

Ketone (36) (0.226 g) in a mixed solvent (acetic acid/water/THF=10/3.3/1) (20 ml) was kept at 45°–50° C. for 3 hours. The solvent was concentrated under reduced pressure and the resulting crude product was chromatographed (ethyl acetate/hexane=1/3 ) to give 13,14-dihydro-15-keto-16R,S-fluoro-11R-dehydroxy-11R-methyl-PGF$_2\alpha$ methyl ester (37). Yield; 0.171 g (92%)

Figure 5:
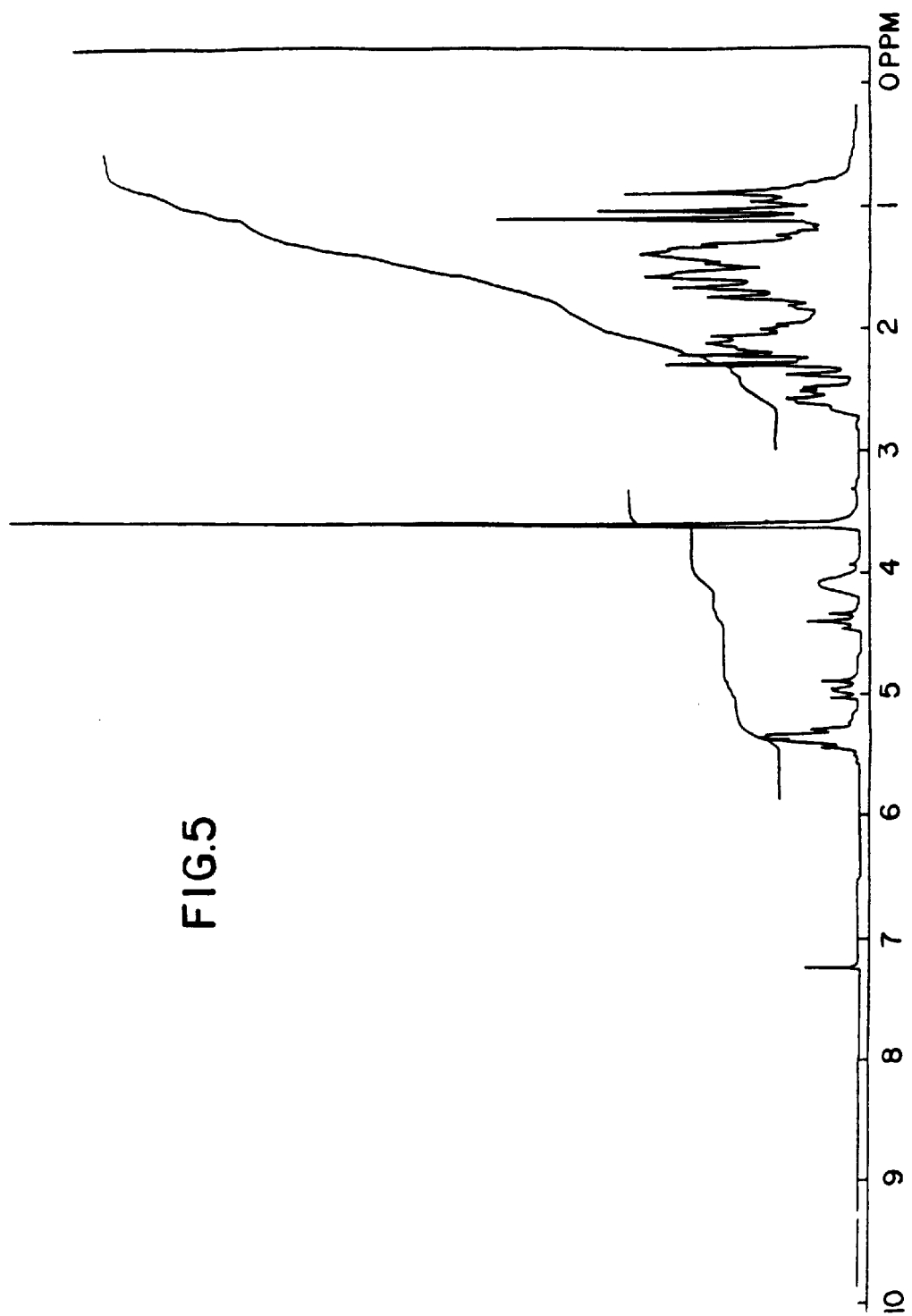

NMR spectrum of 13,14-dihydro-15-keto-16R,S-fluoro-11R-dehydroxy-11R-methyl-PGF$_2\alpha$ methyl ester (37) is shown in FIG. 5. Mass (SIMS) m/z 385 (m+1), 367 (M$^+$+1−18)

EXAMPLE 7 (cf. Synthetic scheme IV)

Synthesis of 13,14-dihydro-15-keto-20-ethyl-PGF$_2\alpha$ methyl ester (45); R=Me (7-1) 1S-2-oxa-3-oxo-6R-(3-oxo-1-trans-decenyl)-7R-(4-phenylbenzoyloxy)-cis-bicyclo(3,3,0)octane (38):

The solution of dimethyl (2-oxononyl)phosphonate (3.50 g) in dry THF (50 ml) was added dropwise to NaH (60%, 0.570 g) in THF (100 ml) and the reaction mixture was stirred for 40 minutes. A THF solution (60 ml) of aldehyde (2) obtained from (−)-Corey lactone (1) was added dropwise to the phosphonate anion in THF. After stirring overnight, acetic acid (5 ml) was added under ice-cooling and the compound (38) was obtained according to the conventional manner.

(7-2) Synthesis of 1S-2-oxa-3-oxo-6R-(3-oxo-1-decyl)-7R-(4-phenylbenzoyl)oxy-cis-bicyclo(3,3,0)octane (39):

Unsaturated ketone (38) was hydrogenated in ethyl acetate (150 ml) with using 5% palladium/carbon (0.120 g) to give the compound (39).

(7-3) Synthesis of 1S-2-oxa-3-oxo-6R-(3,3-ethylenedioxy-1-decyl)-7R-(4-phenylbenzoyl)oxy-cis-bicyclo(3,3,0)octane (40):

Saturated ketone (39), ethylene glycol (10 ml) and p-toluenesulfonic acid (catalytic amount) were dissolved in benzene (200 ml), and the solution was heated at reflux for 24 hours using a Dean-Stark Trap. After the usual work-up, the compound (40) was obtained. Yield; 3.90 g (53% basd on the compound (1))

(7-4) Synthesis of 1S-2-oxa-3-oxo-6R-(3,3-ethylenedioxy-1-decyl)-7R-hydroxy-cis-bicyclo(3,3,0)octane (41):

Ketal (40) (3.90 g) was dissolved in dry methanol (150 ml) and stirred with potassium carbonate (1.30 g) for 6 hours. Acetic acid (0.9 g) was added while cooling with ice. The crude product obtained after the usual work-up was chromatographed to give the compound (41). Yield; 2.18 g (85%)

(7-5) Synthesis of 20-ethyl-15,15-ethylenedioxy-13,14-dihydro-PGF$_2\alpha$ methyl ester (44):

Lactone (41) (1.22 g) was reduced in dry toluene (10 ml) with using DIBAL-H (7.6 ml) at −78° C. After stirring for 45 minutes, methanol (10 ml) was added and the mixture was stirred at room temperature for 30 minutes. The reaction solution was diluted with ether and filtered. The filtrate was concentrated under reduced pressure to give lactol (42).

Sodium hydride (60%, 1.15 g) washed with dry ether was suspended in DMSO (30 ml) and kept at 65°–70° C. for one hour to generate methylsulfinyl carbanion. A solution of (4-carboxybutyl)triphenylphosphonium bromide (6.4 g) in DMSO was added to the carbanion at room temperature to generate ylide, and the solution was stirred for 40 minutes. Lactol (42) in DMSO was added dropwise and the resultant was stirred overnight. The solution was poured into ice/water, the pH value was adjusted to 12 with aqueous potassium carbonate and the resultant was extracted with ethyl acetate. The aqueous layer was adjusted to pH 4 with diluted hydrochloric acid while cooling with ice and extracted with ether. The combined ether layers were dried and concentrated under reduced pressure to give the compound (43). The crude product (43) was converted into the corresponding methyl ester (44) with diazomethane, which was chromatographed. Yield; 1.29 g (82%)

(7-6) Synthesis of 13,14-dihydro-15-keto-20-ethyl-PGF$_2\alpha$ methyl ester (45):

Ketal (44) (1.06 g) was dissolved in a mixed solvent (acetic acid/water/THF=3/1/1) (18 ml) and kept at 50° C. for 3 hours. The solvent was distilled off and the resulting crude product was chromatographed to give 20-ethyl-13,14-dihydro-15-keto-20-ethyl-PGF$_2\alpha$ methyl ester (45). Yield; 0.868 g (74%)

Figure 6:
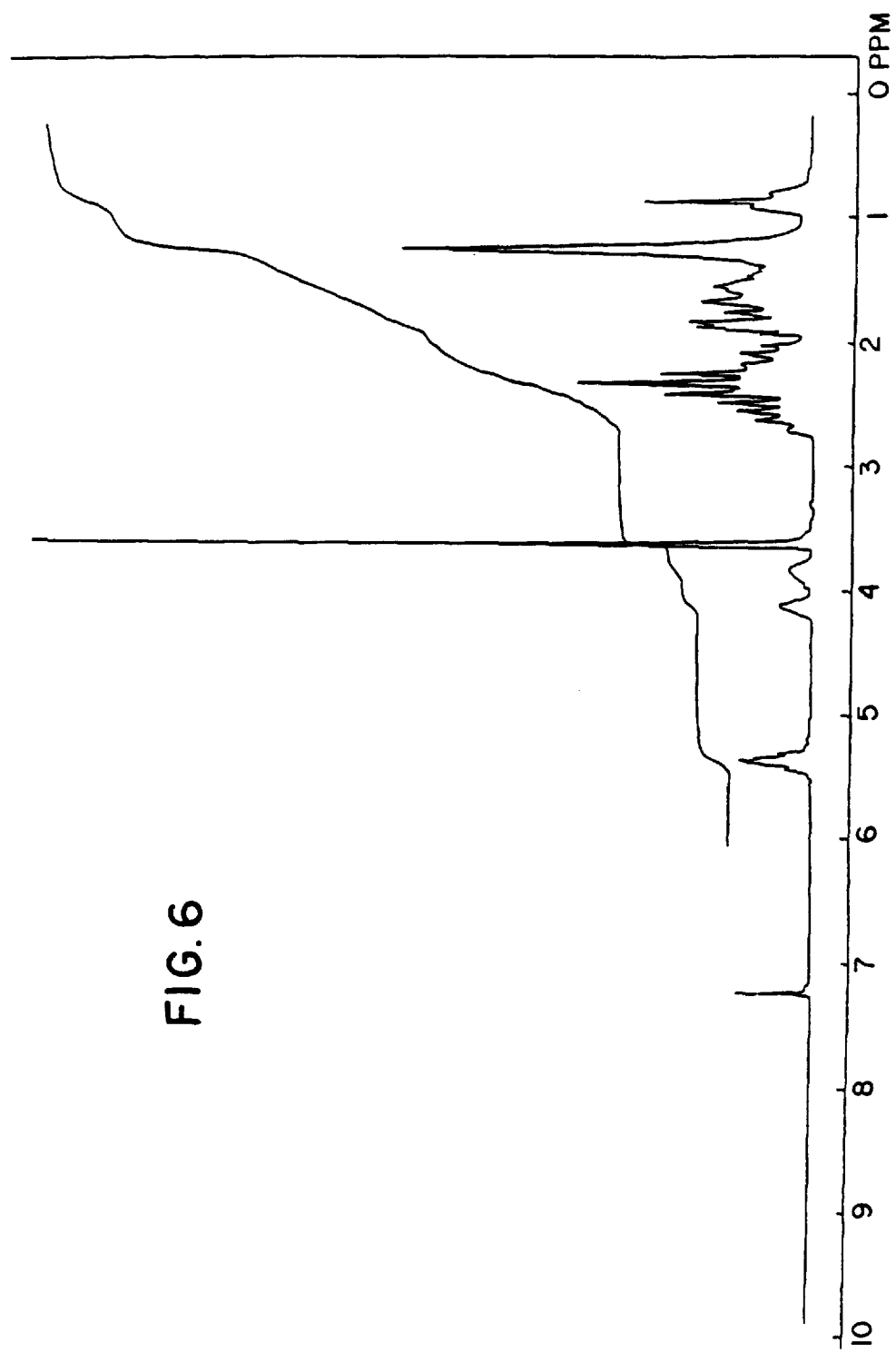

NMR spectrum of 13,14-dihydro-15-keto-20-ethyl-PGF$_2\alpha$ methyl ester (45) is shown in FIG. 6.

EXAMPLE 8

Synthesis of 13,14-dihydro-16,16-dimethyl-15-keto-PGF$_2\alpha$ ethyl ester (46):

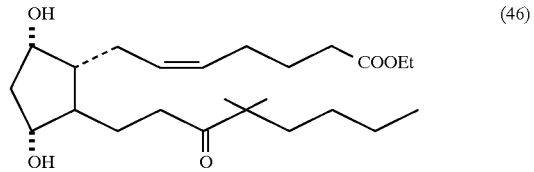

In the same manner as described in Examples 1 to 7 13,14-dihydro-15-keto-16,16-dimethyl-PGF$_2\alpha$ ethyl ester (46) was obtained with using (−)-Corey lactone (1) and dimethyl (3,3-dimethyl-2-oxoheptyl)phosphonate.

Figure 7:
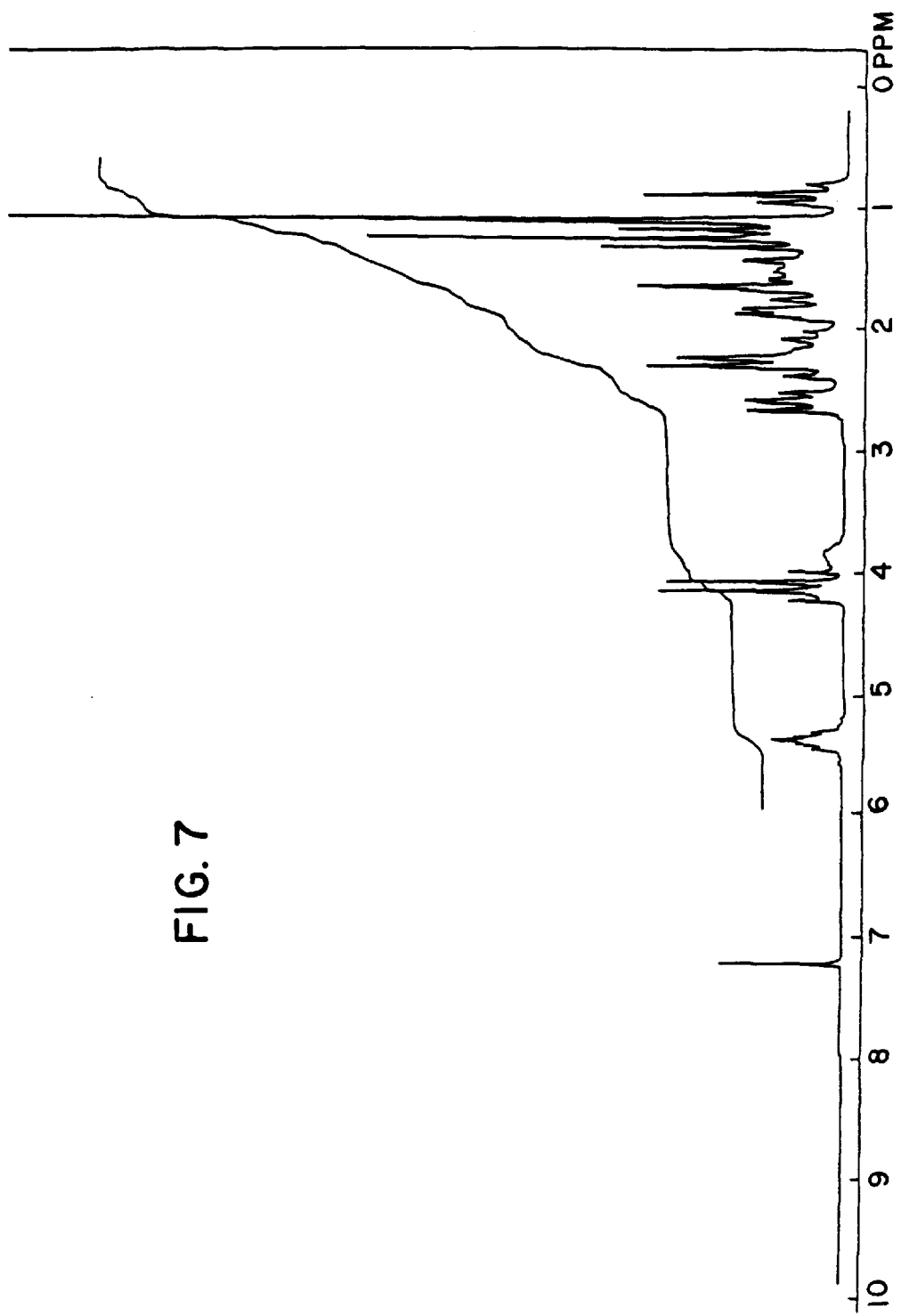

NMR spectrum of 13,14-dihydro-15-keto-16,16-dimethyl-PGF$_2\alpha$ ethyl ester (46) is shown in FIG. 7. Mass (DI) m/z 410, 392 (M$^+$-18), 374

EXAMPLE 9

Synthesis of 13,14-dihydro-15-keto-20-methoxy-PGF$_2\alpha$ methyl ester (47):

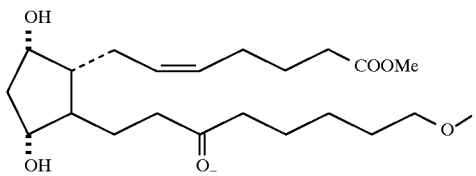
(47)

In the same manner as described in Example 1 to 8, 13,14-dihydro-15-keto-20-methoxy-PGF$_2\alpha$ methyl ester (47) was prepared with using (–)-Corey lactone (1) and dimethyl (7-methoxy-3-oxoheptyl)phosphonate.

Figure 8:
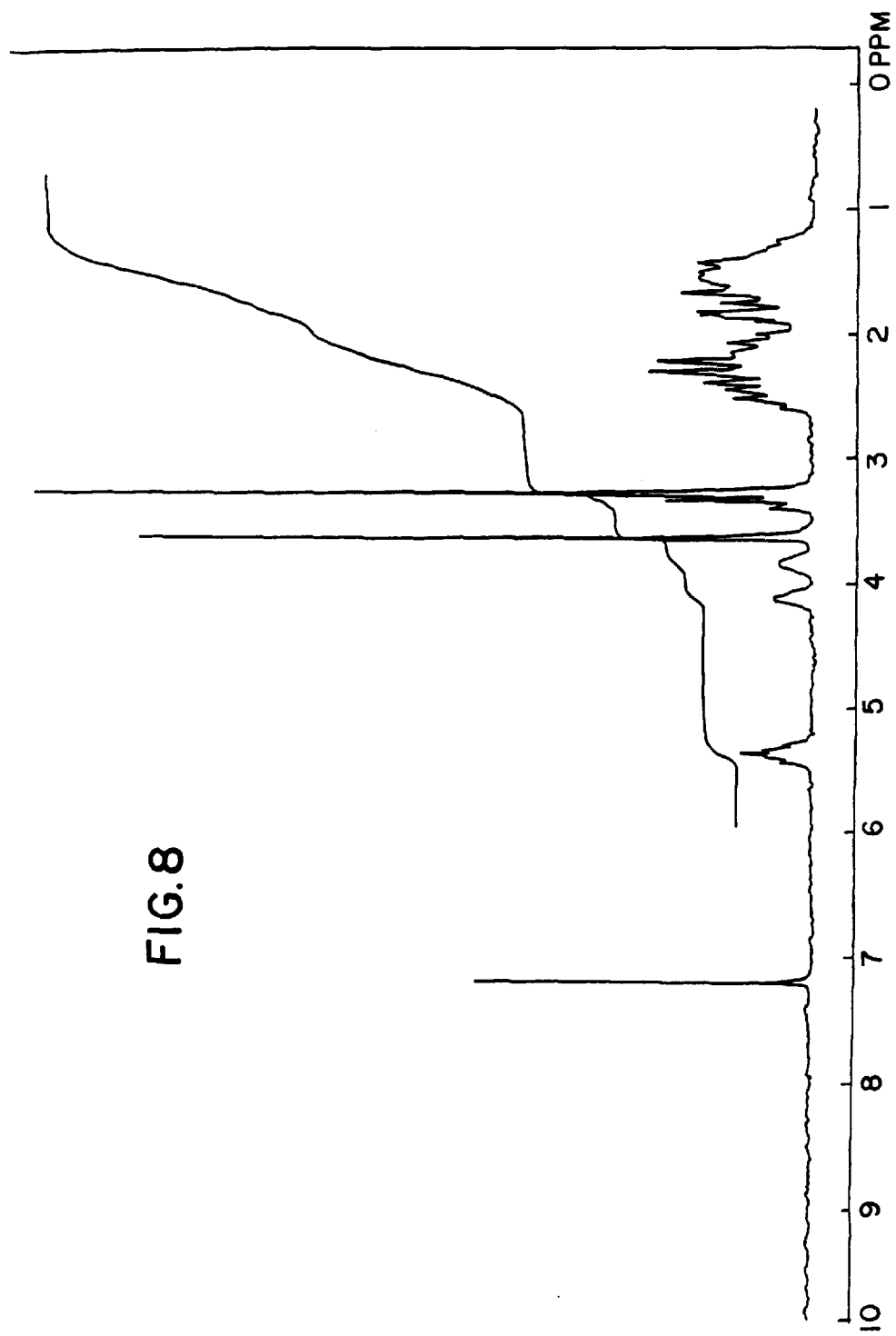

NMR spectrum of 13,14-dihydro-15-keto-20-methoxy-PGF$_2\alpha$ methyl ester (47) is shown in FIG. 8.

EXAMPLE 10

Synthesis of 13,14-dihydro-15-keto-17S-methyl-PGF$_2\alpha$ ethyl ester (101):

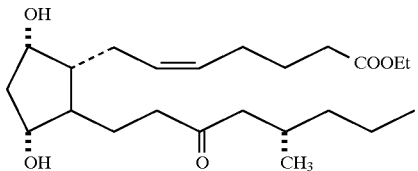
(101)

In the same manner as described in Example 1 to 9, 13,14-dihydro-15-keto-17S-methyl-PGF$_2\alpha$ ethyl ester (101) was prepared with using (–)-Corey lactone (1) and dimethyl (4S-methyl-2-oxoheptyl)phosphonate.

Figure 9:
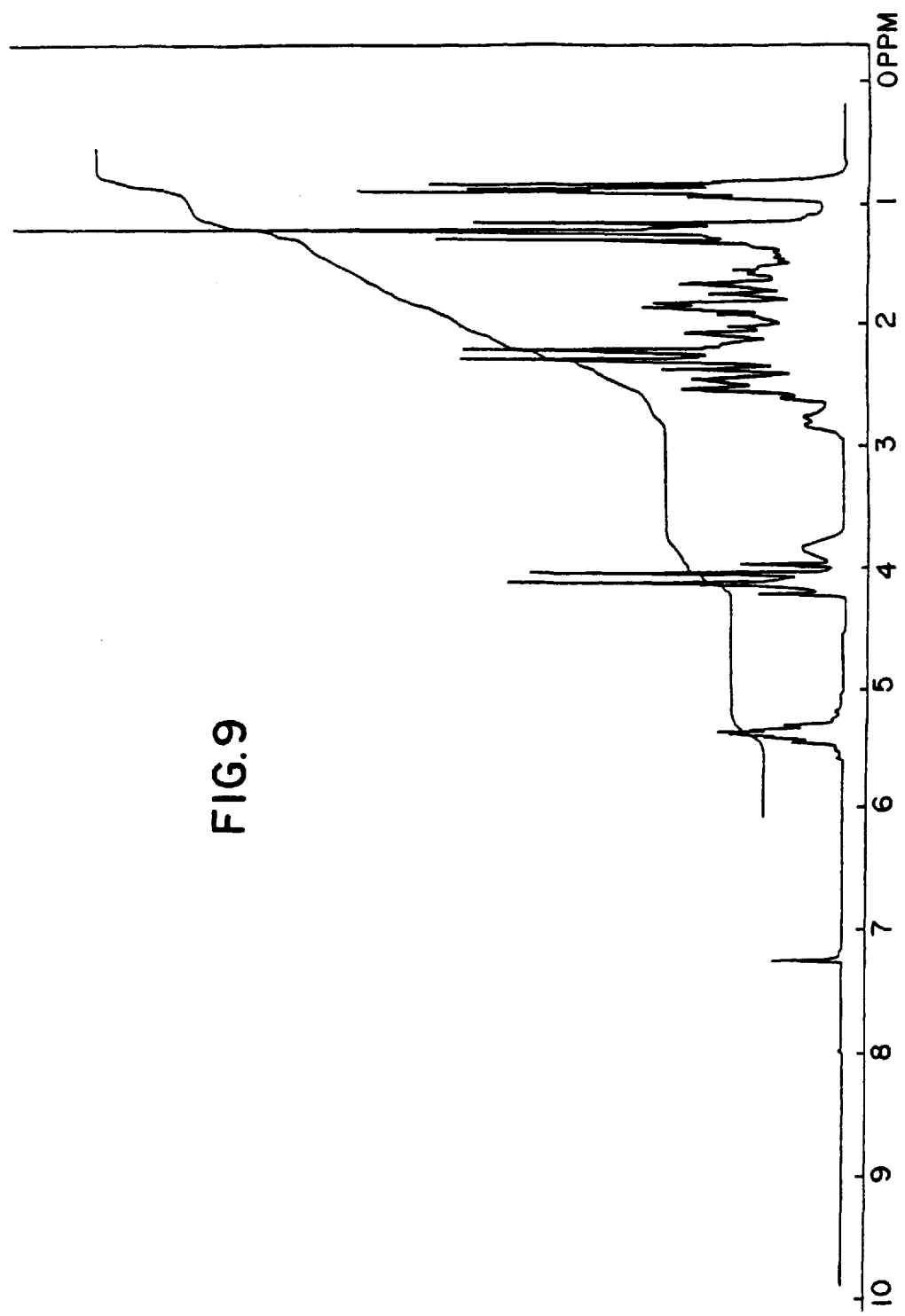

NMR spectrum of 13,14-dihydro-15-keto-17S-methyl-PGF$_2\alpha$ ethyl ester (101) is shown in FIG. 9. Mass (DI) m/z 396 (M$^+$), 378 (M$^+$-18), 360

EXAMPLE 11 (cf. Synthetic scheme IV)

Synthesis of 13,14-dihydro-15-keto-20-ethyl-PGF 2$\alpha$ ethyl ester (45); R=Et:

Procedure described in Example 7 was repeated to prepare 20-ethyl-13,14-dihydro-15-keto-PGF$_2\alpha$ ethyl ester (45), except that carboxylic acid (43) was converted into the corresponding ethyl ester (44) with using ethyl iodide and DBU in acetonitrile at 50° C.

Figure 10:
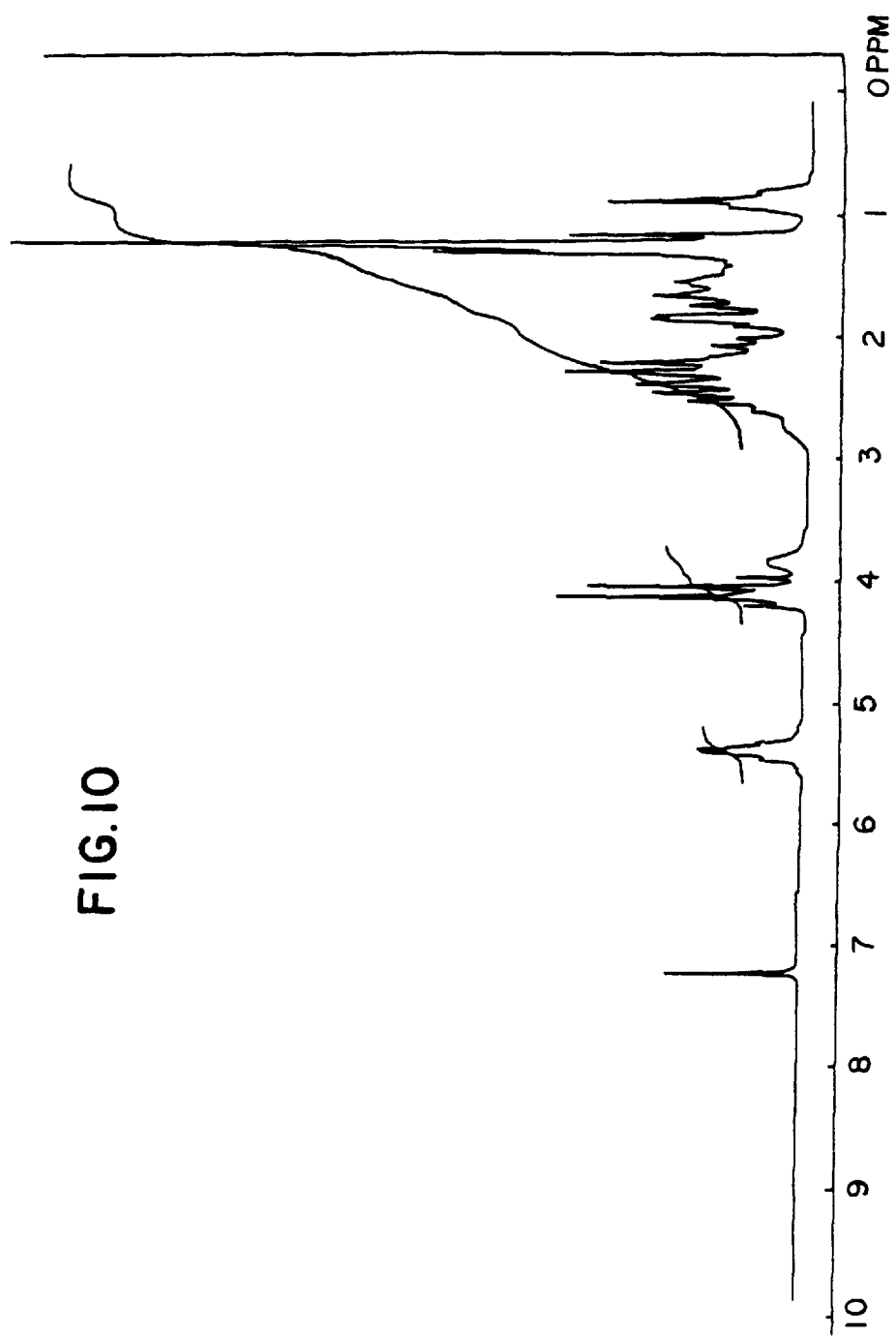

NMR spectrum of 13,14-dihydro-15-keto-20-ethyl-PGF$_2\alpha$ ethyl ester (45) is shown in FIG. 10. Mass (DI) m/z 410 (M$^+$), 392 (M$^+$-18), 374

EXAMPLE 12 (cf. Synthetic scheme IV)

Synthesis of 13,14-dihydro-15-keto-20-ethyl-PGF$_2\alpha$ isopropyl ester (45); R=iso-Pro Procedure described in Example 7 was repeated, exept that carboxylic acid (43) was converted into the corresponding isopropyl ester (44) with using isopropyl iodide and DBU in acetonitlile at 50° C. and 20-ethyl-13,14-dihydro-15-keto-PGF$_2\alpha$ isopropyl ester (45) was obtained.

Figure 11:
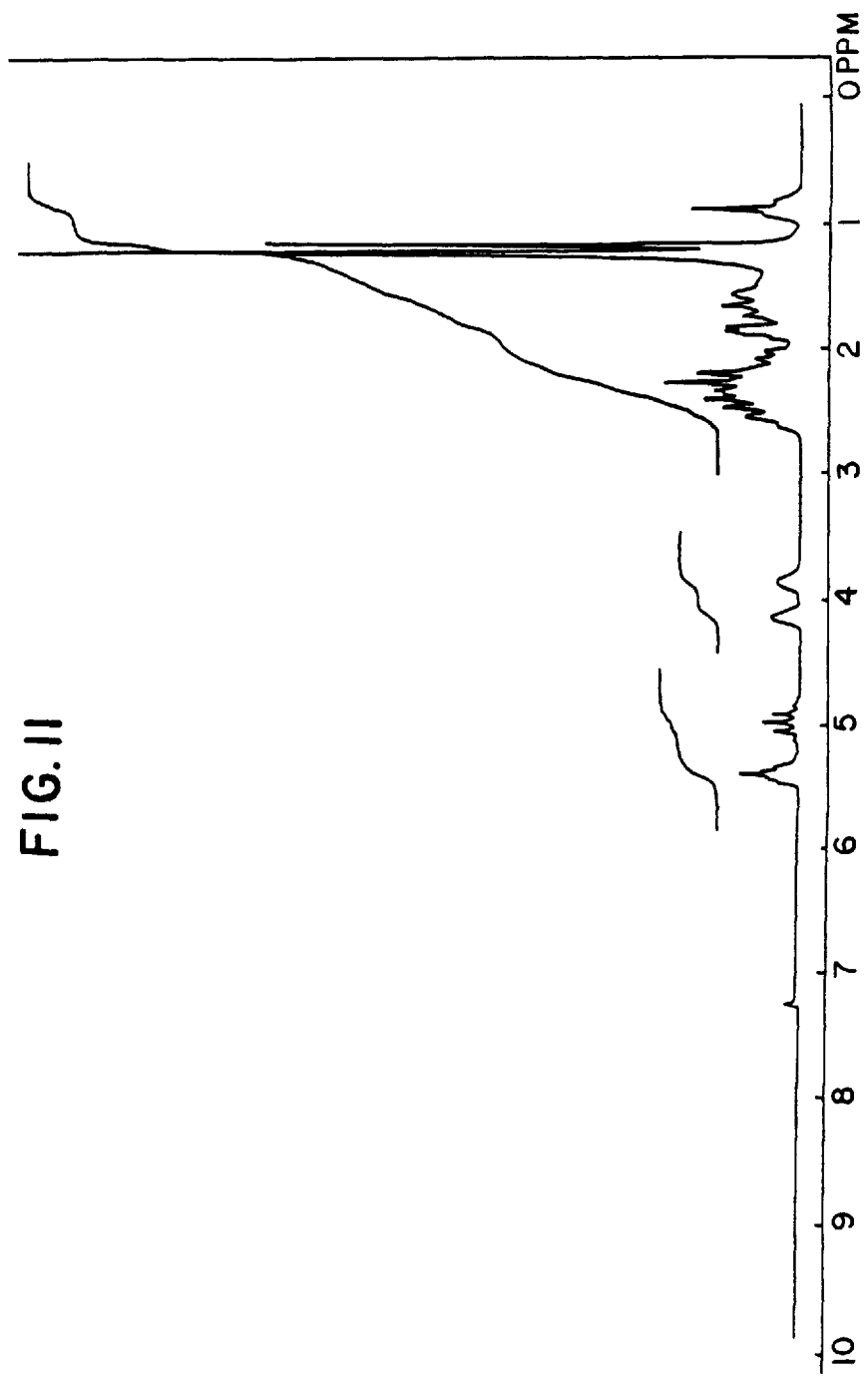

NMR spectrum of 13,14-dihydro-15-keto-20-ethyl-PGF$_2\alpha$ isopropyl ester (45) is shown in FIG. 11. Mass (DI) m/z 424 (M$^+$), 406 (M$^+$-18), 388, 347

EXAMPLE 13 (cf. Synthetic scheme IV)

Synthesis of 13,14-dihydro-15-keto-20-ethyl-PGF$_2\alpha$ n-butyl ester (45); R=n-Bu Procedure described in Example 7 was repeated to prepare 20-ethyl-13,14-dihydro-15-keto-PGF$_2\alpha$ n-butyl ester (45), excpt that carboxylic acid (43) was converted into the corresponding n-butyl ester (44) with using n-butyl iodide and DBU in acetonitrile at 50° C.

Figure 12:
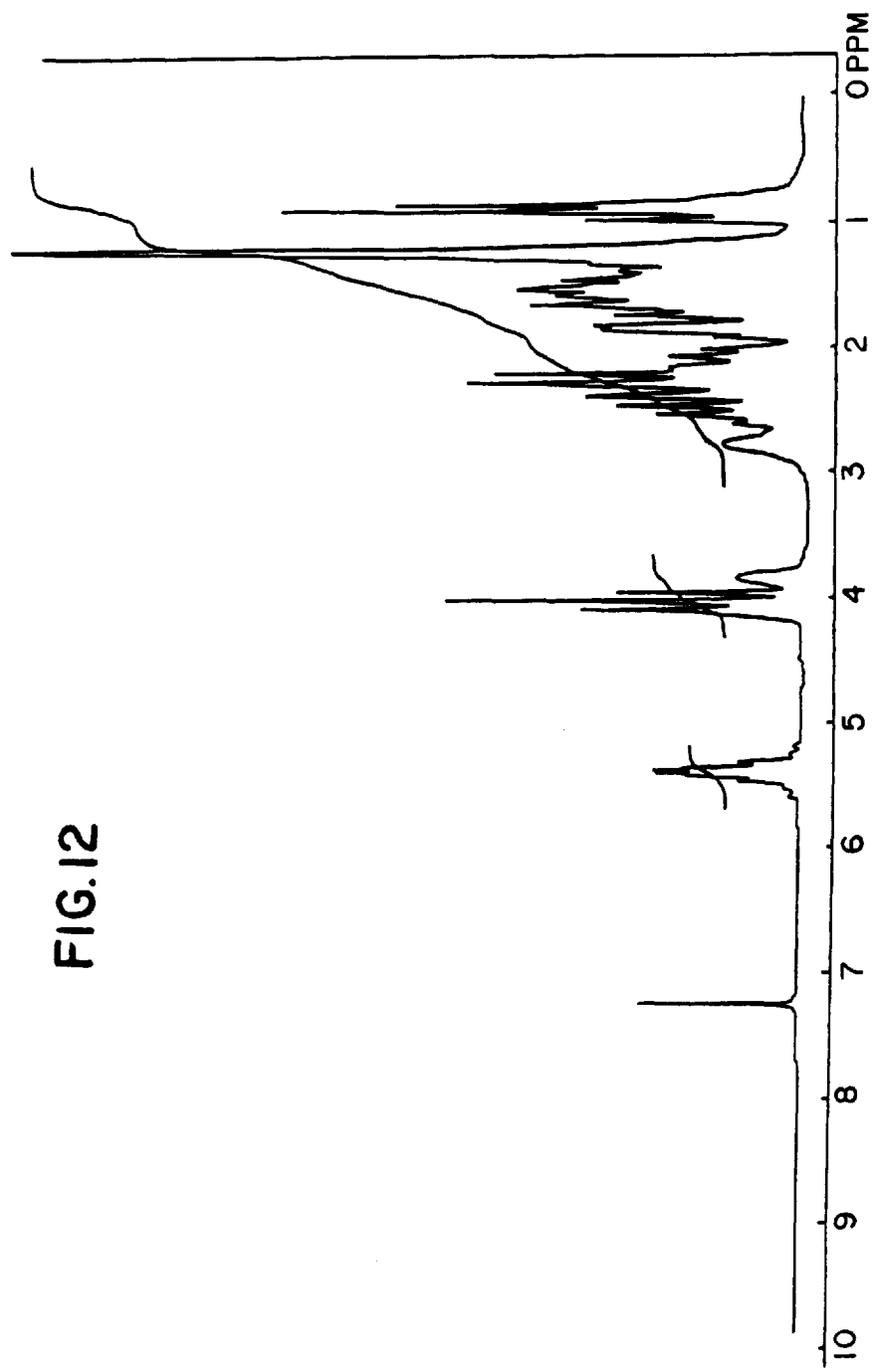

NMR spectrum of 13,14-dihydro-15-keto-20-ethyl-PGF$_2\alpha$ n-butyl ester (45) is shown in FIG. 12. Mass (DI) 420 (M$^+$), 402 (M$^+$-18), 376, 347

EXAMPLE 14 (cf. Synthetic scheme IV)

Synthesis of 13,14-dihydro-15-keto-20-ethyl-PGF$_1\alpha$ methyl ester (48)

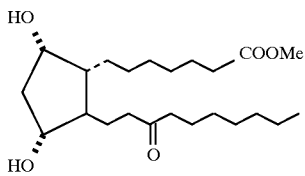
(48)

13,14-Dihydro-15-keto-20-ethyl-PGF$_2\alpha$ methyl ester (45); R=Me, (0.0505 g) was hydrogenated in ethanol with using PtO$_2$ to give 13,14-dihydro-15-keto-20-ethyl-PGF$_1\alpha$ methyl ester (48) (0.0166 g).

Figure 13:
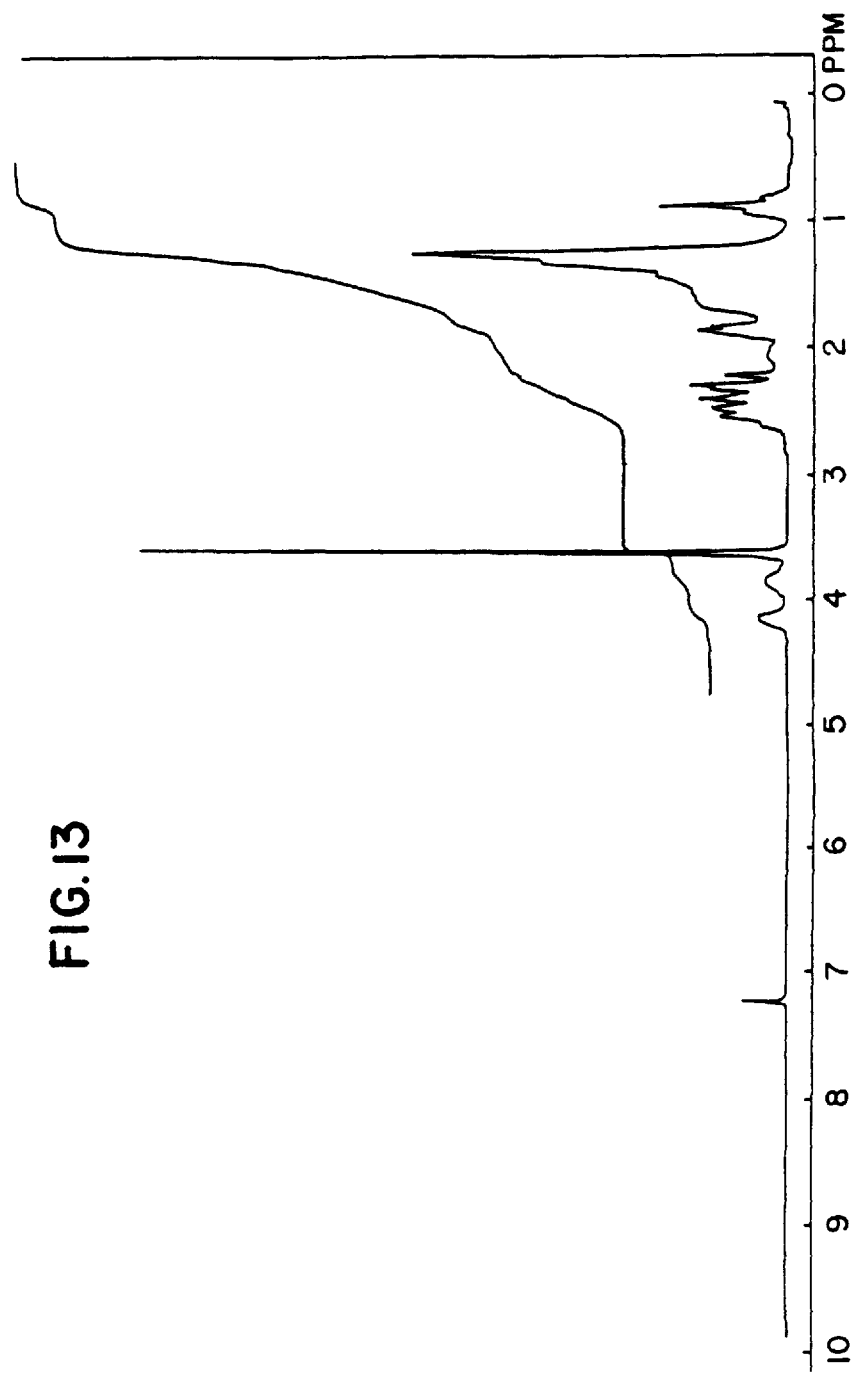

NMR spectrum of 20-ethyl-13,14-dihydro-15-keto-PGF$_1\alpha$ methyl ester (48) is shown in FIG. 13. Mass (DI) m/z 398 (M$^+$), 380 (M$^+$-18), 362, 349

EXAMPLE 15 (cf. Synthetic scheme V)

Synthesis of 13,14-dihydro-15-keto-20-ethyl-11R-dehydroxy-11R-methyl-PGF$_2\alpha$ methyl ester (57)

(15-1) Tosylation of 1S-2-oxa-3-oxo-6R-(3,3-ethylenedioxy-1-decyl)-7R-hydroxy-cis-bicyclo(3,3,0) octane (41); synthesis of tosylate (49):

Alcohol (41) (1.723 g) was treated with p-toluenesulfonyl chloride (2.893 g) in pyridine (5 ml) at 0° C. to give tosylate (49). Yield; 1.812 g (74%)

(15-2) Synthesis of 1S-2-oxa-3-oxo-6R-(3,3-ethylenedioxy-1-decyl)-cis-bicyclo(3,3,0)-7-octene (50):

Tosylate (49) (1.812 g) was dissolved into toluene (1.9 ml) and DBU (5.6 ml), and the solution was kept at 60° C. for 7 hours. The crude product obtained after the usual work-up was chromatographed (hexane/ethyl acetate=3/1) to give olefin (50). Yield, 0.7594 g (63%)

(15-3) Reduction of 1S-2-oxa-3-oxo-6R-(3,3-ethylenedioxy-1-decyl)-cis-bicyclo(3,3,0)-7-octene (50) with DIBAL-H; synthesis of lactol (51):

Olefin (50) (0.7594 g) was reduced with DIBAL-H (1.5-M, 6.2 ml) to give lactol (51).

(15-4) Synthesis of methyl 20-ethyl-15,15-ethylenedioxy-9S-hydroxy-cis$\Delta^5$-$\Delta^{10}$-prostanoate (53):

Lactol (51) was allowed to react with ylide obtained from (4-carboxybutyl)triphenylphosphonium bromide and sodium methylsulfinyl carbanion in DMSO to give prostanoic acid (52). The resultant was esterified with diazomethane to give the corresponding methyl prostanoate (53). Yield, 0.6600 g (67%)

(15-5) Synthesis of 13,14-dihydro-20-ethyl-15,15-ethylenedioxy-PGA, methyl ester (54):

Methyl prostanoate (53) (0.6600 g) was oxidized with Jones reagent in acetone (40 ml) at –20° C. After chromatography (hexane/ethyl acetate=3/1), 13,14-dihydro-20-ethyl-15,15-ethylenedioxy-PGA$_2$ methyl ester (54) was obtained. Yield, 0.6182 g (99%)

(15-6) Synthesis of 13,14-dihydro-20-ethyl-15,15-ethylenedioxy-11R-dehydroxy-11R-methyl-PGE$_2$ methyl ester (55):

Enone (54) (0.6100 g) was allowed to react with dimethylcopper complex obtained from copper iodide (0.8380 g) and methyllithium (1.5-M, 5.8 ml) in ether (15 ml) to give 13,14-dihydro-20-ethyl-15,15-ethylenedioxy-11R-dehydroxy-11R-methyl-PGE$_2$ methyl ester (55). Yield, 0,5720 g (94%)

Figure 14:
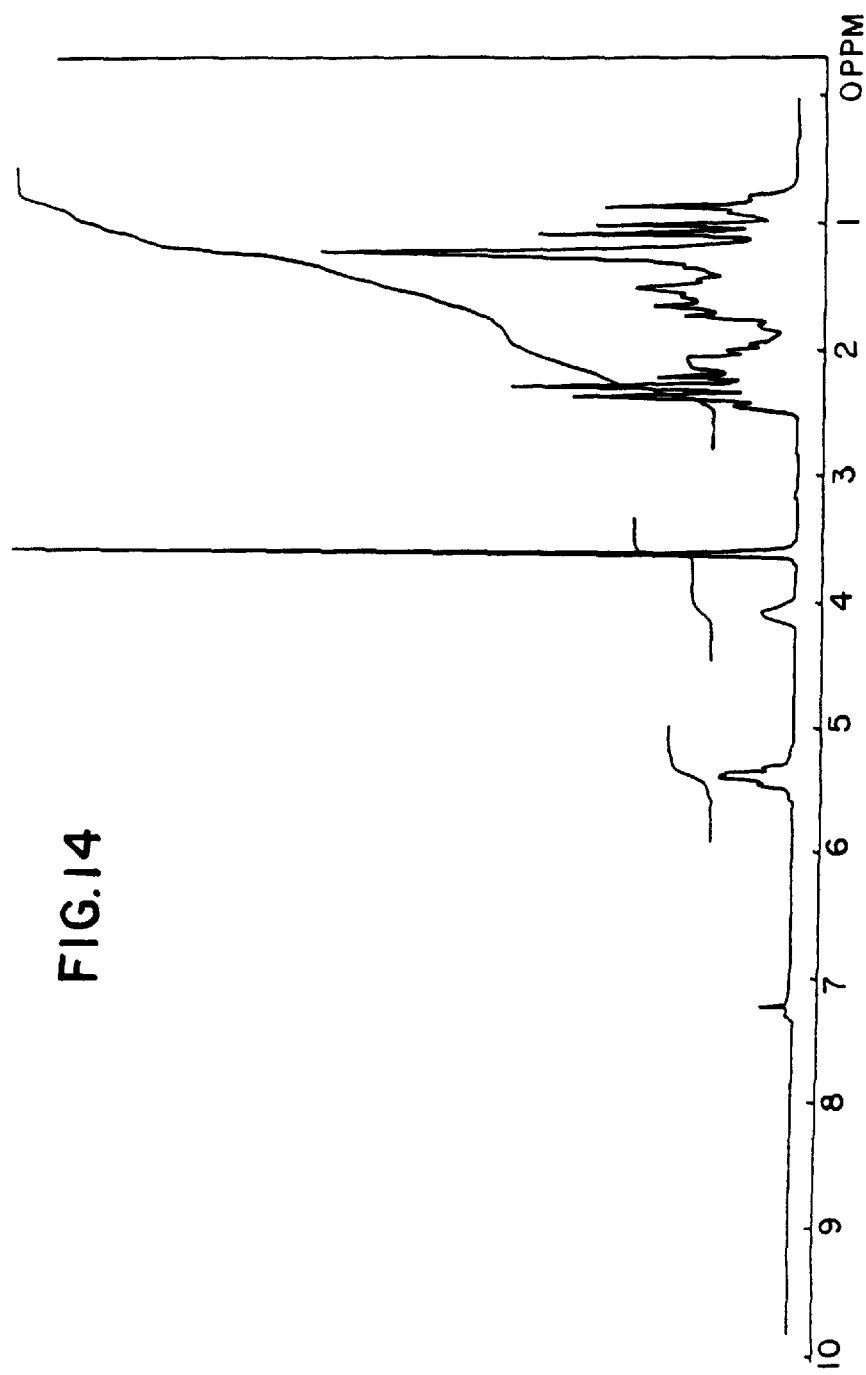

(15-7) Synthesis of 13,14-dihydro-15-keto-20-ethyl-11R-methyl-PGF$_2$α methyl ester (57):

Ketone (55) (0.4023 g) was reduced with diisobutylaluminium (2,6-di-tert-butyl-4-methyl)-phenoxide in toluene to give alcohol (56). Alcohol (56) (0.2016 g) was kept in a mixed solvent (acetic acid/water/THF=3/1/1) (20 ml) at 50° C. for one hour. After the usual procedure, 13,14-dihydro-15-keto-20-ethyl-11R-dehydroxy-11R-methyl-PGF$_2$α methyl ester (57) was obtained. Yield; 0.0960 g NMR spectrum of 13,14-dihydro-15-keto-20-ethyl-11R-dehydroxy-11R-methyl-PGF$_2$α methyl ester (57) is shown in FIG. 14. Mass 394 (DI) m/z 394 (M$^+$), 375 (M$^+$-18), 358, 344

EXAMPLE 16

Synthesis of 13,14-dihydro-15-keto-20-n-butyl-PGF$_2$α methyl ester (58)

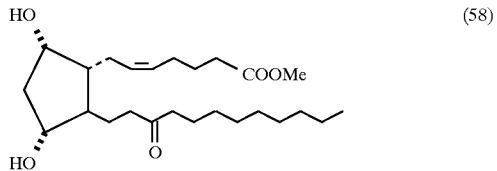

In the same manner as described in Examples 7 to 14, 13,14-dihydro-15-keto-20-n-butyl-PGF$_2$α methyl ester (58) was obtained with using dimethyl (2-oxoundecyl)phosphonate prepared in the same manner as preparation of dimethyl (2-oxononyl)phosphonate in Example 1 and (−)-Corey lactone.

Figure 15:
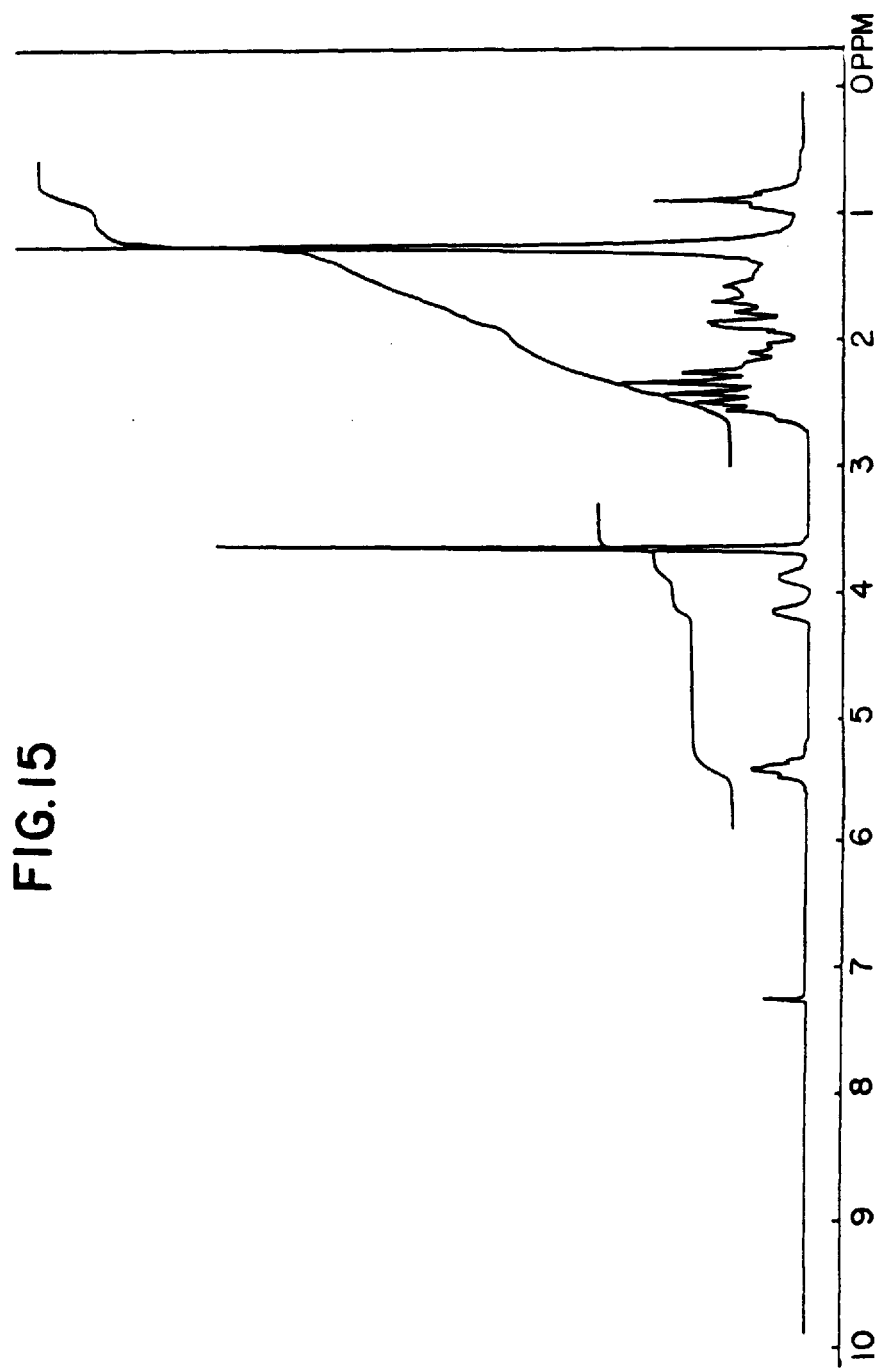

NMR spectrum of 13,14-dihydro-15-keto-20-n-butyl-PGF$_2$α methyl ester (58) is shown in FIG. 15. Mass (DI) m/z 424, (M$^+$), 406 (M$^+$-18), 388, 375

EXAMPLE 17

Synthesis of 13,14-dihydro-15-keto-20-methyl-PGF$_2$α methyl ester (59):

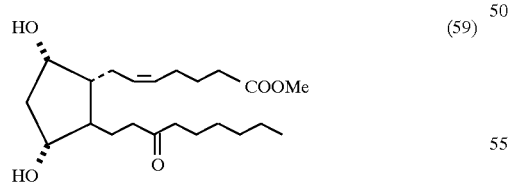

In the same manner as described in Examples 7 to 14 and 16, 13,14-dihydro-15-keto-20-methyl-PGF$_2$α methyl ester (59) was obtained with using dimethyl (2-oxooctyl)phosphonate prepared in the same manner as preparation of dimethyl (2-oxononyl)phosphonate in Example 1, and (−)-Corey lactone (1).

Figure 16:
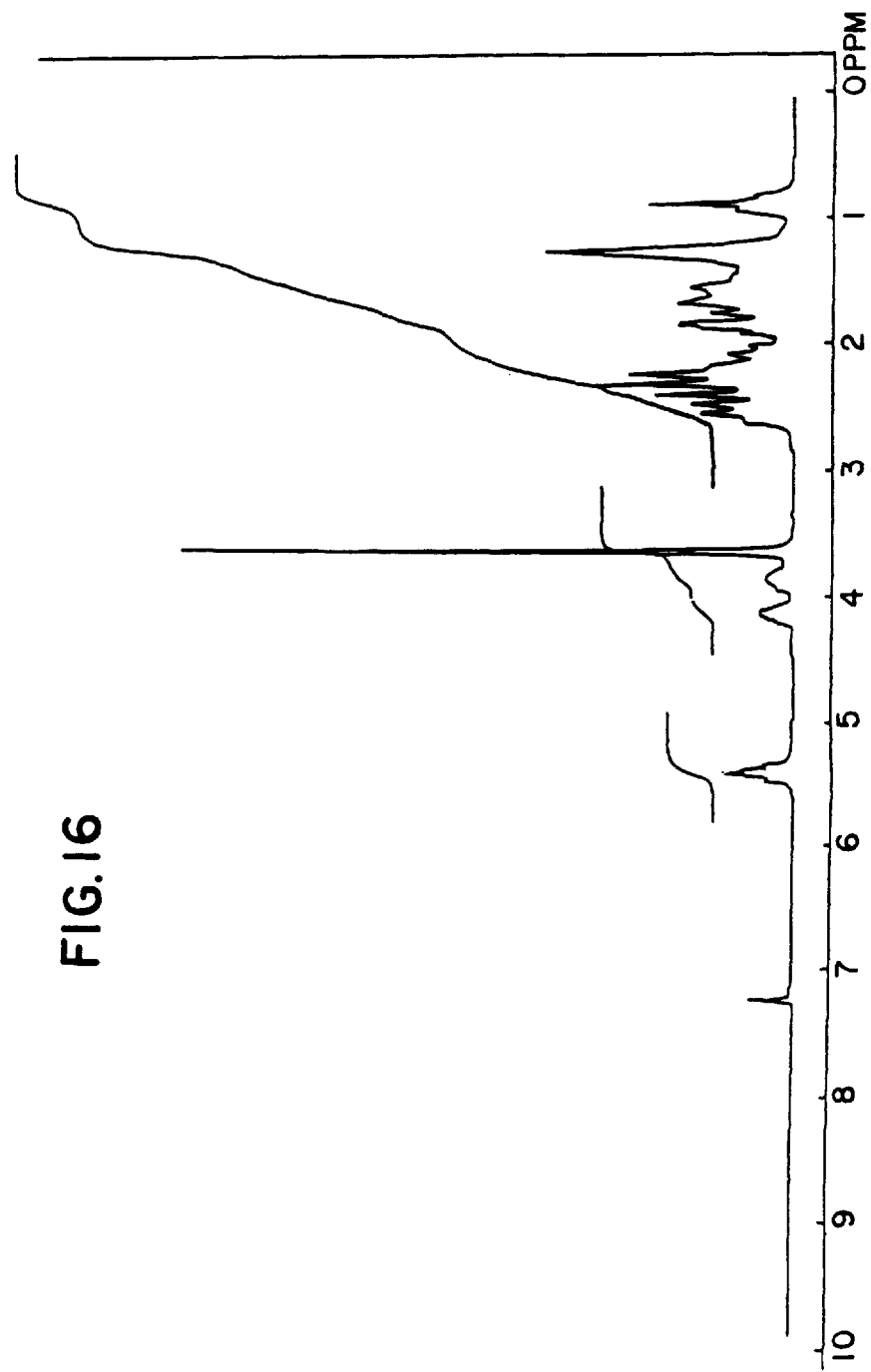

NMR spectrum of 13,14-dihydro-15-keto-20-methyl-PGF2α methyl ester (59) is shown in FIG. 16. Mass (SIMS) m/z 383 (M$^+$+1), 365 (M$^+$-18), 347

EXAMPLE 18

Synthesis of 13,14-dihydro-15-keto-20-ethyl-16R,S-fluoro-11R-dehydro-11R-methyl-PGF$_2$α methyl ester (60)

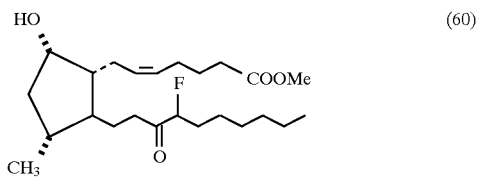

In the same manner as described in Example 6, 13,14-dihydro-15-keto-20-ethyl-16R,S-fluoro-11R-dehydroxy-11R-methyl-PGF$_2$α methyl ester (60) was obtained with using dimethyl (3R,S-fluoro-2-oxononyl)phosphonate prepared in the same manner as synthesis of dimethyl (3R,S-fluoro-2-oxoheptyl)phosphonate in Example 1, and (−)-Corey lactone.

Figure 17:
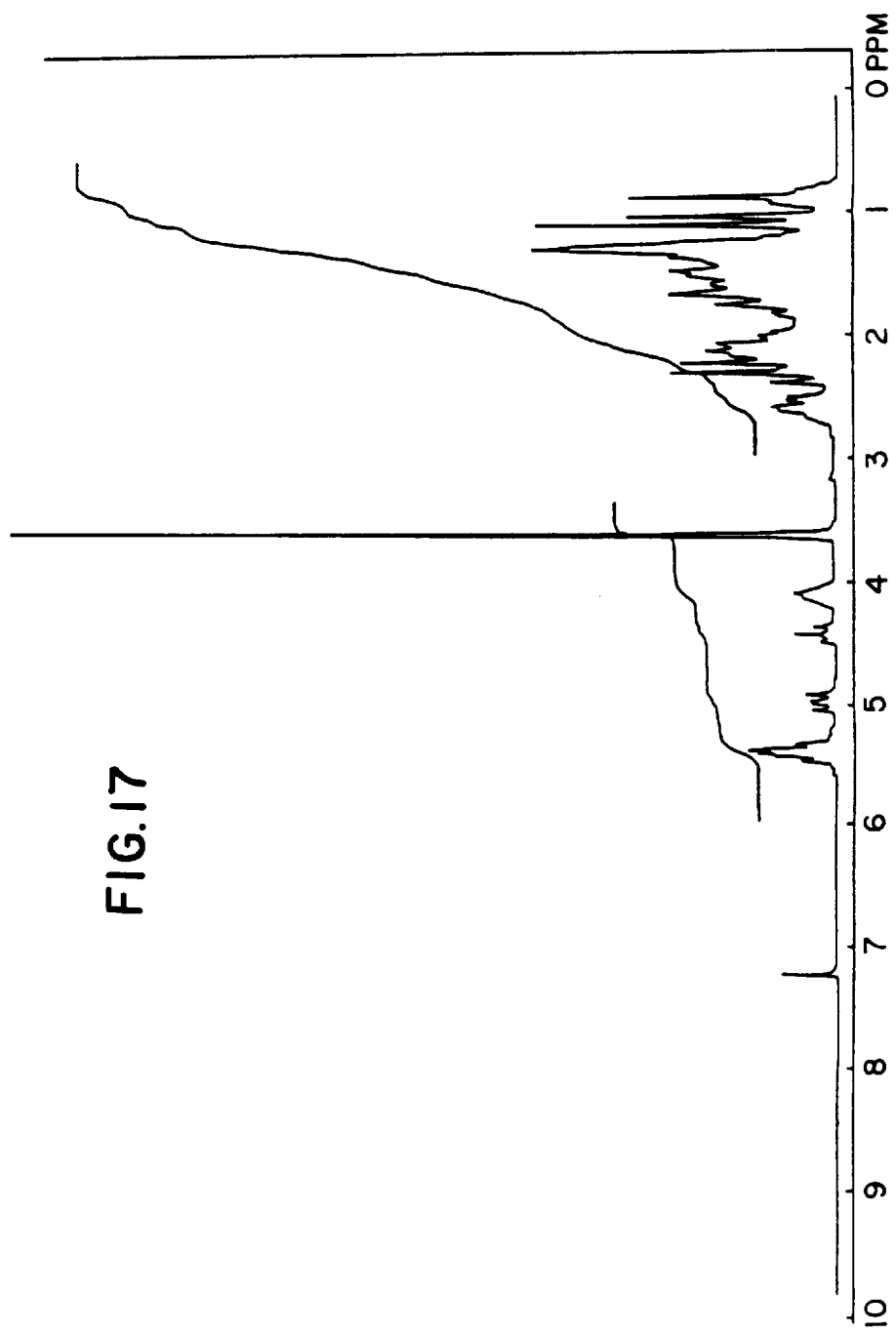

NMR spectrum of 13,14-dihydro-15-keto-20-ethyl-16R,S-fluoro-11R-dehydro-11R-methyl-PGF$_2$α methyl ester (60) is shown in FIG. 17. Mass (DI) m/z 412 (M$^+$), 394 (M$^+$-18)

EXAMPLE 19

Synthesis of 13,14-dihydro-15-keto-20-ethyl-16R,S-fluoro-PGF$_2$α methyl ester (61)

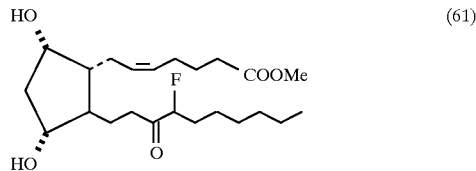

In the same manner as described in Example 5, 13,14-dihydro-15-keto-20-ethyl-16R,S-fluoro-PGF$_2$α methyl ester (61) was obtained with using dimethyl (3R,S-fluoro-2-oxononyl)phosphonate and (−)-Corey lactone.

Figure 18:
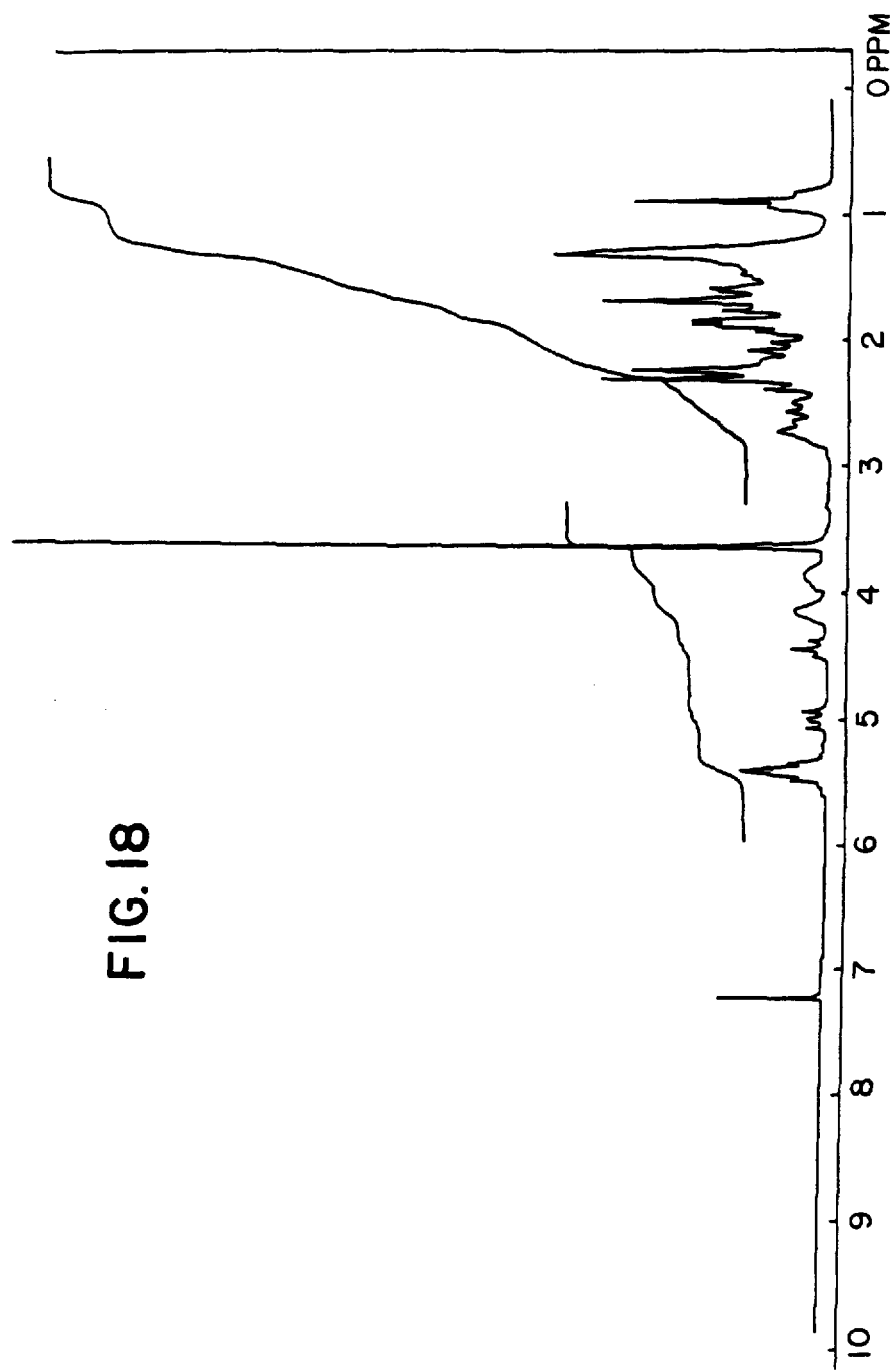

NMR spectrum of 13,14-dihydro-15-keto-20-ethyl-16R,S-fluoro-PGF$_2$α methyl ester is shown in FIG. 18.

Mass (DI) m/z 414 (M$^+$), 396(M$^+$-18), 378, 358

EXAMPLE 20 (cf. Synthetic scheme VI)

Synthesis of 13,14-dihydro-15-keto-9β,11α-PGF$_2$ methyl ester (64); R=CH$_3$

Figure 19:
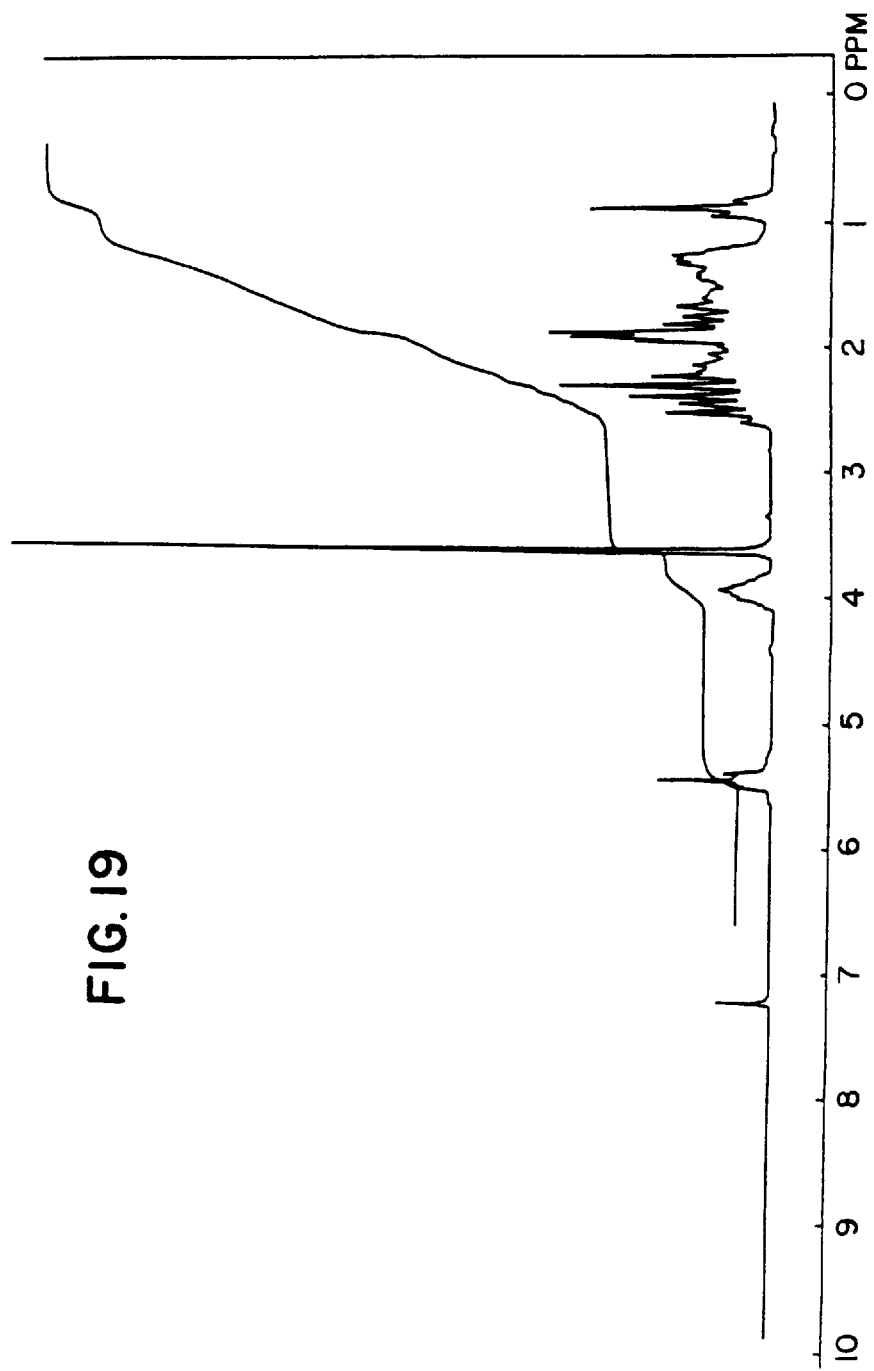

Alcohol (10) (0.2423 g) was converted into the corresponding benzoate (62) in dichloromethane (20 ml) with using diethyl azodicarboxylate (0.1026 g), benzoic acid (0.0720 g) and triphenylphosphine (0.1545 g). Yield; 0.1223 g The above benzoate (62) was treated with potassium carbonate in methanol to give 9β,11α-PGF derivative (63). The obtained 9β,11α-hydroxy-PGF derivative is deketalized to 13,14-dihydro-15-keto-9β,11α-PGF$_2$ methyl ester (64) Yield; 0.0236 g NMR spectrum of 13,14-dihydro-15-keto-9β,11α-hydroxy-PGF$_2$ methyl ester (64); R=CH$_3$, is shown in FIG. 19.

Mass (DI) m/z 368 (M$^+$), 350(M$^+$-18), 332, 319, 301

EXAMPLE 21

Synthesis of 13,14-dihydro-15-keto-20-n-propyl-PGF$_2\alpha$ methyl ester (65)

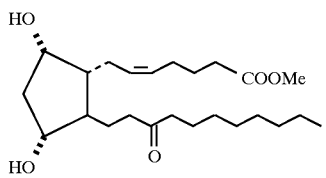
(65)

In the same manner as described in Examples 7 to 14, 16 and 17, 13,14-dihydro-15-keto-20-n-propyl-PGF$_2\alpha$ methyl ester (65) was prepared with using dimethyl (2-oxodecyl) phosphonate obtained in analogous to the synthesis of dimethyl (2-oxononyl)phosphonate in Example 1, and (−)-Corey lactone (1).

Figure 20:
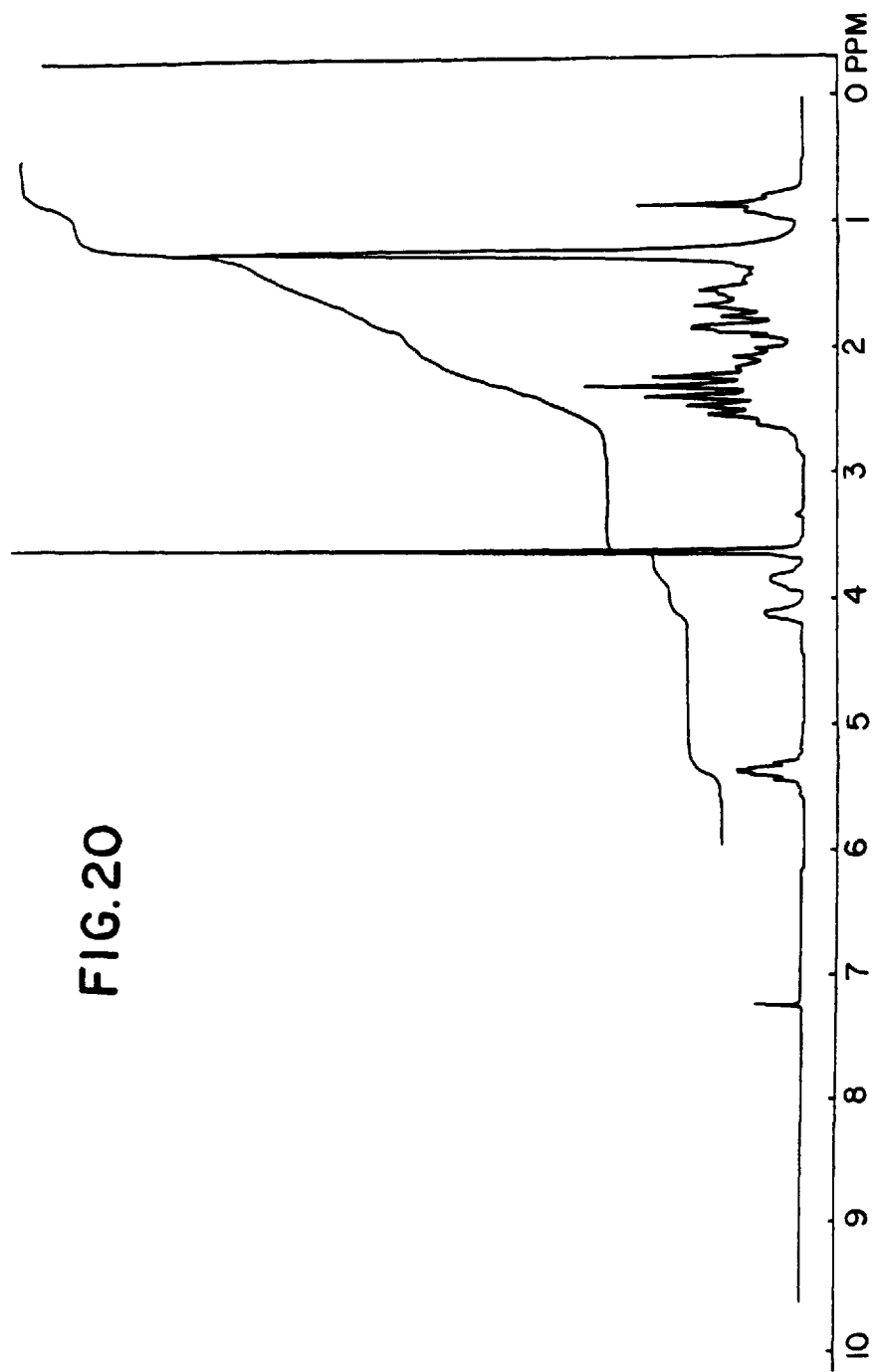

NMR spectrum of 13,14-dihydro-15-keto-20-n-propyl-PGF$_2\alpha$ methyl ester (65) is shown in FIG. 20.

EXAMPLE 22 (cf. Synthetic schemes II and VII)

Synthesis of 13,14-dihydro-15-keto-16R,S-fluoro-PGP$_2\alpha$ (68)

Figure 21:
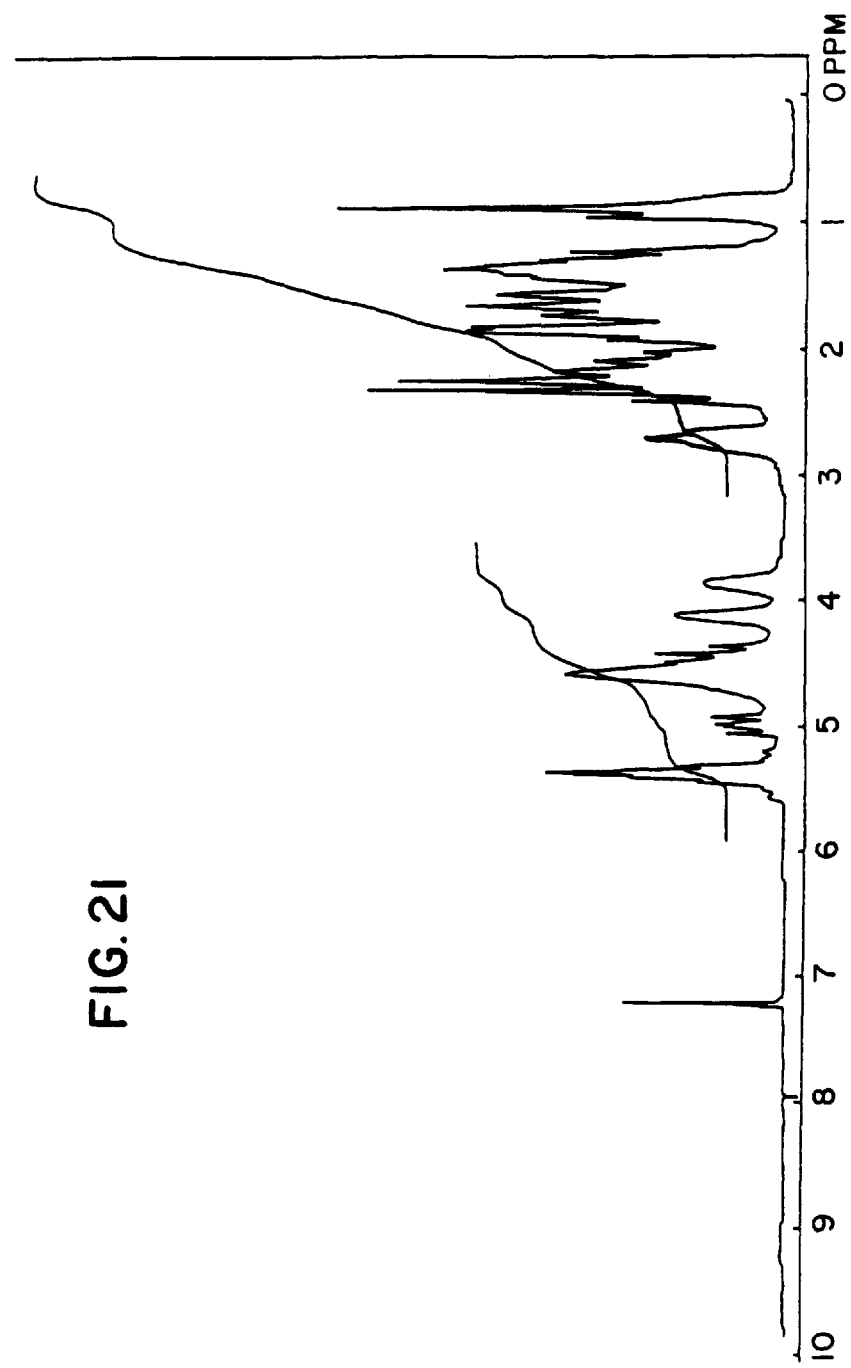

22-1) Synthesis of 13,14-dihydro-15-keto-16R,S-fluoro-9,11-bis(2-tetrapyranyloxy)-PGF$_2\alpha$ (67):

Ester (24) (0.796 g) was stirred overnight with lithium hydroxide (0.5 mol/100 ml) in THF (50 ml) at room temperature. After acidified with hydrochloric acid in an ice bath, the solution was extracted with ethyl acetate. The crude product (66) obtained after concentration under reduced pressure was oxidized with Jones reagent in acetone at −15° C. to give ketone (67). Yield; 0.330 g (22-2) Synthesis of 13,14-dihydro-15-keto-16R,S-fluoro-PGF$_2\alpha$ (68 ):

Ketone (67) (0.330 g) was kept in a mixed solvent (acetic acid/water/THF=4/2/1) (25 ml) at 45° C. for 3 hours. After the usual work-up, the product was chromatographed (ethyl acetate/hexane=1/3–2/3) to give 13,14-dihydro-15-keto-16R,S-fluoro-PGF$_2\alpha$ (68) as a pale yellow oil. Yield; 0.112 g NMR spectrum of 13,14-dihydro-15-keto-16R,S-fluoro-PGF$_2\alpha$ (68) is shown in FIG. 21. Mass (DI) m/z 372 (M$^+$), 354(M$^+$-18), 336, 284, 256

EXAMPLE 23 (cf. Synthetic scheme VII)

Synthesis of 13,14-dihydro-15-keto-20-ethyl-16R,S-fluoro-PGF$_2\alpha$ (69)

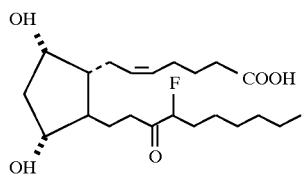
(69)

In the same manner as described in Example 22, 13,14-dihydro-15-keto-20-ethyl-16R,S-fluoro-PGF$_2\alpha$ (69) was prepared with using (−)-Corey lactone (1) and dimethyl (3R,S-fluoro-2-oxononyl)phosphonate obtained according to the conventional method.

Figure 22:
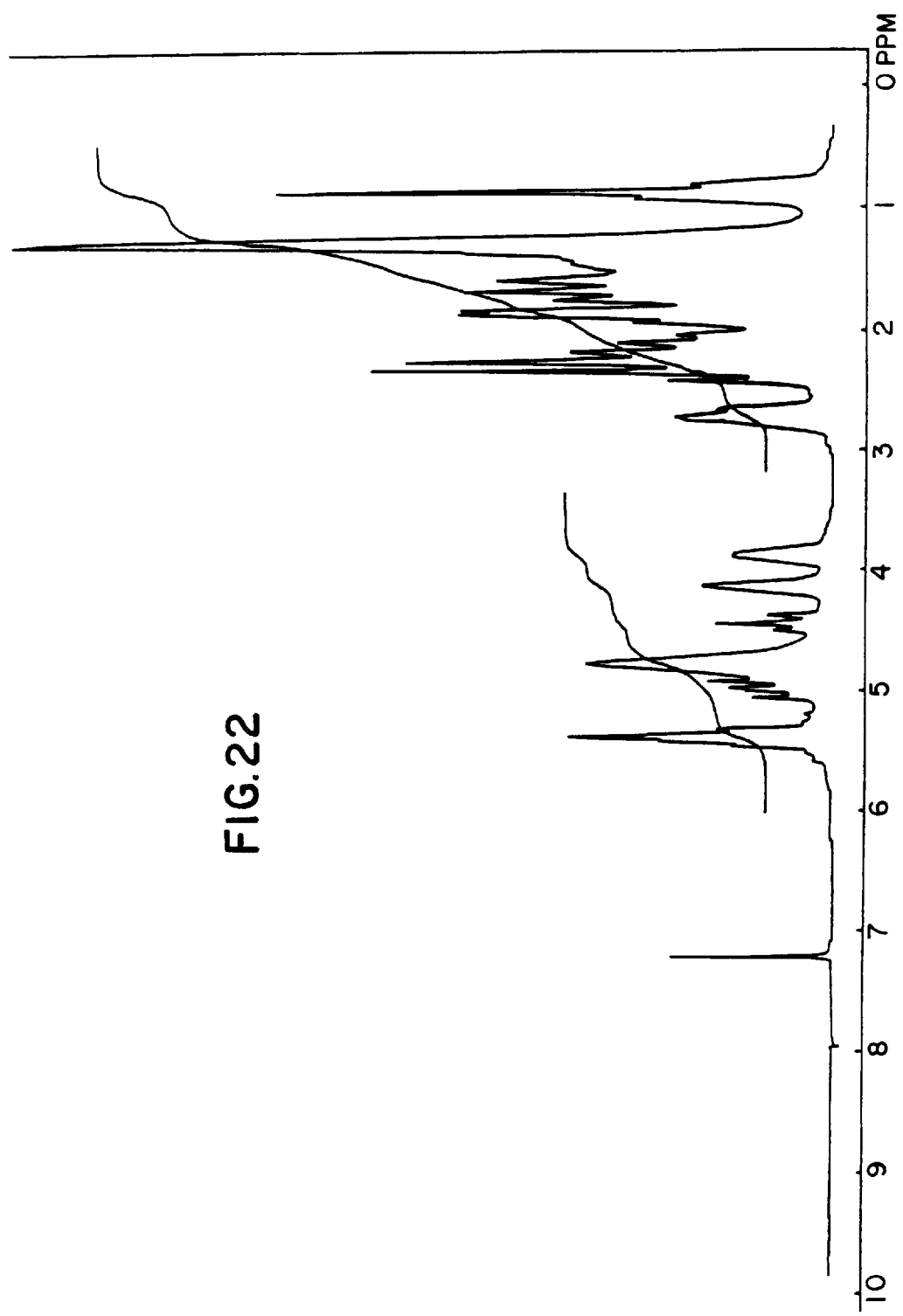

NMR spectrum of 13,14-dihydro-15-keto-20-ethyl- 16R,S-fluoro-PGF$_2\alpha$ (69) is shown in FIG. 22. Mass (DI) m/z 400 (M$^+$), 382 (M$^+$-18), 362, 344

EXAMPLE 24 (cf. Synthetic scheme IV)

Synthesis of 13,14-dihydro-15-keto-20-ethyl-PGF$_2\alpha$ (70)

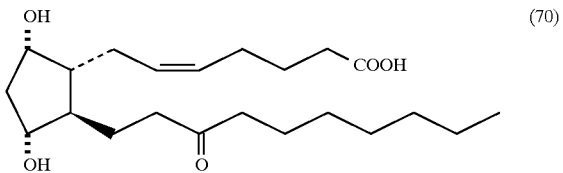
(70)

Figure 23:
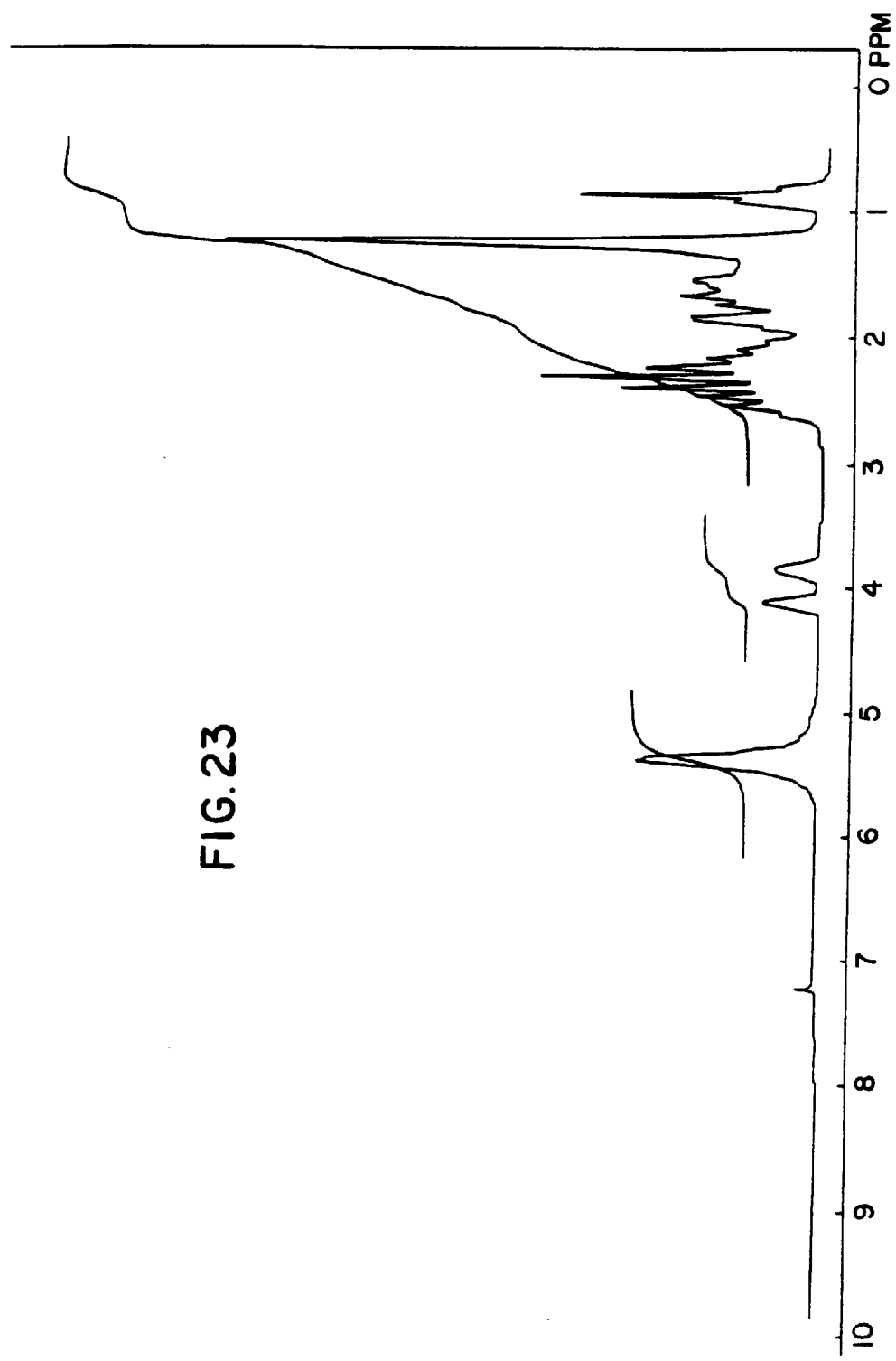

13,14-Dihydro-20-ethyl-15,15-ethylenedioxy PGF$_2\alpha$ (43)(0.518 g) was dissolved in a mixed solvent (acetic acid/THF/water=3/1/1) (10 ml) and held at 60° C. for 2 hours. After the usual work-up, the resulting crude product was chromatographed to give 13,14-dihydro-15-keto-20-ethyl-PGF$_2\alpha$ (70). Yield; 0.202 g NMR spectrum of 13,14-dihydro-15-keto-20-ethyl-PGF$_2\alpha$ (70) is shown in FIG. 23. Mass (DI) m/z 364 (M$^+$-18), 346

EXAMPLE 25 (cf. Synthetic scheme VIII)

Synthesis of 13,14-dihydro-15-keto-16-desbutyl-16-m-trifluoromethylphenoxy-PGF$_2\alpha$ methyl ester (82)

(25-1) Synthesis of 1S-2-oxa-3-oxo-6R-(4-m-trifluoromethylphenoxy-3-t-butyldimethylsilyloxy-1-butyl)-7R-hydroxy-cis-bicyclo(3,3,0)octane (75):

In the same manner as described in Example 5, alcohol (75) was obtained using unsaturated ketone (71) which was prepared with using (−)-Corey lactone (1) and dimethyl (3-m-trifluoromethylphenoxy-2-oxopropyl)-phosphonate obtained according to the usual method.

(25-2) Synthesis of 13,14-dihydro-15R,S-t-butyl-dimethylsilyloxy-9,11-bis(2-tetrapyranyl)oxy-16-desbutyl-16-m-trifluoromethylphenoxy-PGF$_2\alpha$ methyl ester (79):

13,14-Dihydro-15R,S-t-butyldimethylsilyloxy-16-desbutyl-16-m-trifluoromethylphenoxy-PGF$_2\alpha$ methyl ester (78) (0.50 g) obtained from alcohol (75) according to the usual method was converted into the compound (79) in dichloromethane (50 ml) using dihydropyran (1.5 ml) and catalytic amount of p-toluenesulfonic acid.

(25-3) Synthesis of 13,14-dihydro-15R,S-hydroxy-9,11-bis(2-tetrapyranyl)oxy-16-desbutyl-16-m-trifluoromethylphenoxy PGF$_2\alpha$ methyl ester (80):

The above compound (79) was converted into the compound (80) using tetrabutylammonium fluoride in TEF (10 ml). Yield; 0.42 g (77%)

(25-4) Synthesis of 13,14-dihydro-15-keto-9,11-bis(2-tetrapyranyl)oxy-16-desbutyl-16-m-trifluoromethylphenoxy-PGF$_2\alpha$ methyl ester (81):

The compound (80) (0.42 g) was oxidized with Jones reagent in acetone (15 ml) at −35° C. to give ketone (81). Yield; 0.18 g (43%)

(25-5) Synthesis of 13,14-dihydro-15-keto-16-desbutyl-16-m-trifluoromethylphenoxy-PGF$_2\alpha$ methyl ester (82):

The compound (81) (0.18 g) was dissolved in a mixed solvent (acetic acid/THF/water=3/1/1) (15 ml) and kept at 50° C. for 2 hours. The crude product obtained after the usual work-up was chromatographed to give 13,14-dihydro-15-keto-16-desbutyl-16-m-trifluoromethylphenoxy-PGF$_2\alpha$ methyl ester (82). Yield; 0.123 g (93%)

Figure 24:
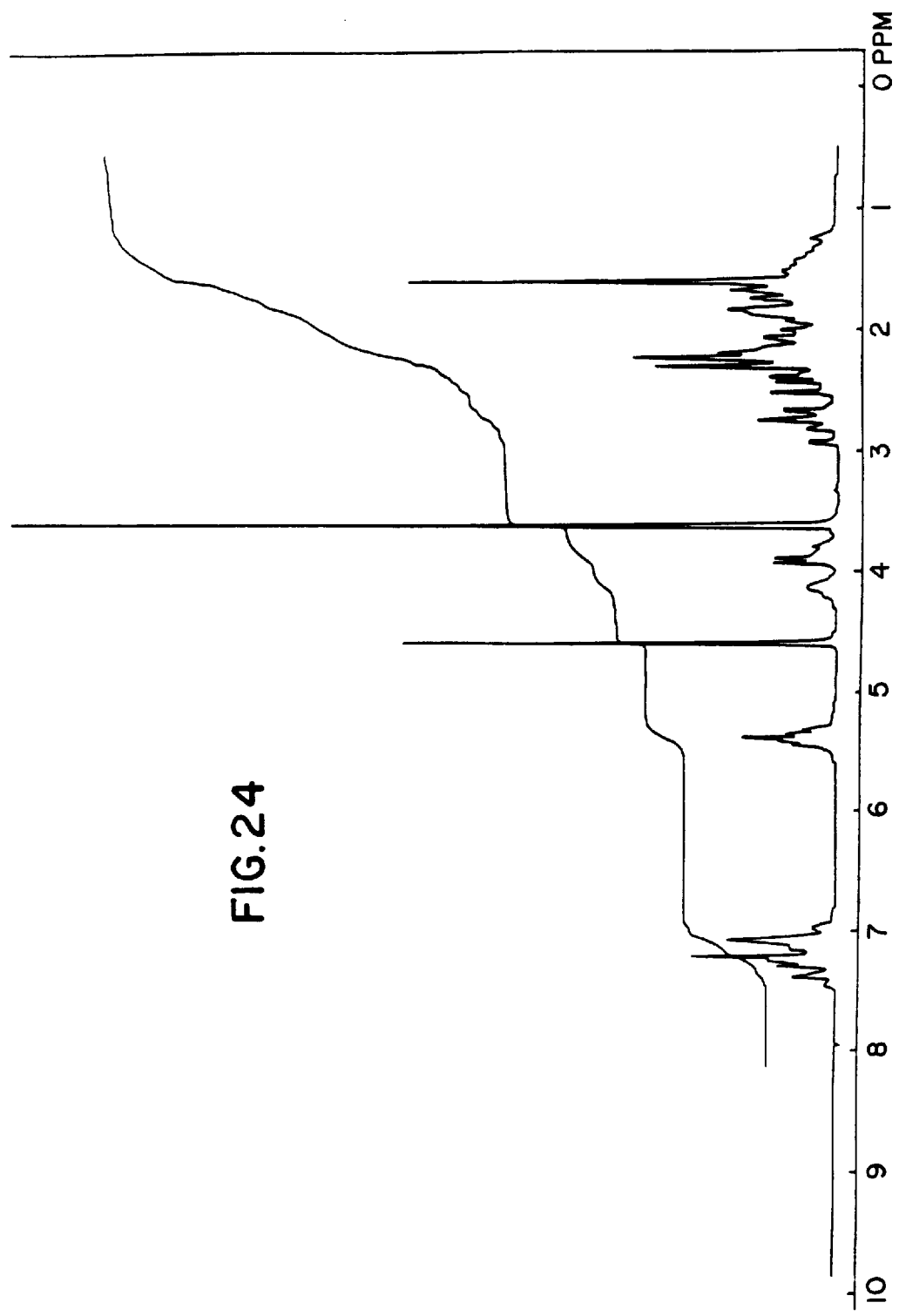

NMR spectrum of 13,14-dihydro-15-keto-16-desbutyl-16-m-trifluoromethylphenoxy-PGF$_2\alpha$ methyl ester is shown in FIG. 24. Mass (DI) m/z 472, 454, 436, 423

EXAMPLE 26

Synthesis of 13,14-dihydro-15-keto-16R,S-fluoro-20-methyl-PGF$_2\alpha$ methyl ester (83):

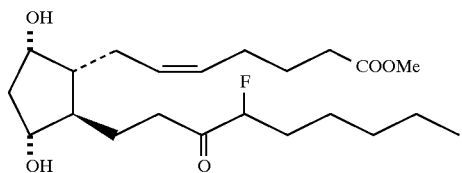

In the same manner as described in Example 5, 13,14-dihydro-15-keto-16R,S-fluoro-20-methyl-PGF$_2\alpha$ methyl ester (83) was obtained with using (−)-Corey lactone (1) and dimethyl (3R,S-fluoro-2-oxooctyl)phosphonate.

Figure 25:
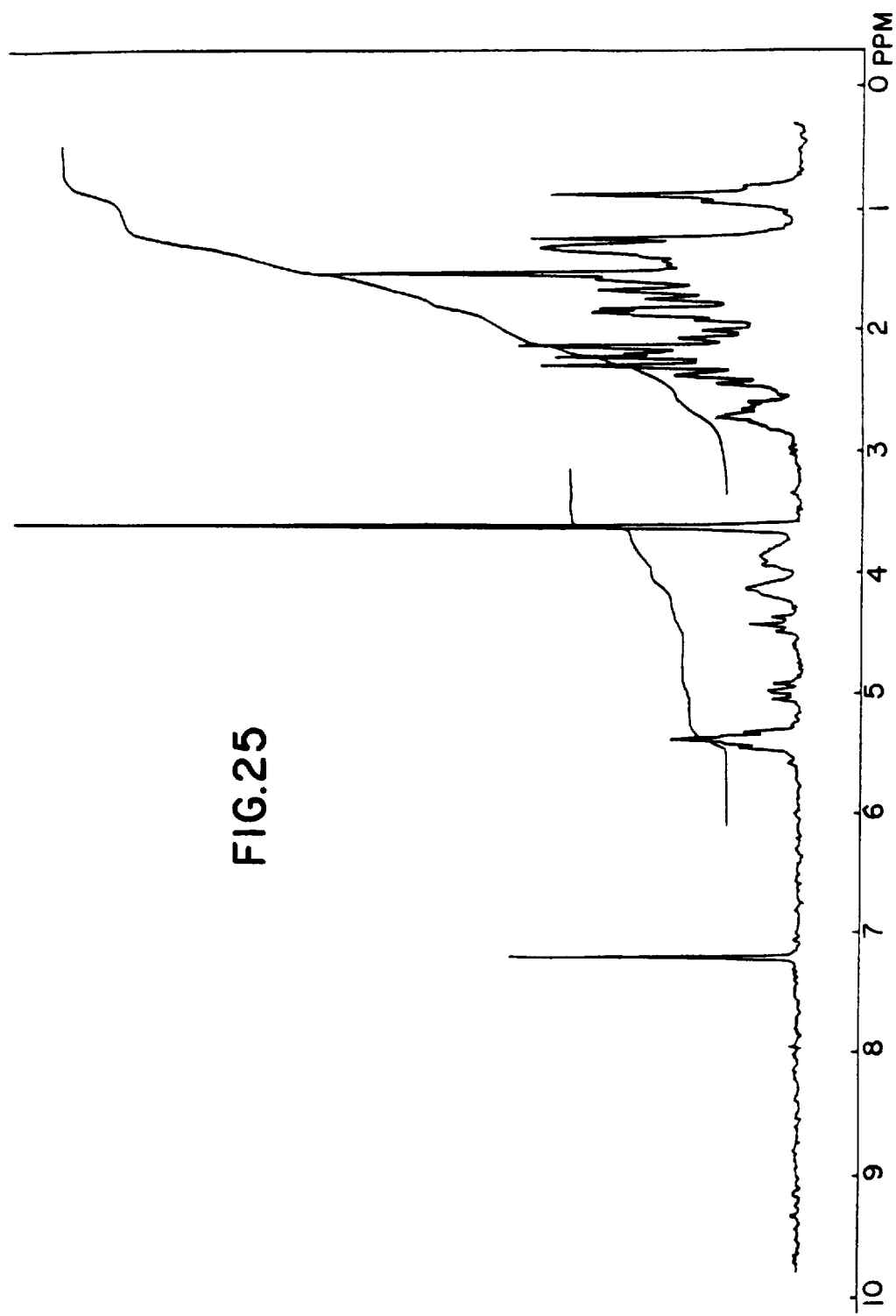

NMR spectrum of 13,14-dihydro-15-keto-16R,S-fluoro-20-methyl-PGF$_2\alpha$ methyl ester (83) is shown in FIG. 25.

Mass (DI) m/z 400, 382, 364, 362

EXAMPLE 27 (cf. Synthetic scheme IX)

Synthesis of 13,14-dihydro-15-keto-16,16-difuloro-PGF$_2\alpha$ methyl ester (96)

(27-1) Synthesis of 1S-2-oxa-3-oxo-6R-(4,4-difluoro-3-oxo-1-trans-octenyl)-7R-(p-phenylbenzoyl)oxy-cis-bicyclo-(3,3,0)octane (84):

(−)-Corey lactone (1) (6.33 g) was oxidized wtih Collins reagent to give aldehyde (2).

Separately, thallium ethoxide (4.26 g) was dissolved in benzene, to which was added a solution of dimethyl (3,3-difluoro-2-oxoheptyl)phosphonate (4.64 g) in benzene, and the solution was stirred for 30 minutes. The crude product obtained after the usual work-up was chromatographed (ethyl acetate/hexane=1/2) to give the compound (84). Yield; 3.88 g (45%)

(27-2) Synthesis of 1S-2-oxa-3-oxo-6R-(4,4-difluoro-3R,S-hydroxy-1-octyl)-7R-(p-phenylbenzoyl)oxy-cis-bicyclo-(3,3,0)octane (86):

Enone (84) (3.88 g) was hydrogenated in ethyl acetate (40 ml) with using 5% palladium/carbon (0.39 g) to give the compound (85).

The above compound was reduced in a mixed solvent (THF : methanol=30/70 ml) with using NaBH$_4$ to give alcohol (86). Yield; 4.02 g (27-3) Synthesis of 1S-2-oxa-3-oxo-6R-(4,4-difluoro-3R,S-t-butyldimethylsilyloxy- 1-octyl)-7R-hydroxy-cis-bicyclo-(3,3,0)octane (88):

Alcohol (86) (4.02 g) was converted into the corresponding silylether (87) in DMF with using t-butyldimethylsilyl chloride and imidazole. The product was converted to the compound (88) with potassium carbonate (1.14 g) in methanol (80 ml). Yield; 2.89 g (83%)

Figure 26:
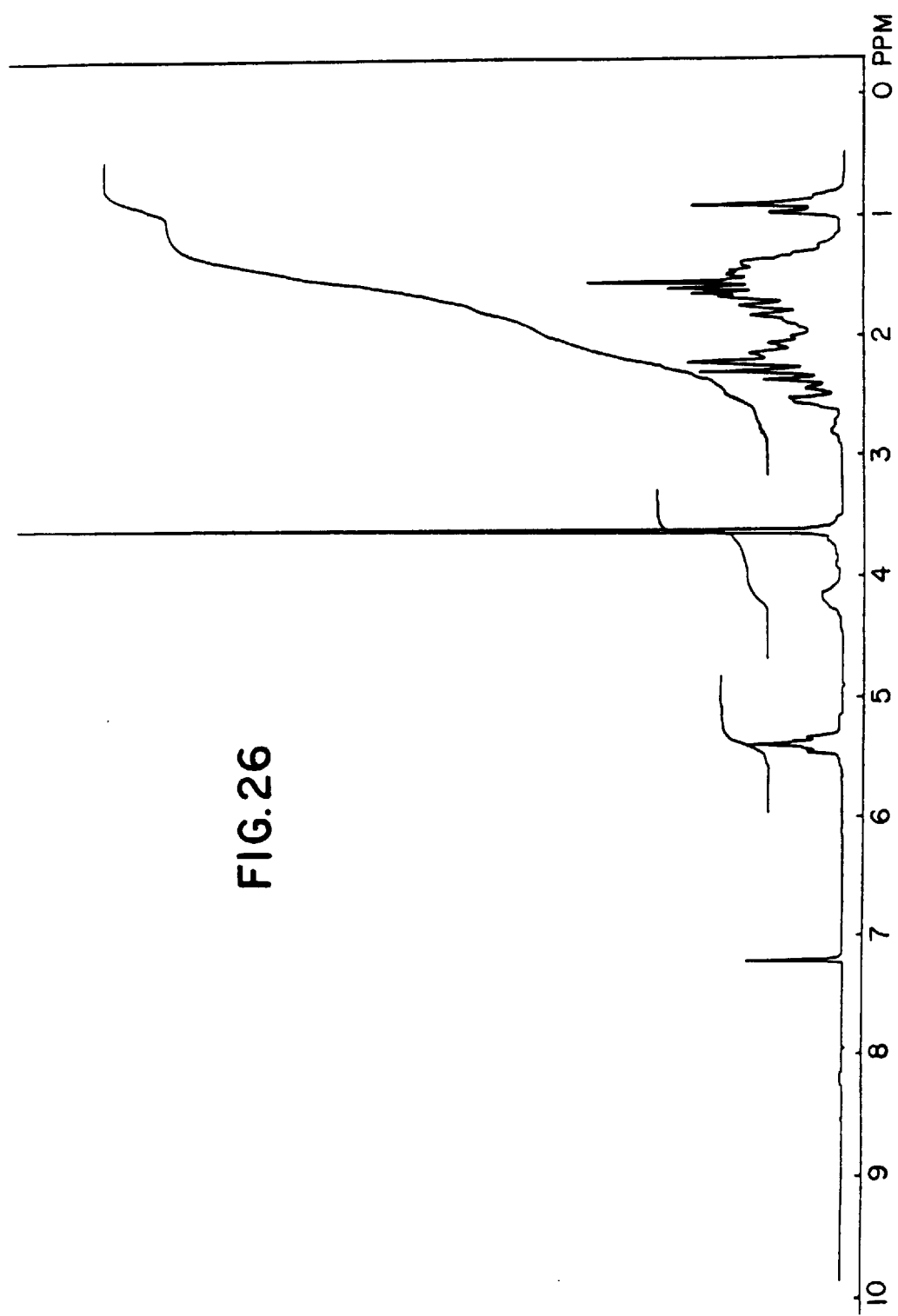

(27-4) Synthesis of 13,14-dihydro-15-keto-16,16-difluoro-PGF$_2\alpha$ methyl ester (96):

In the same manner as described in Example 5, using the compound (88) (2.89 g), the synthetic intermediate (92) was obtained. Yield; 3.02 g In the same manner as described in Example 5, using the compound (92) (0.44 g), 13,14-dihydro-15-keto-16,16-difluoro-PGF$_2$a methyl ester (96) was obtained. Yield; 0.168 g NMR spectrum of 13,14-dihydro-15-keto-16,16-difluoro-PGF$_2\alpha$ methyl ester (96) is shown in FIG. 26. Mass (DI) m/z 404, 386, 368, 355

EXAMPLE 28 (cf. Synthetic scheme X)

Synthesis of 13,14-dihydro-15-keto-16-desbutyl-16-m-trifluoromethylphenoxy-PGF$_2\alpha$ (100)

Figure 27:
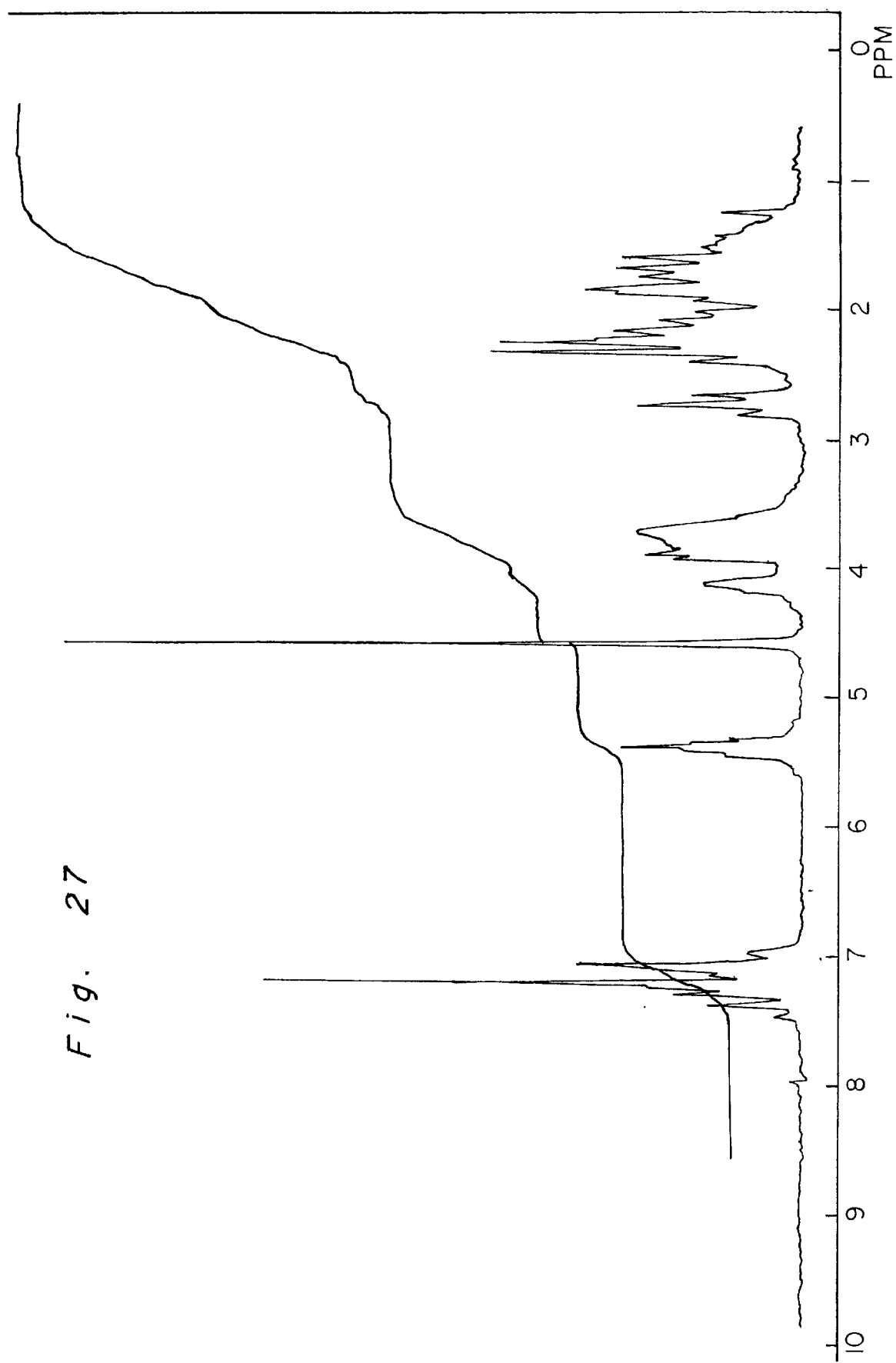

(28-1) Synthesis of tetrapyranyl ether (97):

The crude carboxylic acid (77) was converted to the corresponding tetrapyranyl ether (97) in dichloromethane with using excessive amount of dihydropyran and p-toluenesulfonic acid as a catalyst. Yield; 0.63 g (28-2) Synthesis of alcohol (98):

The above tetrapyranyl ether (97) (0.63 g) was converted to the corresponding alcohol (98) in THF with using tetrabutylammonium fluoride. Yield; 0.38 g (28-3) Synthesis of ketone (99):

The above alcohol (98) (0.38 g) was oxidized with Collins reagent to give ketone (99). Yield; 0.34 g (28-4) Synthesis of 13,14-dihydro-15-keto-16-desbutyl-16-m-trifluoromethylphenoxy-PGF$_2\alpha$ (100):

The above ketone (99) (0.34 g) was kept in a mixed solvent (acetic acid/THF/water=3/1/1) at 45°–50° C. for 4.5 hours. After completion of the reaction, the reaction solution was concentrated. The resulting residue was chromatographed to give 13,14-dihydro-15-keto-16-desbutyl-16-m-trifluoromethylphenoxy-PGF$_2\alpha$ (100). Yield; 0.1 g NMR spectrum of 13,14-dihydro-15-keto-16-desbutyl-16-m-trifluoromethylphenoxy-PGF$_2\alpha$ (100) is shown in FIG. 27. Mass (DI) m/z 458, 441, 423

NMR data of the intermediates obtained in the above Examples 6–27 is shown below:

(30) δ: 0.05 (6H, s), 0.88 (9H, s), 0.75–1.05 (3H), 1.05– 2.5 (23H, m), 2,42 (3H, s), 3.63 (3H, s), 3.4–4.7 (4H, m), 5.37 (2H, m), 7.28 (2H, d, J=9Hz), 7.75 (2H, d, J=9Hz).

(31) 0.05 (6H, s), 0.88 (9H, s), 0.75–1.05 (3H), 1.05–2.7 (20H, m), 3.63 (3H, s), 3.5–3.85 (1H), 3.85–4.1 (0.5H, m), 4.4–4.65 (0.5H, m), 5.35 (2H, m), 6.09 (1H, dd, J=6Hz, J=3Hz), 7.53 (1H, dd, J=6Hz, 3Hz).

(39) 0.87 (3H, t, J=6Hz), 1.05–3.0 (22H, m), 4.93–5.25 (2H, m), 2.2–8.1 (9H, m).

(41) 0.87 (3H, t, J=6Hz), 1.0–3.0 (23H, m), 3.88 (4H, s), 3.6–4.2 (1H), 4.91 (1H, dt, J=6Hz, J=3Hz)

(62) 0.88 (3H, s), 1.05–2.4 (30H, m), 3.60 (3H, s), 3.88 (4H, s), 3.2–4.3 (3H, m), 4.6 (1H, bS), 5.11 (1H, m), 5.40 (2H, m), 7.3–8.1 (5H, m).

(63) 0.89 (3H, s), 1.0–2.4 (31H, m), 3.62 (3H, s), 3.87 (4H, s), 3.3–4.2 (4H, m), 4.55 (1H, bs), 5.42 (2H, m).

(88) 0.05 (6H, s), 0.87 (9H, s), 0.75–1.0 (3H), 1.05–3.0 (17, m), 3.35–3.80 (1H, m), 3.97 (1H, m), 4.88 (1H, dt, J=6Hz, H=3Hz).

(92) 0.08 (6H, s), 0.88 (9H, s), 0.77–1.5 (3H) 1.5–2.5 (29H, m), 3.63 (3H, s), 3.3–4.2 (5H, m), 4.62 (1H, m), 5.40 (2H, m).

Experiment 1

Male Wister rat (8-week old) was anesthetized by intraperitoneally administering urethane (1.25 g/kg). Polyethylene tube was inserted into femoral artery and connected with a pressure transducer to measure blood pressure.

The test drugs were dissolved in ethanol, diluted with Ringer's solution before use and a dose of 1 mg/kg was administered into tale vein. The maximum concentration of ethanol was 2%. As reference, ethanol-Ringer's solution without containing test drugs was used and the effect was checked in each experiment without failing. The rate of change in blood pressure (%) was determined by average of 5 data per group.

The results are shown in Table 1.

TABLE 1

| Test Drug | Change in Blood Pressure (%) |
|---|---|
| 1 | +12 |
| 2 | +17 |
| 3 | +14 |
| 4 | +27 |
| 5 | +18 |
| 6 | +44 |
| 7 | +26 |
| 8 | +7 |
| 9 | +41 |
| 10 | +18 |
| 11 | +20 |
| 12 | +16 |
| 13 | +8 |
| 14 | +32 |
| 15 | +7 |
| 16 | +14 |
| 17 | +10 |
| 18 | +13 |
| 19 | +8 |
| 20 | +5 |
| 21 | +16 |
| 22 | +7 |
| 23 | +35 |
| 24 | +24 |
| 25 | +5 |
| 26 | 0 |

Test Drugs
(1) 13,14-dihydro-15-keto-PGF$_2\alpha$ methyl ester
(2) 13,14-dihydro-15-keto-PGF$_2\alpha$ ethyl ester
(3) 13,14-dihydro-15-keto-9β-PGF$_2\alpha$ methyl ester
(4) 13,14-dihydro-15-keto-16,16-dimethyl-PGF$_2\alpha$ ethyl ester
(5) 13,14-dihydro-15-keto-16R,S-fluoro-PGF$_2\alpha$
(6) 13,14-dihydro-15-keto-16R,S-fluoro-PGF$_2\alpha$ methyl ester
(7) 13,14-dihydro-15-keto-16,16-difluoro-PGF$_2\alpha$ methyl ester
(8) 13,14-dihydro-15-keto-16R,S-fluoro-11R-methyl-PGF$_2\alpha$ methyl ester
(9) 13,14-dihydro-15-keto-16R,S-fluoro-20-methyl-PGF$_2\alpha$ methyl ester
(10) 13,14-dihydro-15-keto-16R,S-fluoro-20-ethyl-PGF$_2\alpha$
(11) 13,14-dihydro-15-keto-16R,S-fluoro-20-ethyl-PGF$_2\alpha$ methyl ester
(12) 13,14-dihydro-15-keto-16R,S-fluoro-20-ethyl-11R-methyl-PGF$_2\alpha$ methyl ester
(13) 13,14-dihydro-15-keto-17S-methyl-PGF$_2\alpha$ ethyl ester
(14) 13,14-dihydro-15-keto-20-methyl-PGF$_2\alpha$ methyl ester
(15) 13,14-dihydro-15-keto-20-ethyl-PGF$_2\alpha$
(16) 13,14-dihydro-15-keto-20-ethyl-PGF$_2\alpha$ methyl ester
(17) 13,14-dihydro-15-keto-20-ethyl-PGF$_2\alpha$ ethyl ester
(18) 13,14-dihydro-15-keto-20-ethyl-PGF$_2\alpha$ isopropyl ester
(19) 13,14-dihydro-15-keto-20-ethyl-PGF$_2\alpha$ n-butyl ester
(20) 13,14-dihydro-15-keto-20-ethyl-PGF$_2\alpha$ methyl ester
(21) 13,14-dihydro-15-keto-20-n-propyl-PGF$_2\alpha$ methyl ester
(22) 13,14-dihydro-15-keto-20-n-butyl-PGF$_2\alpha$ methyl ester
(23) 13,14-dihydro-15-keto-16-desbutyl-16-(m-trifluoromethylphenoxy)-PGF$_2\alpha$ methyl ester
(24) 13,14-dihydro-15-keto-PGF$_1\alpha$ ethyl ester
(25) 13,14-dihydro-15-keto-20-ethyl-PGF$_1\alpha$ methyl ester
(26) Ringer's solution As is obvious from the above results, 13,14-dihydro-15-keto-prostaglandins of the F series of the present invention distinctly show vasopressor effect. Further, it has been found that those containing halogen such as fluorine or lower alkyl group such as methyl or phenoxy especially show surprisingly great vasopressor effect.

Experiment 2

Measurement of pulse

Male Wister rat (8-week old) was anesthetized by intraperitoneally administering urethane (1.25 g/kg). A tachometer was operated by R wave of electrocardiogram of exterminal derivation. The effect of the tested 15-keto-PGEs on pulse is evaluated by the value calucurated from the following formula:

$$\frac{\text{pulse after administration} - \text{pulse before administration}}{\text{pulse before administration}} \times 100$$

The results are shown in Table 2.

Experiment 3

Trachea contraction

Trachea was enucleated from Std : Hartley guinea pig, longitudinally incised heterolateral side to trachea unstriated muscle, then transversely truncated. The resulting ring-shaped trachea tissue (7 pieces) were connected like chain with string and suspended in a magnus tube into which Krebs buffer containing enzyme was filled. The each test drug was dissolved in ethanol and then diluted with distilled water, which was applied to Krebs buffer in the magnus tube. The concentration of ethanol was controlled at less than 0.2%. The contraction by the test drug was indicated by $EC_{50}$, which is a concentration of the drug showing 50% contraction when the contraction by 30 mM KCl is assumed 100%. The results are shown in Table 2.

Experiment 4

Airway resistance

Male Std : Hartley guinea pig was anesthetized by intraperitoneally administering urethane (1.5 g/kg). After cannulation in trachea, 0.3 mg/kg of parachronium was intravenously administered to immobilize, and artificial respiration was conducted using a respirator. The change in the inner pressure of the airway was recorded using bronchospasm transducer. The test drug was intravenously administered through the polyethylene tube inserted in the external jugular vein. The drug which raised the inner resistance of the airway when administered at the dose of 1 mg/kg was evaluated as positive for airway resistance raising activity.

The results are shown in Table 2.

Experiment 5

Enteron contraction

Ileum was removed from male Wister rat and suspended in a magnus tube. Contraction was induced several times with acetylcholine at the concentration of $1 \times 10^{-6}$ g/ml. After more than two contractions with same intensity were obtained, the test drug was administered in the same manner as in Experiment 3. Contraction by the test drug was indicated by $EC_{50}$, which is a concentration of the test drug showing 50% contraction, when the contruction induced by $1 \times 10^{-6}$ g/ml of acetylcholine is assumed 100%.

The results are shown in Table 2.

Experiment 6

Acute toxicity

Using Male Slc-ddY mouse (5 weeks old), acute toxicity upon oral administration ($LD_{50}$) was examined. The results are shown in Table 2.

TABLE 2

|  | Drug 18 | Drug 16 | Drug 1 | PGF$_2$α |
|---|---|---|---|---|
| Blood Pressure* | ↑ | ↑ | ↑ | ↓ → ↑ |
| Pulse* | → | → | ↑ | ↓ → ↑ |
| Trachea** Contraction | – | – | – | + |
| Airway*** Resistance | – |  |  | + |
| Enteron** Contraction | – | – | – | ++ |
| LD$_{50}$ (oral) | >2000 mg/kg | >2000 mg/kg |  |  |

*↑: increase more than 10%
↓: decrease more than 10%
→: no change observed
**++: EC$_{50}$ < 10$^{-7}$
+: 10$^{-7}$ ≤ EC$_{50}$ ≤ 10$^{-6}$
–: 10$^{-6}$ < EC$_{50}$
***–: no effect
+: increase airway resistance As is obvious from the above resluts, 13,14-dihydro-15-keto-PGFs did not show ephemeral decrease in pulse as well as blood pressure which PGF$_2$α usually shows, Further, 13,14-dihydro-15-keto-20-alkyl PGFs are found to show no effect on pulse. 13,14-Dihydro-15-keto-PGFs shown no or extremely reduced effect on trachea or enteron contraction without showing side-effect such as increase in airway resistance. Therefore, 13,14-dihydro-15-keto-PGFs are useful as vasopressor with no or little side-effects. Particularly, 13,14-dihydro-15-keto-20-alkyl-PGFs are free from side effect, i.e., slight increase in pulse and specifically show vasopressor activity. Moreover, their toxicity are extremely weak, that is, no death was caused by oral administration of 2,000 mg/kg of the compound.

Synthetic scheme I

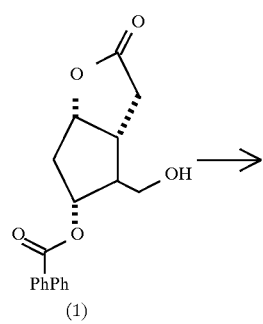

(1)

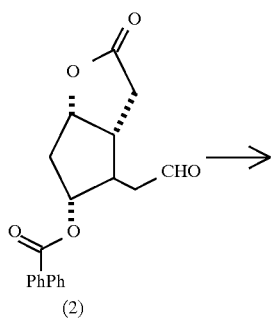

(2)

-continued
Synthetic scheme I

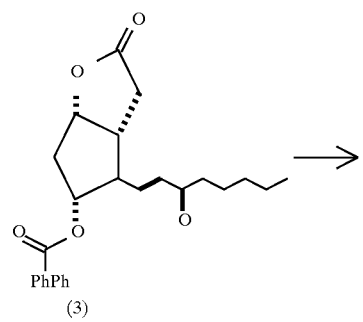

(3)

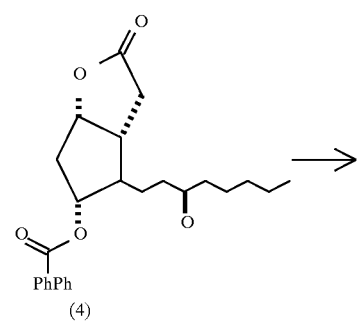

(4)

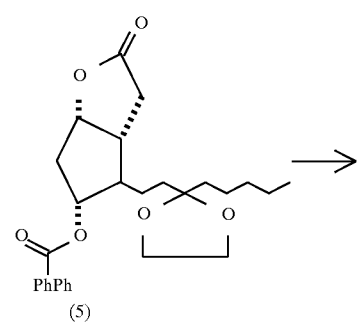

(5)

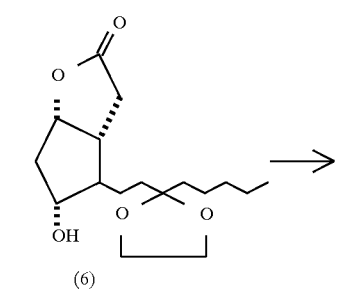

(6)

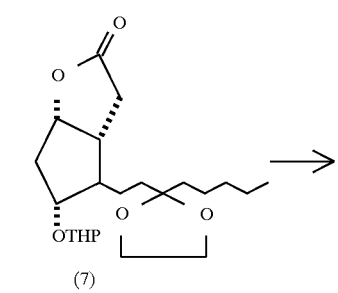

(7)

Synthetic scheme I -continued
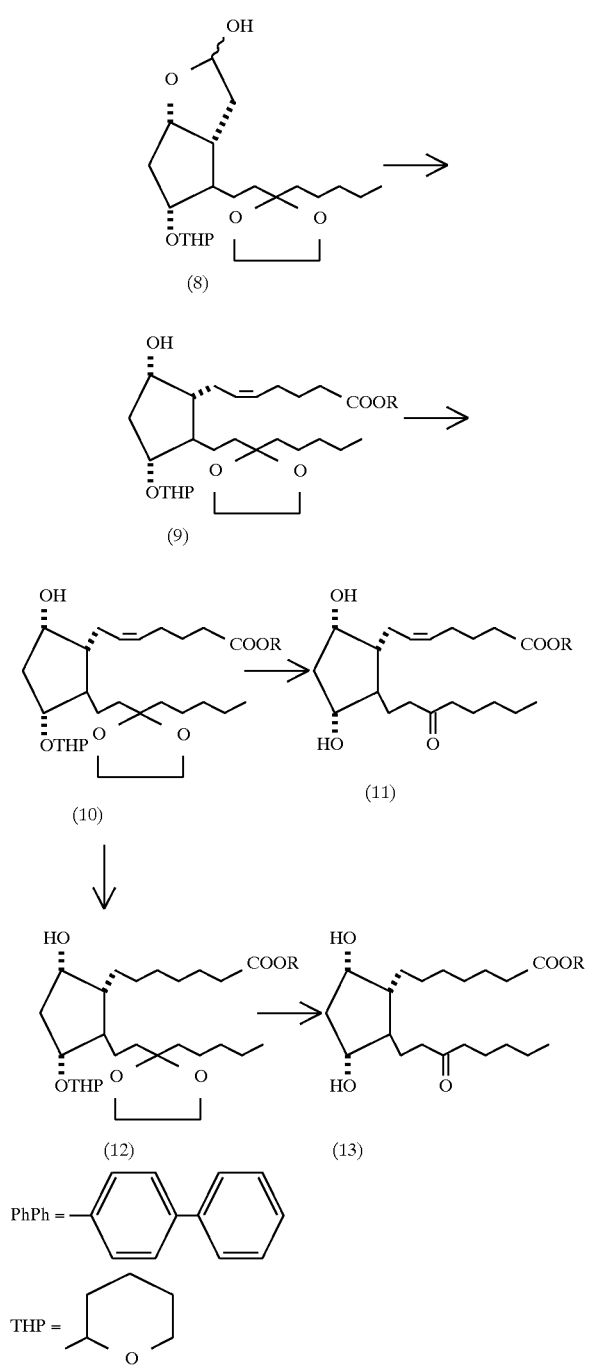
Synthetic scheme II
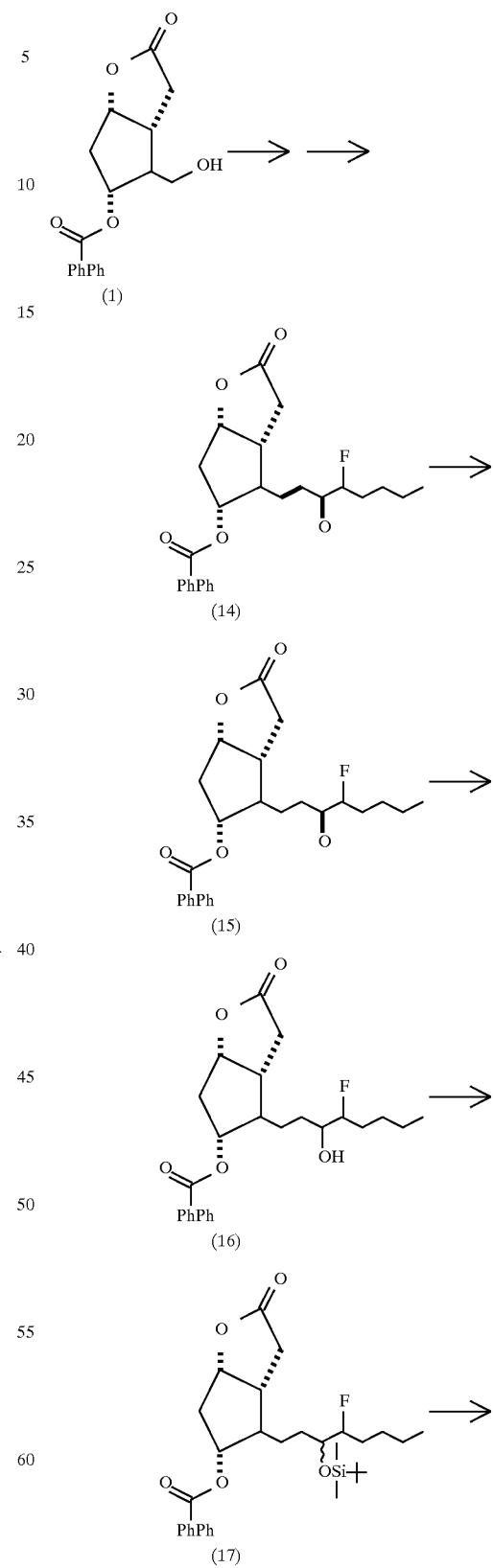

-continued
Synthetic scheme II
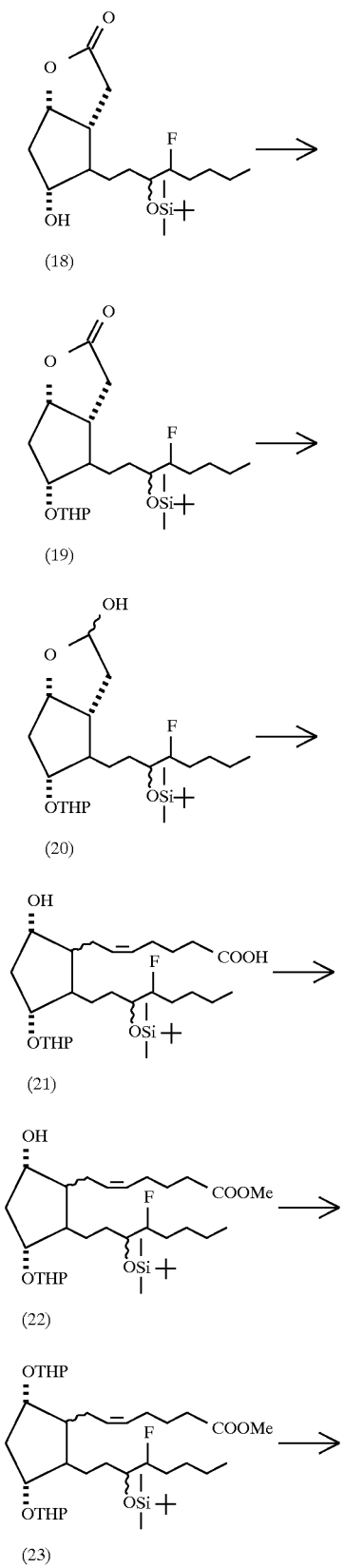
-continued
Synthetic scheme II
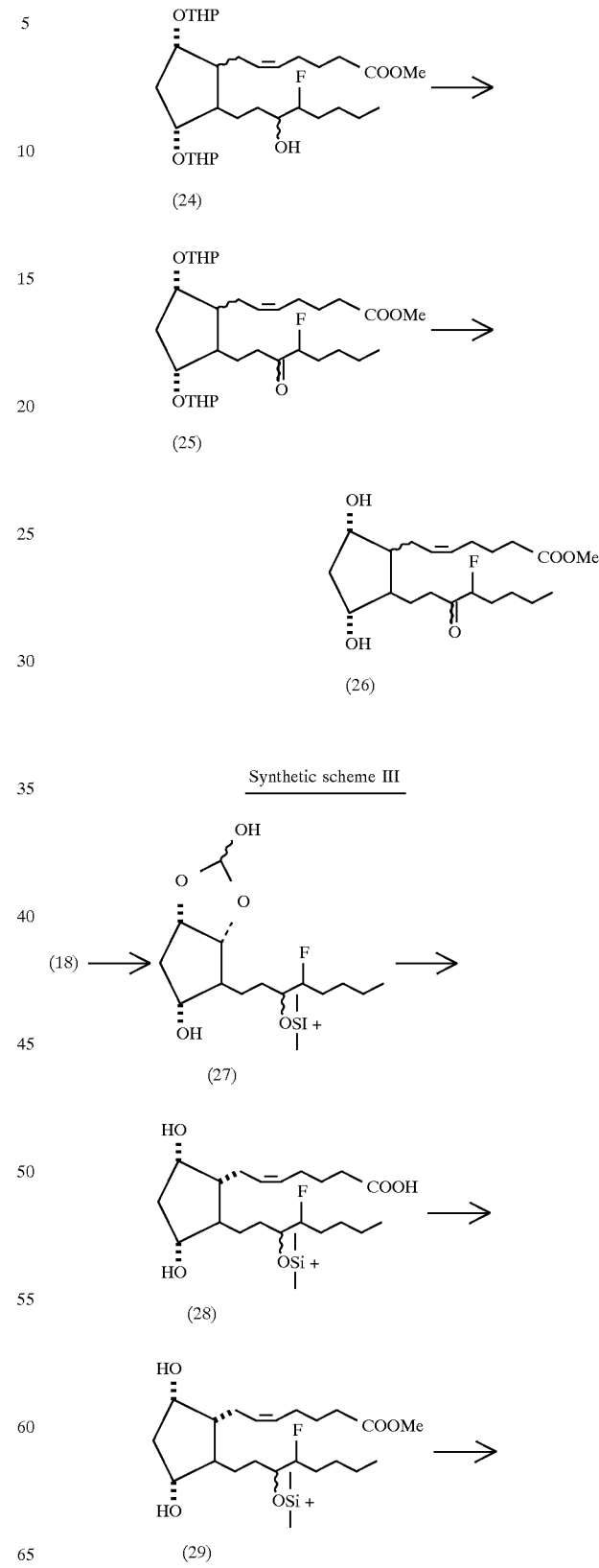
Synthetic scheme III

33
-continued
Synthetic scheme III
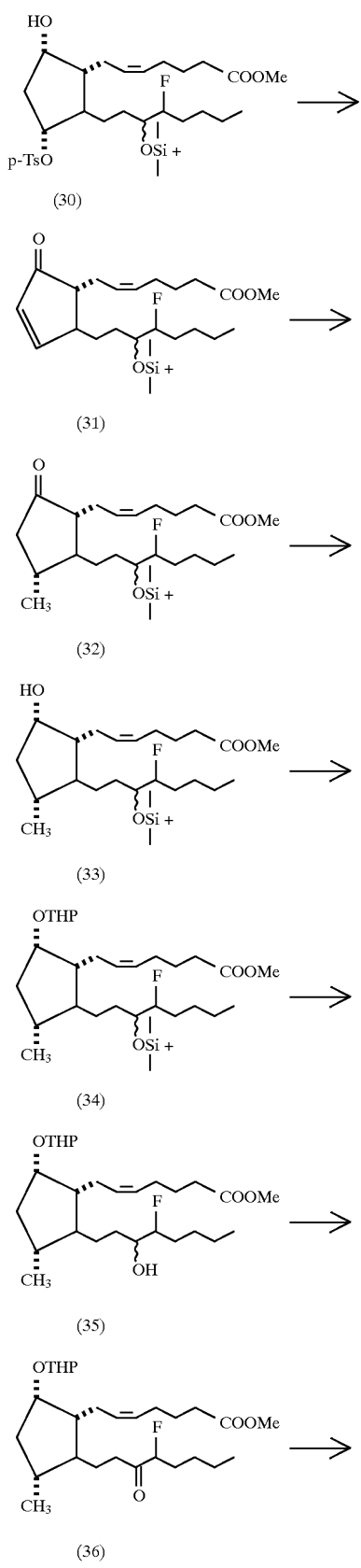
34
-continued
Synthetic scheme III
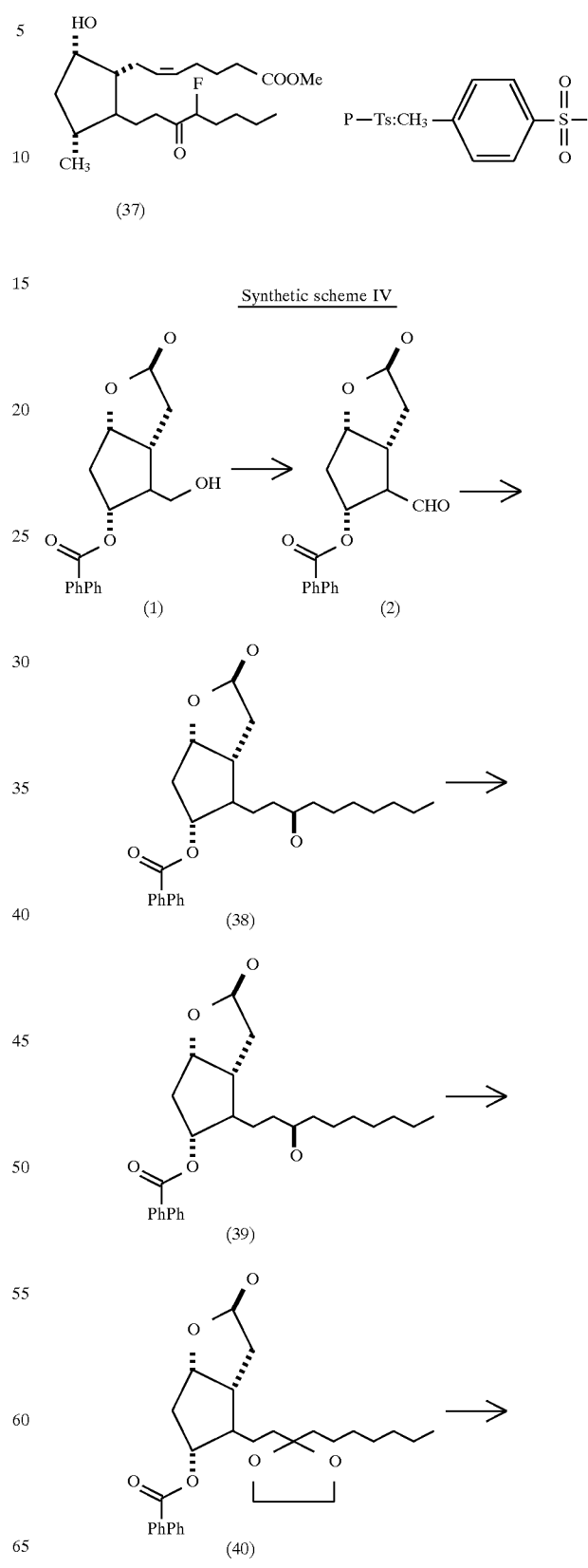

Synthetic scheme IV
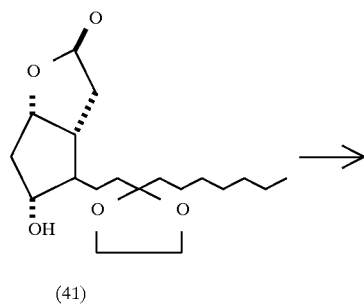
(41)
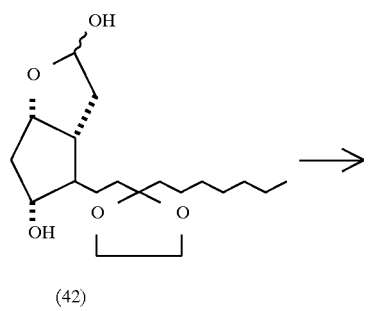
(42)
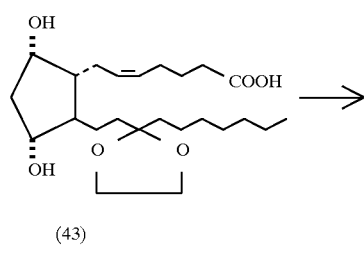
(43)
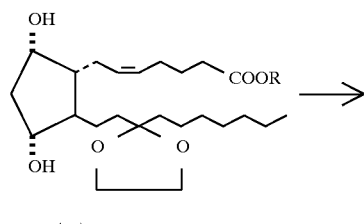
(44)
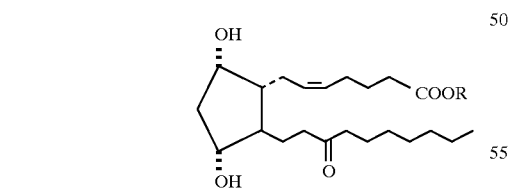
(45)
Synthetic scheme V
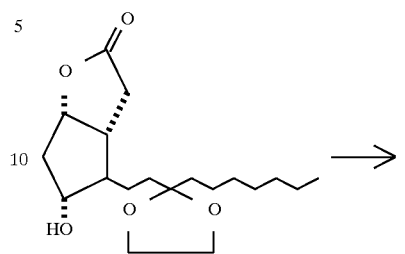
(41)
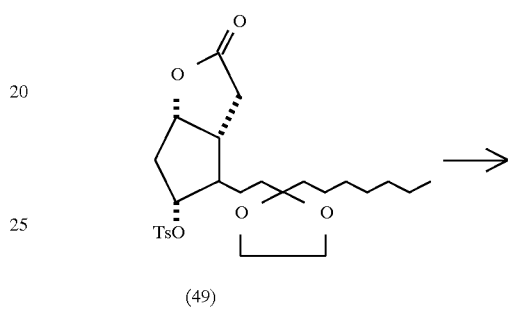
(49)
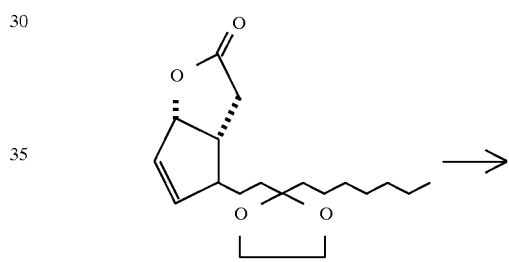
(50)
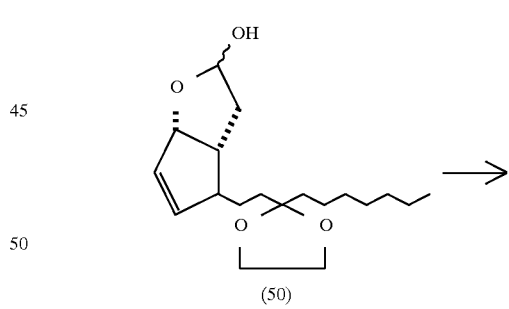
(50)

37
-continued
Synthetic scheme V
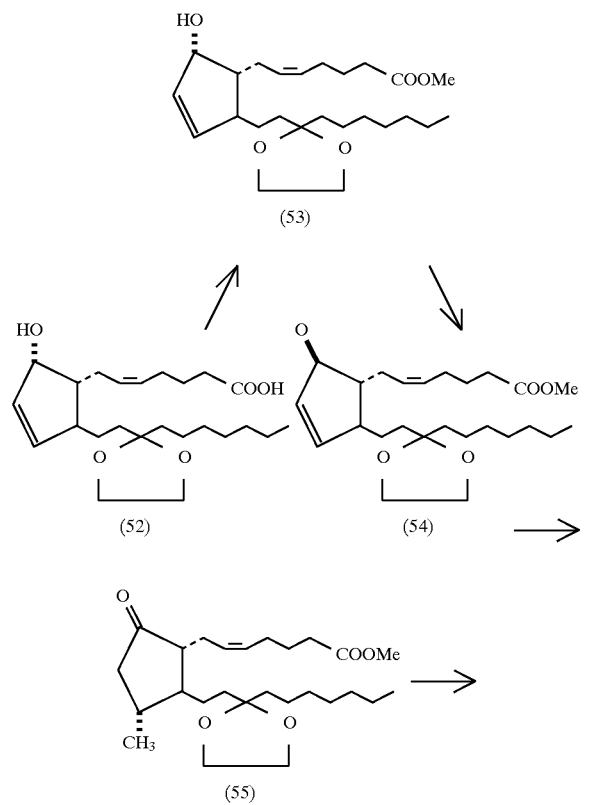
Synthetic scheme VI
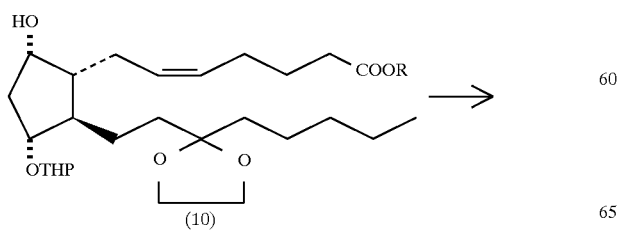
38
-continued
Synthetic scheme VI
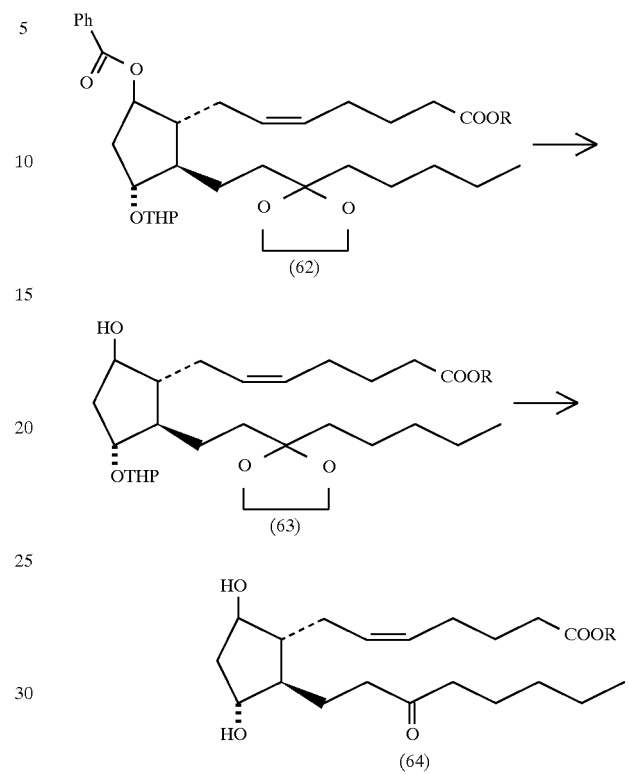
Synthetic scheme VII
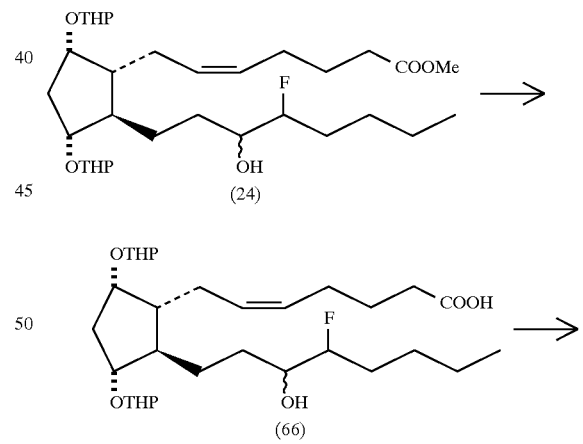

Synthetic scheme VII -continued
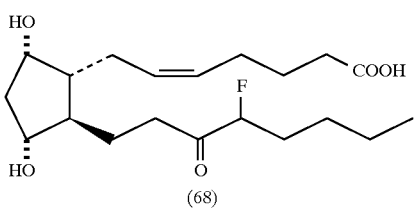
(68)
Synthetic scheme VIII
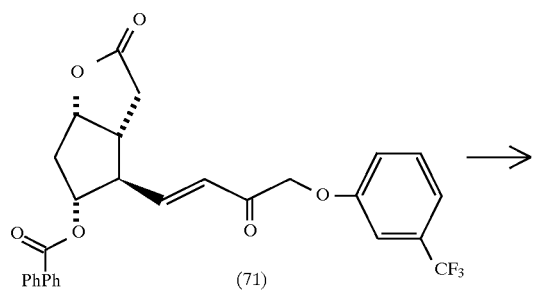
(71)
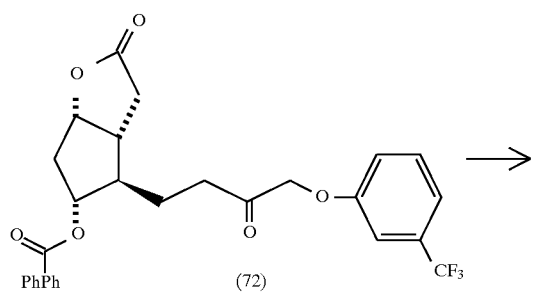
(72)
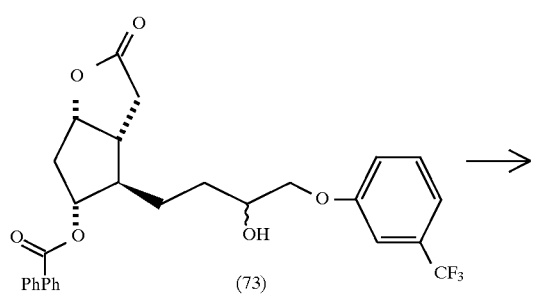
(73)
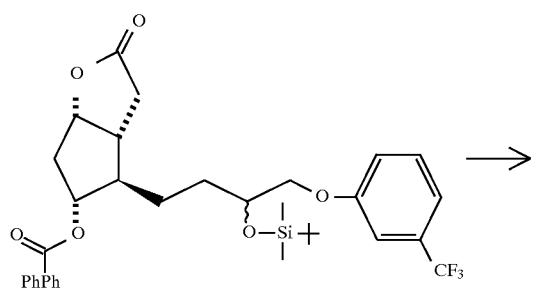
(74)
Synthetic scheme VIII -continued
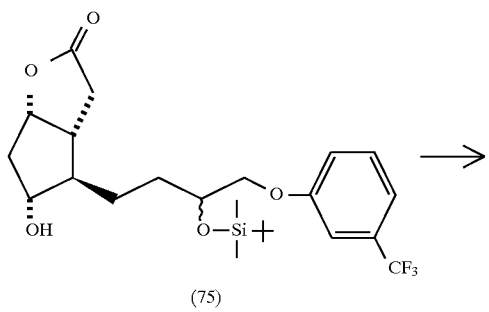
(75)
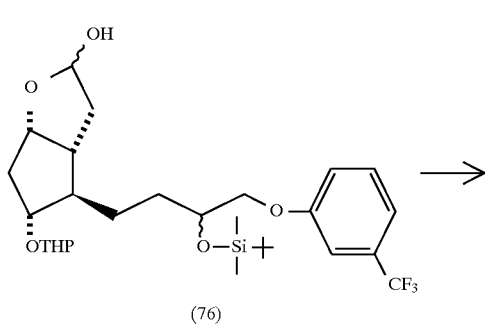
(76)
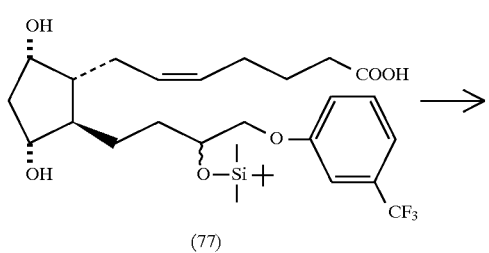
(77)
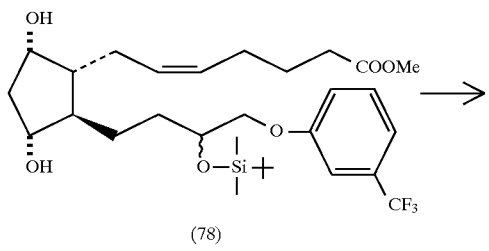
(78)
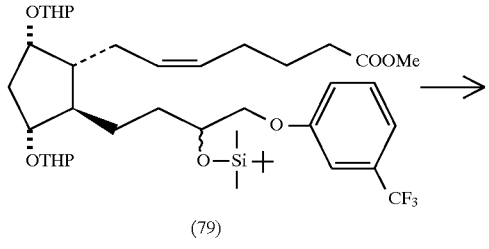
(79)
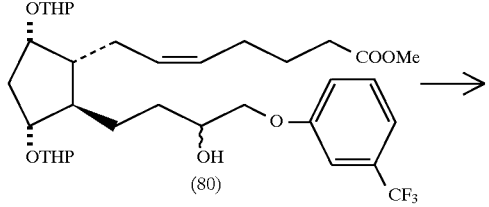
(80)

41
-continued
Synthetic scheme VIII
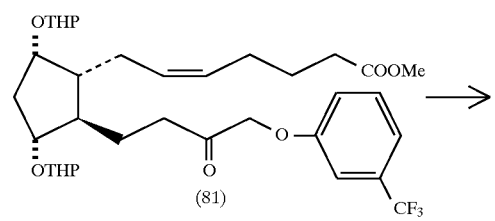
(81)
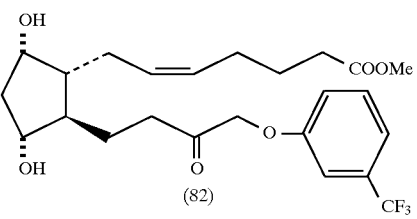
(82)
Synthetic scheme IX
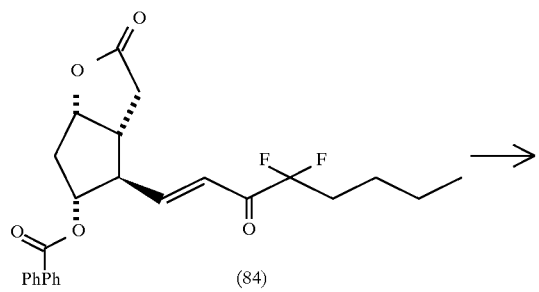
(84)
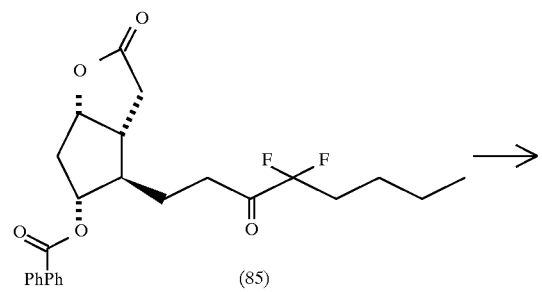
(85)
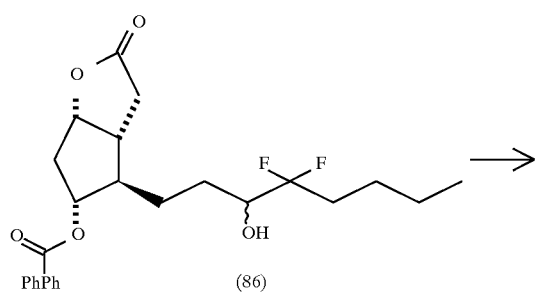
(86)
42
-continued
Synthetic scheme IX
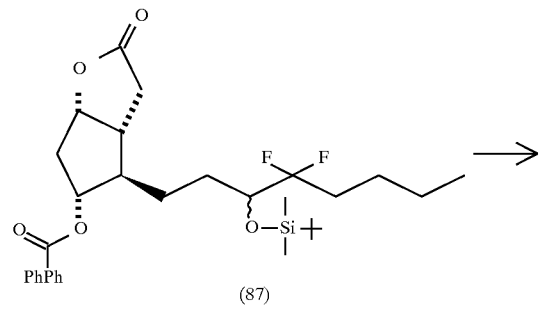
(87)
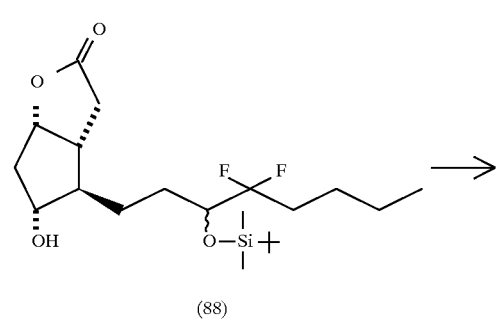
(88)
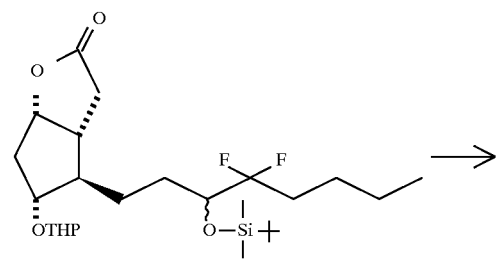
(89)
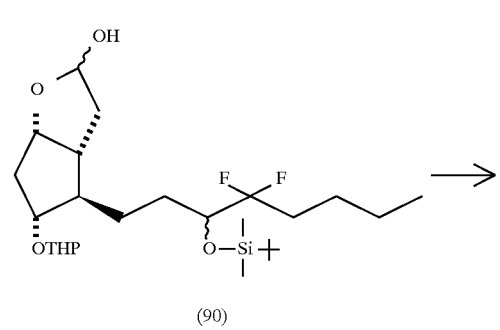
(90)
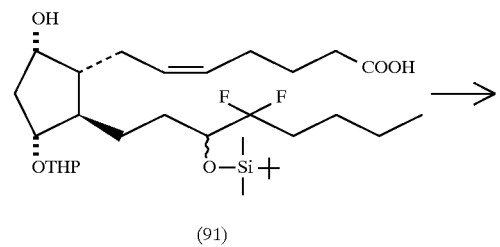
(91)

-continued
Synthetic scheme IX

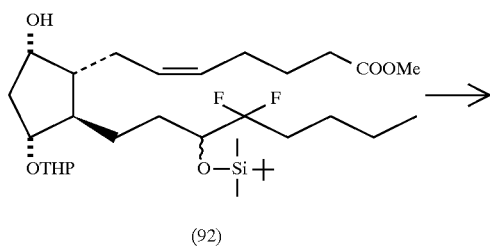
(92)

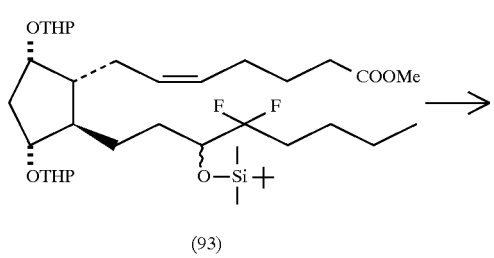
(93)

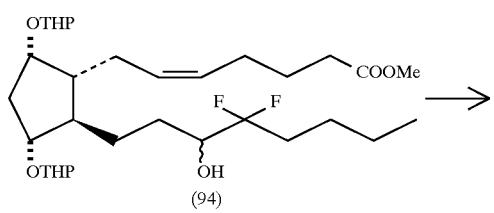
(94)

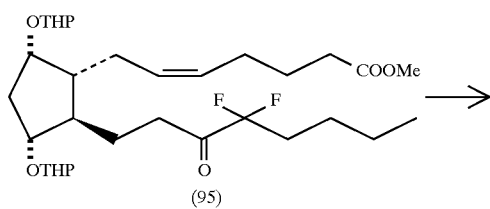
(95)

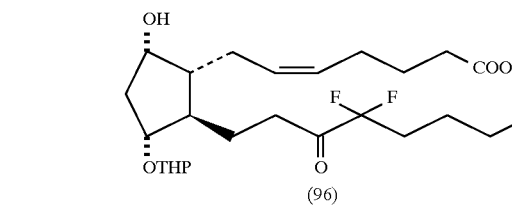
(96)

Synthetic scheme X

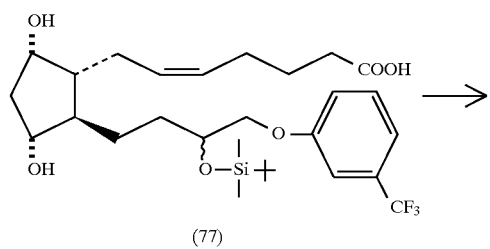
(77)

-continued
Synthetic scheme X

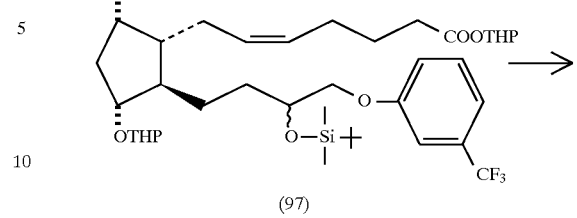
(97)

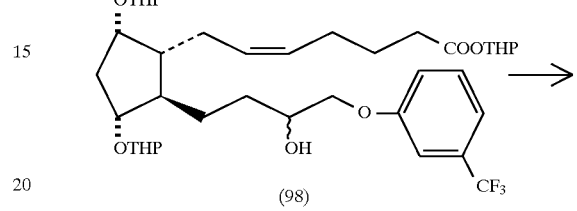
(98)

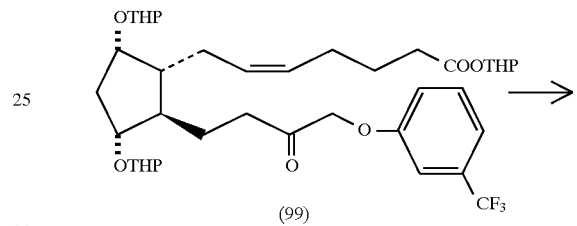
(99)

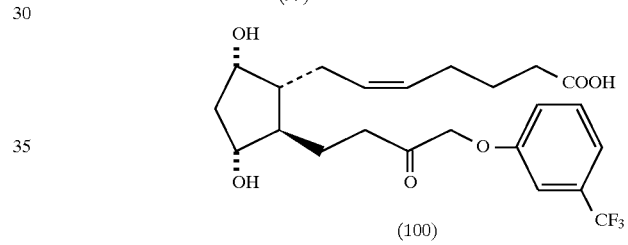
(100)

What is claimed is:

1. A 13,14-dihydro-15-keto-PGF represented by the formula:

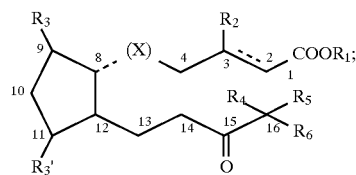

in which a bond between C-2 and C-3 is a single or a double bond, X is a group:

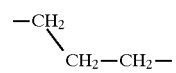

$R_1$ is a hydrogen atom or a $C_{1-4}$ alkyl, phenyl, benzoyl, hydroxyalkyl, alkoxyalkyl, trialkylsilyl or tetrahydropyranyl group;

$R_2$ is a hydrogen atom or a lower alkyl group;

$R_3$ is hydroxyl;

$R_{3'}$ is hydroxyl; $R_4$ and $R_5$ are independently a hydrogen atom or a lower alkyl group, $R_6$ is a $C_{1-9}$ alkyl group containing a $C_{1-2}$ alkoxy substituent or

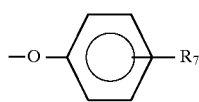

(wherein $R_7$ is a hydrogen or halogen atom or a halogenated methyl group; and a physiologically acceptable salt of said 13,14-dihydro-15-keto-PGF.

2. The 13,14-dihydro-15-keto-PGF of claim 1, wherein $R_1$ is a $C_{1-4}$ alkyl group.

3. The 13,14-dihydro-15-keto-PGF according to claim 1, wherein at least one of $R_4$ and $R_5$ is a lower alkyl group, or a physiologically acceptable salt thereof.

4. The 13,14-dihydro-15-keto-PGF of claim 1 comprising a 13,14-dihydro-15-keto-16-substituted-PGF represented by the formula:

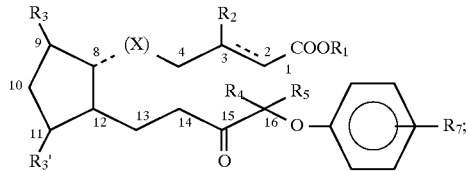

or a physiologically acceptable salt thereof.

5. The 13,14-dihydro-15-keto-PGF according to claim 1, wherein each of $R_4$ and $R_5$ is a lower alkyl group, or a physiologically acceptable salt thereof.

6. The 13,14-dihydro-15-keto-PGF according to claim 1, comprising a 13,14-dihydro-15-keto-16-desbutyl-16-trifluoromethyl-phenoxy-PGF or a physiologically acceptable salt thereof.

7. A 13,14-dihydro-15-keto-PGF represented by the formula:

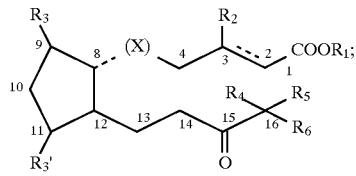

in which a bond between C-2 and C-3 is a single or a double bond, X is a group:

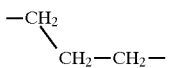

$R_1$ is a hydrogen atom or a $C_{1-4}$ alkyl, phenyl, benzoyl, hydroxyalkyl, alkoxyalkyl, trialkylsilyl or tetrahydropyranyl group;

$R_2$ is a hydrogen atom or a lower alkyl group;

$R_3$ is hydroxyl;

$R_{3'}$ is hydroxyl; $R_4$ and $R_5$ are independently a hydrogen atom or a lower alkyl group, $R_6$ is a $c_{6-9}$ alkyl group which may be branched or contain a double bond; and a physiologically acceptable salt of said 13,14-dihydro-15-keto-PGF.

8. The 13,14-dihydro-15-keto-PGF of claim 7, wherein $R_1$ is a $C_{1-4}$ alkyl group.

9. The 13,14-dihydro-15-keto-PGF according to claim 7, wherein at least one of $R_4$ and $R_5$ is a lower alkyl group, or a physiologically acceptable salt thereof.

10. The 13,14-dihydro-15-keto-PGF according to claim 7, wherein each of $R_4$ and $R_5$ is a lower alkyl group, or a physiologically acceptable salt thereof.

11. A 13,14-dihydro-15-keto-20-ethyl-PGF represented by the formulae:

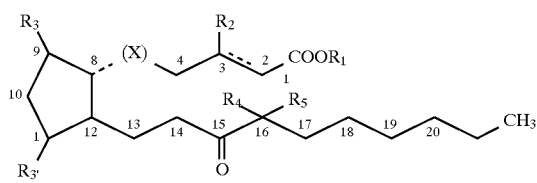

in which a bond between C-2 and C-3 is a single or a double bond, X is a group:

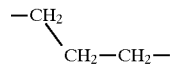

$R_1$ is a hydrogen atom or a $C_{1-4}$ alkyl, phenyl, benzoyl, hydroxyalkyl, alkoxyalkyl, trialkylsilyl or tetrahydropyranyl group;

$R_2$ is a hydrogen atom or a lower alkyl group;

$R_3$ is hydroxyl;

$R_{3'}$ is a hydroxyl; $R_4$ and $R_5$ are independently a hydrogen atom or a lower alkyl group or a physiologically acceptable salt thereof.

12. A 13,14-dihydro-15-keto-PGF of claim 7 being a 13,14-dihydro-15-keto-20-ethyl-PGF$_{1\alpha}$, a $C_1$–$C_4$ alkyl ester or a physiologically acceptable salt thereof.

13. A 13,14-dihydro-15-keto-PGF of claim 7 being a 13,14-dihydro-15-keto-20-ethyl-PGF$_{1\alpha}$ isopropyl ester.

* * * * *